(12) United States Patent
Ohta et al.

(10) Patent No.: US 7,018,993 B2
(45) Date of Patent: Mar. 28, 2006

(54) ANTIANDROGENIC AGENT

(75) Inventors: Masateru Ohta, Shizuoka (JP);
Nobuaki Kato, Shizuoka (JP);
Mitsuaki Nakamura, Shizuoka (JP);
Kazutaka Tachibana, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 47 days.

(21) Appl. No.: 10/312,730

(22) PCT Filed: Jul. 2, 2001

(86) PCT No.: PCT/JP01/05724

§ 371 (c)(1),
(2), (4) Date: Dec. 30, 2002

(87) PCT Pub. No.: WO02/02589

PCT Pub. Date: Jan. 10, 2002

(65) Prior Publication Data

US 2003/0158164 A1    Aug. 21, 2003

(30) Foreign Application Priority Data

Jun. 30, 2000 (JP) ............................. 2000-237722
Feb. 23, 2001 (JP) ............................. 2001-049064

(51) Int. Cl.
*A61K 31/56* (2006.01)
*C07J 1/00* (2006.01)

(52) U.S. Cl. .................... 514/178; 514/179; 552/638; 552/641

(58) Field of Classification Search ............... 514/178, 514/179; 552/638, 641
See application file for complete search history.

(56) References Cited

U.S. PATENT DOCUMENTS 3,833,621 A * 9/1974 Petrow et al. ............. 552/597
4,659,516 A   4/1987 Bowler et al.

FOREIGN PATENT DOCUMENTS

| EP | 0 138 504 | 4/1985 |
|---|---|---|
| WO | 91 00732 | 1/1991 |
| WO | 91 00733 | 1/1991 |
| WO | 95 17192 | 6/1995 |
| WO | 97 49709 | 12/1997 |
| WO | 98 25916 | 6/1998 |

OTHER PUBLICATIONS

Wakeling et al., "A Potent Specific Pure Antiestrogen with Clinical Potential", *Cancer Research*, (1991), vol. 51, pp. 3867-3873.

Bourguet et al., "Crystal structure of the ligand-binding domain of the human nuclear receptor RXR-α", *Nature*, (1995), vol. 375, pp. 377-382.

* cited by examiner

*Primary Examiner*—Barbara P. Badio
(74) *Attorney, Agent, or Firm*—Browdy and Neimark, PLLC

(57) ABSTRACT

A compound pf general formula (I):

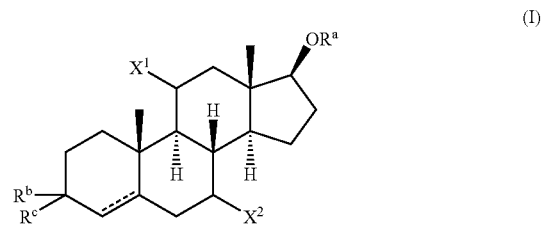

(I)

wherein, for example,
$X^1$ and $X^2$ independently represent a hydrogen atom.
$R^a$ represents a hydrogen atom or a protecting group for a hydroxyl group.
$R^b$ and $R^c$ form an optionally protected —(C=O)— together with the 3-position carbon atom attached to $R^b$ and $R^c$, and
the broken line forms a single bond or double bond together with the solid line, or a pharmaceutically acceptable salt of the compound or a prodrug thereof.

27 Claims, 1 Drawing Sheet

ANTIANDROGENIC AGENT

The present application is the U.S. National phase of PCT/JP01/05724, filed Monday, Jul. 2, 2001, and claims priority from Japanese application 237722/2000, filed Jun. 30, 2000, and Japanese application 49064/2001, filed Feb. 23, 2001.

TECHNICAL FIELD

The present invention relates to androstane derivatives having various substituents at positions 7 and/or 11; substances serving as antagonists against androgen receptor and substantially free of agonistic effects; and pharmaceutical compositions comprising the above androstane derivatives and substances. More specifically, the present invention relates to compounds having a terminal-branched side chain as a substituent at position 7 or 11 on the androstane skeletal structure.

BACKGROUND ART

The male hormone androgen has been known to have a close relationship with prostate cancer, benign prostatic hyperplasia, male pattern alopecia, precocious puberty, acne vulgaris, seborrhea and hypertrichosis. For example, it is known that castrated or hypogonadic patients rarely develop prostate cancer and benign prostatic hyperplasia.

As anti-androgen agents (i.e., antagonists against androgen receptor), various compounds are already used including cyproterone acetate, chlormadinone acetate, flutamide and bicalutamide. Cyproterone acetate is known to inhibit the progress of acne and the development of baldness in teenage patients. Cyproterone acetate is also used for the treatment of virilization and alopecia in female patients. Flutamide and bicalutamide are used as therapeutic agents for prostate cancer.

These anti-androgen agents are effective in many cases including drug therapy for prostate cancer and hence are regarded as one of the potent therapeutic agents. However, one of the problems with these anti-androgen agents is that in almost all cases, recurrences will occur, namely, androgen resistance develops, two to five years after the agents have proved effective on the disease.

Recently, hydroxyflutamide which is an active form of flutamide has been reported to enhance the transcriptional activity of androgen receptor at a concentration of 10 μmol/L. In addition, prostate cancer patients undergoing treatment with flutamide were reported to have blood hydroxyflutamide levels of several μmol/L which the report says corresponds to a concentration at which hydroxyflutamide showed its agonistic effects (see J. Biol. Chem., vol. 270, 19998–20003, 1995). There is also a report indicating that castrated rats continuously administered with cyproterone acetate and chlormadinone acetate for two weeks showed an increase in their prostate weight (Journal of Japan Endocrine Society, vol. 66, 597–606, 1990). Further, flutamide and bicalutamide were reported to have side effects such as liver toxicity.

On the other hand, an estrogen receptor antagonist is known as an example of a pure antagonist which serves as an antagonist against nuclear receptors without having agonistic effects, i.e., a substance which completely inhibits the action of the receptors (see, for example, WO98/25916, European Patent Publication No. 0138504, U.S. Pat. No. 4,659,516 and Cancer Res., 1991, 51, 3867). The molecular structures of hormone-binding domains in nuclear receptors such as RXR (retinoid-X receptor) and RAR (retinoic acid receptor) are being clarified by X-ray crystal structure analysis or other techniques (see, for example, Nature, vol. 375, 377–382, 1995).

WO97/49709 discloses an androgen receptor modulator comprising a non-steroidal tetracyclic compound.

Steroid compounds having an aminocarbonylalkyl group at position 7 or an aminocarbonylalkynyl group at position 17 are known from WO91/00732.

Steroid compounds having an aromatic ring or an alkyloxy group at position 11 are known from, for example, WO95/17192 which discloses RU486, a modifier for multiple drug resistance.

Also, compounds having various substituents at positions 7 and/or 11 are disclosed in the co-owned Japanese Patent Application Nos. Hei 11-274956 (filed on Aug. 23, 1999; hereinafter referred to as Application A) and Hei 11-338334 (filed on Oct. 22, 1999; hereinafter referred to as Application B).

DISCLOSURE OF THE INVENTION

An object of the present invention is to provide androstane derivatives having various terminal-branched side chains as substituents at positions 7 and/or 11 or pharmaceutically acceptable salts of the derivatives or prodrugs thereof.

Another object of the present invention is to provide substances serving as antagonists against androgen receptor and substantially free of agonistic effects or pharmaceutically acceptable salts of the substances or prodrugs thereof.

Yet another object of the present invention is to provide pharmaceutical compositions comprising the above androstane derivatives and pharmaceutical compositions comprising the above substances.

In order to achieve the above objects, the present inventors presumed that the side effects, including androgen resistance and increased prostate weight, of conventionally known androgen receptor antagonists would be due, in part, to their agonistic effects which allowed androgen-responsive cells (e.g., prostate cells) to grow; the present inventors then started to design an antagonist free of agonistic effects on androgen receptor, i.e., a pure antagonist against androgen receptor, based on the expectation that such a pure antagonist could provide an anti-androgen agent without the risk of developing androgen resistance due to prolonged administration and/or without the risk of side effects including liver toxicity. Thus, the present inventors found that a substance or compound expected to be a pure antagonist against androgen receptor and/or an anti-androgen agent with a reduced risk of side effects including liver toxicity could be designed as follows. First, the androgen receptor was modeled from the existing nuclear receptors such as RXR and RAR by homology modeling using a software package such as Homology (MSI) or Look (MAG). Second, testosterone and/or dihydrotestosterone was used as a ligand to create a complex model between ligand and androgen receptor, based on which a pure antagonist against androgen receptor was then designed to incorporate, at an appropriate position, a side chain with appropriate length and functional group(s) which would allow interaction with the receptor. In view of this finding, the present inventors filed two Japanese patent applications on Aug. 23, 1999 (Application A) and Oct. 22, 1999 (Application B).

As a result of further research efforts directed to the structural analysis of androgen receptor, the present inventors found that a compound expected to be a pure antagonist against androgen receptor could be designed by preventing the folding of helix 12 in the androgen receptor. This finding led to the completion of the invention.

In a first aspect, the present invention provides a compound of general formula (I):

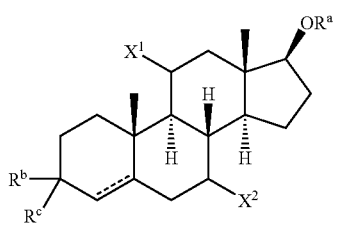
(I)

wherein $X^1$ and $X^2$ independently represent a hydrogen atom or a group of general formula (II):

-Ar-A-G-E    (II), $R^a$ represents a hydrogen atom or a protecting group for a hydroxyl group, $R^b$ and $R^c$ form an optionally protected —(C=O)— together with the 3-position carbon atom attached to $R^b$ and $R^c$, and the broken line forms a single bond or a double bond together with the solid line, wherein Ar represents a single bond or an aromatic hydrocarbon group, A represents a single bond, a methylene group or —O—, G represents a single bond, an optionally substituted linear or branched $C_1$–$C_{30}$ alkylene group, an optionally substituted linear or branched $C_2$–$C_{30}$ alkenylene group, or an optionally substituted linear or branched $C_2$–$C_{30}$ alkynylene group, and E represents a group selected from the following formulae $E^1$ to $E^{10}$:

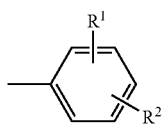
$E^1$

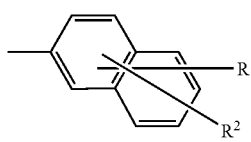
$E^2$

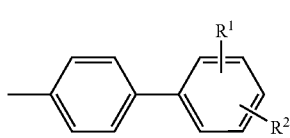
$E^3$

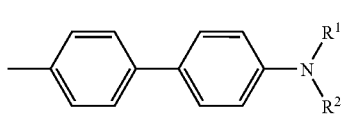
$E^4$

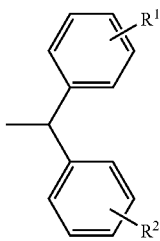
$E^5$

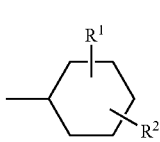
$E^6$

$E^7$

$E^8$

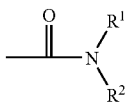
$E^9$

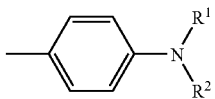
$E^{10}$ wherein $R^1$ and $R^2$, which are the same or different, each represent a group of general formula (III):

-J-G²-Q-Z    (III)

[wherein J represents a single bond, a methylene group or —O—, $G^2$ represents a single bond, an optionally substituted linear or branched $C_1$–$C_{10}$ alkylene group, an optionally substituted linear or branched $C_2$–$C_{10}$ alkenylene group, or an optionally substituted linear or branched $C_2$–$C_{10}$ alkynylene group, Q represents a single bond or a group selected from the following formulae $Q^1$ to $Q^{10}$:

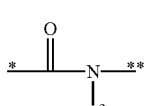
$Q^1$

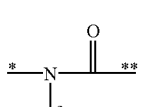
$Q^2$

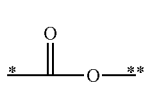
$Q^3$

-continued

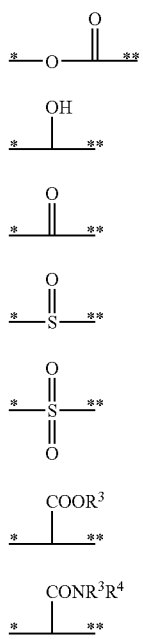

(wherein $R^3$ and $R^4$, which are the same or different, each represent a hydrogen atom or a linear or branched $C_1$–$C_{10}$ lower alkyl group, the bond marked with * is linked to $G^2$, and the bond marked with ** is linked to Z), and Z represents a hydrogen atom, a linear or branched $C_1$–$C_{10}$ alkyl group which may be substituted with a halogen atom, a linear or branched $C_2$–$C_{10}$ alkenyl group which may be substituted with a halogen atom, a linear or branched $C_2$–$C_{10}$ alkynyl group which may be substituted with a halogen atom, or a group of general formula (IV):

(wherein $R^d$ represents a hydrogen atom or a protecting group for a hydroxyl group)], provided that $X^1$ and $X^2$ do not simultaneously represent a hydrogen atom, and Z is not a hydrogen atom when J, $G^2$ and Q simultaneously represent a single bond, or a pharmaceutically acceptable salt of the compound or a prodrug thereof.

In a second aspect, the present invention provides a substance serving as an antagonist against androgen receptor and substantially free of agonistic effects or a pharmaceutically acceptable salt of the substance or a prodrug thereof.

In a third aspect, the present invention provides a pharmaceutical composition comprising a compound of general formula (I) as well as a pharmaceutical composition comprising a substance serving as an antagonist against androgen receptor and substantially free of agonistic effects.

In a fourth aspect, the present invention provides an anti-androgen agent comprising, as an active ingredient, a compound whose molecular structure substantially prevents the folding of helix 12 in the androgen receptor or a pharmaceutically acceptable salt of the compound or a prodrug thereof.

Also, the present invention provides a compound of general formula (I):

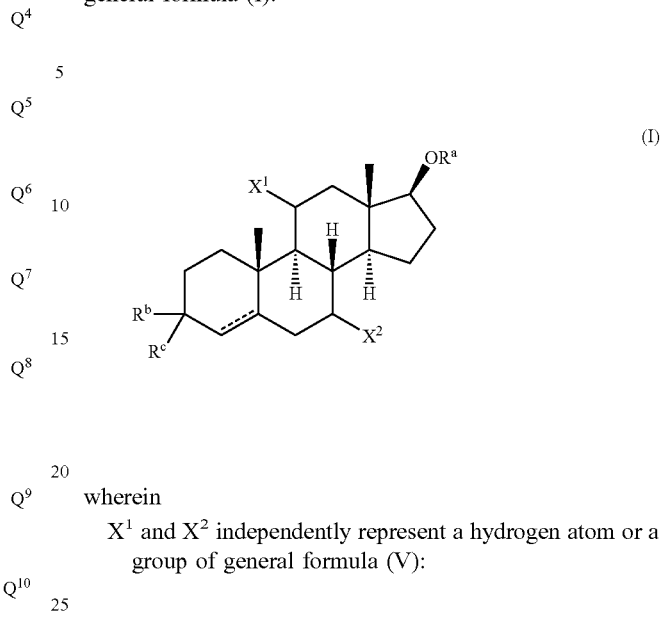

wherein $X^1$ and $X^2$ independently represent a hydrogen atom or a group of general formula (V):

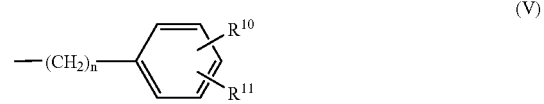

[wherein n represents an integer of 1 to 10, $R^{10}$ represents a hydroxyl group, an alkoxy group or an alkoxycarbonyl group, and $R^{11}$ represents an alkoxy group, an alkoxycarbonyl group or a group of general formula (VI):

(wherein q represents an integer of 1 to 10, and $R^{12}$ represents a hydroxyl group or an alkylamino group)], $R^a$ represents a hydrogen atom or a protecting group for a hydroxyl group, $R^b$ and $R^c$ form an optionally protected —(C=O)— together with the 3-position carbon atom attached to $R^b$ and $R^c$, and the broken line forms a single bond or a double bond together with the solid line, provided that $X^1$ and $X^2$ do not simultaneously represent a hydrogen atom, or a pharmaceutically acceptable salt of the compound or a prodrug thereof.

In addition, the present invention provides a compound of general formula (VII):

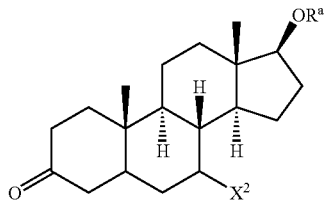

(VII)

wherein

X² represents a group of general formula (V):

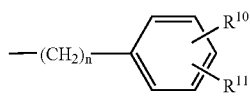

(V)

[wherein n represents an integer of 1 to 10, R¹⁰ represents a hydroxyl group, an alkoxy group or an alkoxycarbonyl group, and R¹¹ represents an alkoxy group, an alkoxycarbonyl group or a group of general formula (VI):

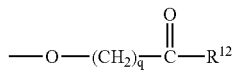

(VI)

(wherein q represents an integer of 1 to 10, and R¹² represents a hydroxyl group or an alkylamino group)], and R$^a$ represents a hydrogen atom or a protecting group for a hydroxyl group, or a pharmaceutically acceptable salt of the compound or a prodrug thereof.

Further, the present invention provides a compound of general formula (VII):

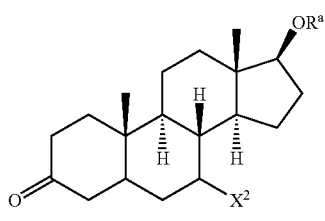

(VII)

wherein

X² represents a group of general formula (VIII):

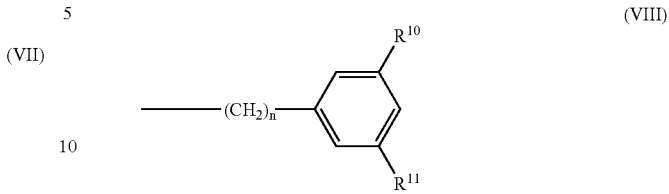

(VIII)

[wherein n represents an integer of 1 to 10, R¹⁰ represents a hydroxyl group, an alkoxy group or an alkoxycarbonyl group, and R¹¹ represents an alkoxy group, an alkoxycarbonyl group or a group of general formula (VI):

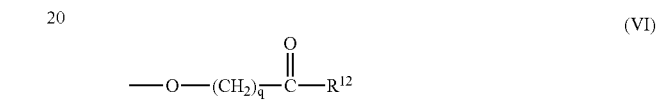

(VI)

(wherein q represents an integer of 1 to 10, and R¹² represents a hydroxyl group or an alkylamino group)], and R$^a$ represents a hydrogen atom or a protecting group for a hydroxyl group, or a pharmaceutically acceptable salt of the compound or a prodrug thereof.

Furthermore, the present invention provides a compound of general formula (I):

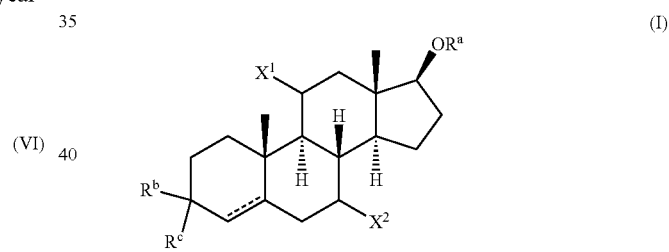

(I)

wherein

X¹ and X² independently represent a hydrogen atom or a group of general formula (V):

(V)

[wherein n represents an integer of 1 to 10, R¹⁰ represents a hydroxyl group, and R¹¹ represents a group of general formula (VI):

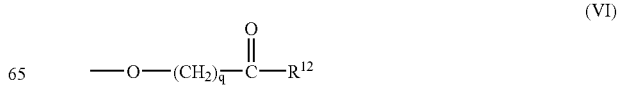

(VI)

(wherein q represents an integer of 1 to 10, and $R^{12}$ represents a hydroxyl group or an alkylamino group)], $R^a$ represents a hydrogen atom or a protecting group for a hydroxyl group, $R^b$ and $R^c$ form an optionally protected —(C=O)— together with the 3-position carbon atom attached to $R^b$ and $R^c$, and, the broken line forms a single bond or a double bond together with the solid line, provided that $X^1$ and $X^2$ do not simultaneously represent a hydrogen atom, or a pharmaceutically acceptable salt of the compound or a prodrug thereof.

Furthermore, the present invention provides a compound of general formula (VII):

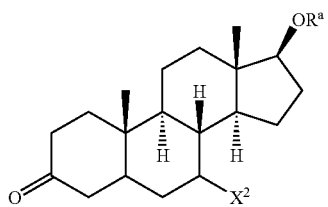
(VII)

wherein
$X^2$ represents a group of general formula (V):

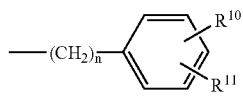
(V)

[wherein n represents an integer of 1 to 10, $R^{10}$ represents a hydroxyl group, and $R^{11}$ represents a group of general formula (VI):

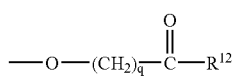
(VI)

(wherein q represents an integer of 1 to 10, and $R^{12}$ represents a hydroxyl group or an alkylamino group)], and $R^a$ represents a hydrogen atom or a protecting group for a hydroxyl group, or a pharmaceutically acceptable salt of the compound or a prodrug thereof.

Furthermore, the present invention provides a compound of general formula (VII):

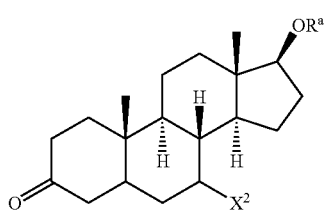
(VII)

wherein
$X^2$ represents a group of general formula (VIII):

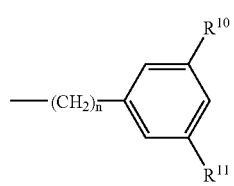
(VIII)

[wherein n represents an integer of 1 to 10, $R^{10}$ represents a hydroxyl group, and $R^{11}$ represents a group of general formula (VI):

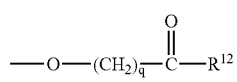
(VI)

(wherein q represents an integer of 1 to 10, and $R^{12}$ represents a hydroxyl group or an alkylamino group)], and $R^a$ represents a hydrogen atom or a protecting group for a hydroxyl group, or a pharmaceutically acceptable salt of the compound or a prodrug thereof.

Also, the present invention provides a pharmaceutical composition comprising, as an active ingredient, a compound of general formula (I) or (VII) or a pharmaceutically acceptable salt of the compound or a prodrug thereof.

In addition, the present invention provides an anti-androgen agent comprising, as an active ingredient, a compound of general formula (I) or (VII) or a pharmaceutically acceptable salt of the compound or a prodrug thereof.

Further, the present invention provides a prophylactic or therapeutic agent for a disease selected from the group consisting of prostate cancer, benign prostatic hyperplasia, male pattern alopecia, precocious puberty, acne vulgaris, seborrhea and hypertrichosis, which comprises, as an active ingredient, a compound of general formula (I) or (VII) or a pharmaceutically acceptable salt of the compound or a prodrug thereof.

BEST MODE FOR CARRYING OUT THE INVENTION

Figure 1:
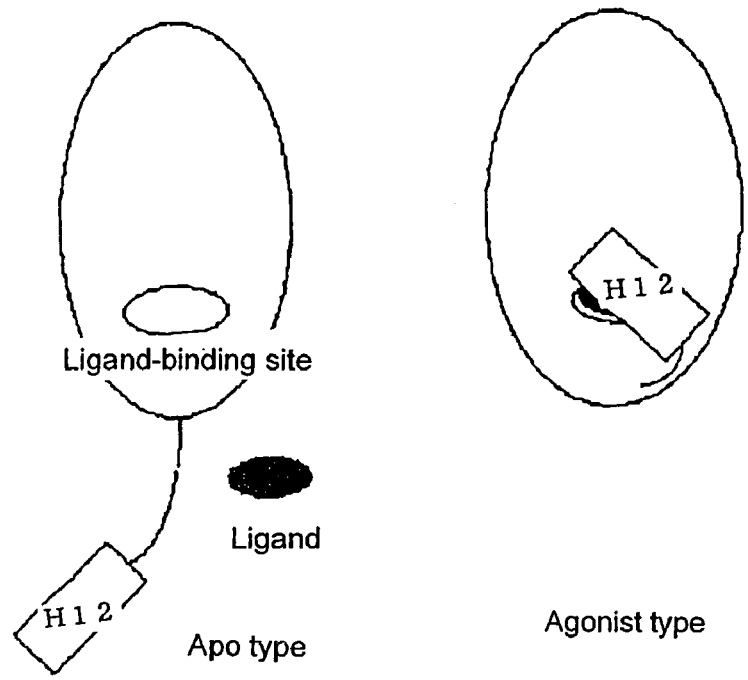
FIG. 1 is a schematic view showing the modes of binding of nuclear receptors: apo type, agonist type, antagonist type, and pure antagonist type (from the left in the figure). In the figure, H12 represents the structure of helix 12.
Figure 1:
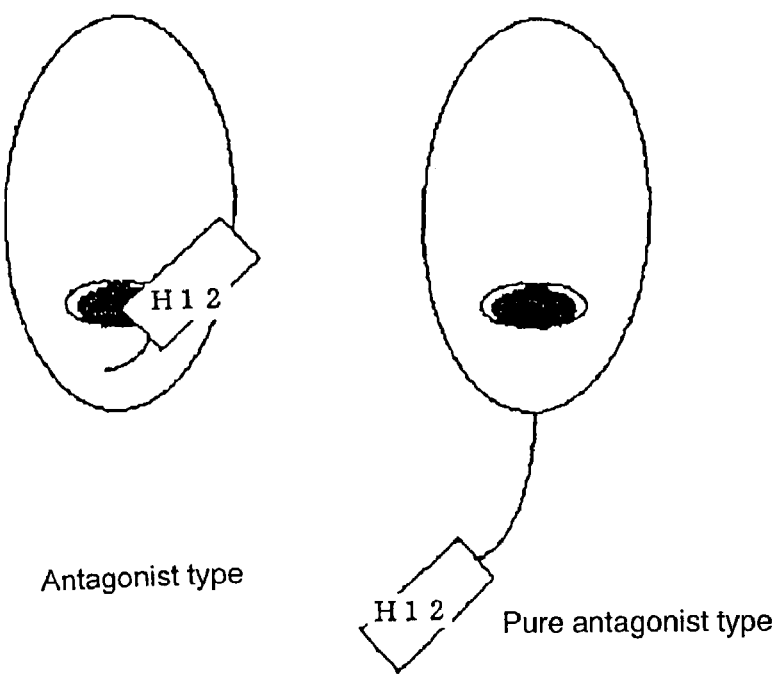

Examples of a linear or branched $C_1$–$C_3$ alkyl group as used herein include methyl, ethyl, n-propyl and i-propyl.

Examples of a linear or branched $C_1$–$C_6$ alkyl group include methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl and n-hexyl.

As used herein, "position ω" refers to another terminal position rather than position 1 on a divalent group. For example, position ω corresponds to position 6 in a hexane-1,6-diyl group.

As used herein, "a single bond" refers to a state where a single bond is directly formed between the neighboring groups, rather than any group is present between them. For example, in a case where Ar is a single bond in a group of general formula (II), a single bond is directly formed between A and positions 7 and/or 11 on the steroid ring in a compound of general formula (I).

As used herein, "the broken line forms a single bond or a double bond together with the solid line" means that a single bond or a double bond is formed between points where the broken line is found, for example, between positions 4 and 5 on the steroid ring in a compound of general formula (I).

As defined in general formula (I), $X^1$ and $X^2$ independently represent a hydrogen atom or a group of general formula (II):

-Ar-A-G-E  (II)

[wherein Ar represents a single bond or an aromatic hydrocarbon group, A represents a single bond, a methylene group or —O—, G represents a single bond, an optionally substituted linear or branched $C_1$–$C_{30}$ alkylene group, an optionally substituted linear or branched $C_2$–$C_{30}$ alkenylene group, or an optionally substituted linear or branched $C_2$–$C_{30}$ alkynylene group, and E represents a group selected from the following formulae $E^1$ to $E^{10}$:

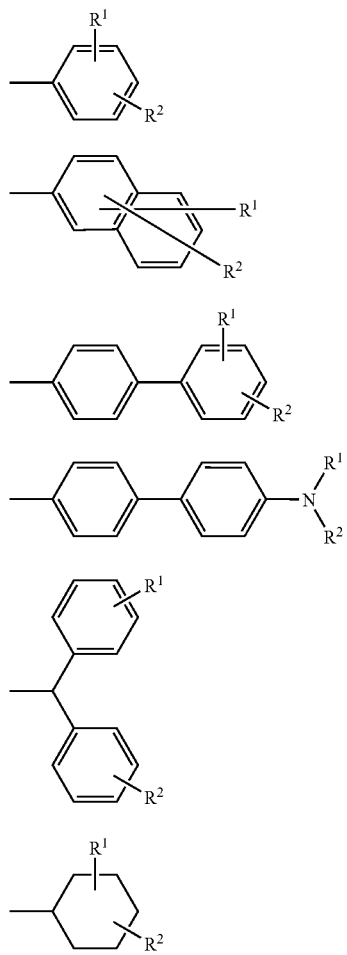

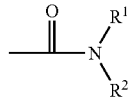

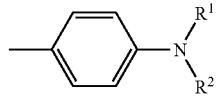

(wherein $R^1$ and $R^2$ are as defined above)]. Preferably, $X^1$ represents -Ar-A-G-E (wherein Ar, A, G and E are as defined above) and $X^2$ represents a hydrogen atom, or $X^1$ represents a hydrogen atom and $X^2$ represents -Ar-A-G-E (wherein Ar, A, G and E are as defined above). More preferably, $X^2$ represents -Ar-A-G-E (wherein Ar, A, G and E are as defined above) and $X^1$ represents a hydrogen atom. Further, $X^1$ preferably takes β-configuration at position 11 on the steroid ring and $X^2$ preferably takes α-configuration at position 7, provided that $X^1$ and $X^2$ do not simultaneously represent a hydrogen atom.

$R^a$ represents a hydrogen atom or a protecting group for a hydroxyl group, and preferably represents a hydrogen atom. Examples of a protecting group for a hydroxyl group include acyl groups such as formyl, acetyl, propionyl, butyryl, isobutyryl, valeryl, isovaleryl, pivaloyl, caproyl, trifluoroacetyl and benzoyl, alkoxycarbonyl groups such as methoxycarbonyl, ethoxycarbonyl, propoxycarbonyl, isopropoxycarbonyl, allyloxycarbonyl, benzyloxycarbonyl and phenoxycarbonyl, substituted silyl groups such as trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl and t-butylmethoxyphenylsilyl, substituted methyl groups such as methoxymethyl, methoxyethoxymethyl, methylthiomethyl, t-butylthiomethyl, β-trichloroethyloxymethyl, trimethylsilylethoxymethyl, p-methoxybenzyloxymethyl and p-chlorobenzyloxymethyl, 2-oxacycloalkyl groups such as tetrahydrofuranyl and tetrahydropyranyl, and aralkyl groups such as benzyl. Above all, preferred are substituted silyl groups such as trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl and t-butylmethoxyphenylsilyl, and substituted methyl groups such as methoxymethyl, methoxyethoxymethyl, methylthiomethyl, t-butylthiomethyl, β-trichloroethyloxymethyl, trimethylsilylethoxymethyl, p-methoxybenzyloxymethyl and p-chlorobenzyloxymethyl. Particularly preferred are t-butyldimethylsilyl and methoxymethyl.

$R^b$ and $R^c$ form an optionally protected —(C=O)— together with the 3-position carbon atom attached to $R^b$ and $R^c$, and preferably form —(C=O)—. Examples of a protected —(C=O)— include noncyclic acetals or ketals such as dimethoxymethylene, bis(2,2,2-trichloroethyloxy)methylene, dibenzylmethylene, bis(2-nitrobenzyloxy)methylene, bis(acetyloxy)methylene, bis(methylthio)methylene, bis(ethylthio)methylene, bis(propylthio)methylene, bis(butylthio)methylene, bis(phenylthio)methylene, bis(benzylthio)methylene, bis(acetylthio)methylene, trimethylsilyloxymethylthiomethylene, trimethylsilyloxyethylthiomethylene, trimethylsilyloxyphenylthiomethylene, methyloxymethylthiomethylene, methyloxyphenylthiomethylene, methyloxy-2-(methylthio)ethylthiomethylene, bis(methylselenenyl)methylene and bis(phenylselenenyl)methylene, and cyclic acetals or ketals such as 1,3-dioxane, 5,5-dibromo-1,3-dioxane, 5-(2-pyridyl)-1,3-dioxane, 1,3-dioxolane, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, 1,5-dihydro-3H-2,4-benzodioxepine, 1,3-dithiane, 1,3-dithiolane, 1,5-dihydro-3H-2,4-benzodithiepine and 1,3-oxathiolane. Preferred are 1,3-dioxane, 1,3-dioxolane and 1,3-dithiane, and particularly preferred is 1,3-dioxolane.

The broken line forms a single bond or a double bond together with the solid line. More specifically, a bond between positions 4 and 5 on the steroid ring may be a single bond or a double bond, preferably a single bond. In a case where the broken line forms a single bond together with the solid line, the hydrogen atom at position 5 on the steroid ring preferably takes α-configuration.

In a group of general formula (II), Ar represents a single bond or an aromatic hydrocarbon group, and preferably represents a single bond.

Examples of an aromatic hydrocarbon ring in the aromatic hydrocarbon group as Ar include a benzene ring, a naphthalene ring, an anthracene ring, a naphthacene ring, a pentacene ring, a hexacene ring, a phenanthrene ring, a triphenylene ring, a pyrene ring, a chrysene ring, a picene ring, a perylene ring, a pentaphene ring, a coronene ring, a heptaphene ring, a pyranthrene ring and an ovalene ring, with a benzene ring being preferred. The aromatic hydrocarbon group as Ar refers to a group having two binding hands at different positions on the aromatic hydrocarbon ring as listed above. Ar preferably represents a p-phenylene group.

A represents a single bond, a methylene group or —O—, and preferably represents a methylene group. In particular, Ar and A are more preferably a single bond and a methylene group, respectively.

In a case where Ar is an aromatic hydrocarbon group, A is preferably —O—.

G represents a single bond, an optionally substituted linear or branched $C_1$–$C_{30}$ alkylene group, an optionally substituted linear or branched $C_2$–$C_{30}$ alkenylene group, or an optionally substituted linear or branched $C_2$–$C_{30}$ alkynylene group. Examples of a substituent on the optionally substituted linear or branched $C_1$–$C_{30}$ alkylene group, the optionally substituted linear or branched $C_2$–$C_{30}$ alkenylene group and the optionally substituted linear or branched $C_2$–$C_{30}$ alkynylene group as G include —$(CH_2)_m$—$COOR^{7a}$, —$(CH_2)_p$—$CONR^{8a}R^{9a}$, —$NR^{8b}R^{9b}$, a hydroxyl group and an oxo group, wherein m and p independently represent 0 or 1, $R^{7a}$ represents a hydrogen atom or a linear or branched $C_1$–$C_6$ alkyl group, and $R^{8a}$, $R^{9a}$, $R^{8b}$ and $R^{9b}$ each independently represent a hydrogen atom or a linear or branched $C_1$–$C_3$ alkyl group. The substituent is preferably absent or a hydroxyl group, more preferably absent. In a case where G is substituted, the number of substituents on G is 1 to 4, preferably 1.

Examples of a linear or branched $C_1$–$C_{30}$ alkylene group in the optionally substituted linear or branched $C_1$–$C_{30}$ alkylene group as G include:

linear alkylene groups such as methylene, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl, octadecane-1,18-diyl, nonadecane-1,19-diyl, icosane-1,20-diyl, henicosane-1,21-diyl, docosane-1,22-diyl, tricosane-1,23-diyl, tetracosane-1,24-diyl, pentacosane-1,25-diyl, hexacosane-1,26-diyl, heptacosane-1,27-diyl, octacosane-1,28-diyl, nonacosane-1,29-diyl and triacontane-1,30-diyl; and branched alkylene groups such as 2-methylpropane-1,3-diyl, 2-methylbutane-1,4-diyl, 3-methylbutane-1,4-diyl, 2,3-dimethylbutane-1,4-diyl, 2-methylpentane-1,5-diyl, 3-methylpentane-1,5-diyl, 4-methylpentane-1,5-diyl, 2,3-dimethylpentane-1,5-diyl, 2,4-dimethylpentane-1,5-diyl, 3,3-dimethylpentane-1,5-diyl, 3,4-dimethylpentane-1,5-diyl, 2,3,4-trimethylpentane-1,5-diyl, 3-ethylpentane-1,5-diyl, 3-ethyl-2-methylpentane-1,5-diyl, 3-ethyl-4-methylpentane-1,5-diyl, 2,4-dimethyl-3-ethylpentane-1,5-diyl, 2-methylhexane-1,6-diyl, 3-methylhexane-1,6-diyl, 4-methylhexane-1,6-diyl, 5-methylhexane-1,6-diyl, 2,3-dimethylhexane-1,6-diyl, 2,4-dimethylhexane-1,6-diyl, 2,5-dimethylhexane-1,6-diyl, 3,3-dimethylhexane-1,6-diyl, 3,4-dimethylhexane-1,6-diyl, 3,5-dimethylhexane-1,6-diyl, 4,4-dimethylhexane-1,6-diyl, 4,5-dimethylhexane-1,6-diyl, 2,3,3-trimethylhexane-1,6-diyl, 2,3,4-trimethylhexane-1,6-diyl, 2,3,5-trimethylhexane-1,6-diyl, 2,4,4-trimethylhexane-1,6-diyl, 2,4,5-trimethylhexane-1,6-diyl, 3,3,4-trimethylhexane-1,6-diyl, 3,3,5-trimethylhexane-1,6-diyl, 3,4,5-trimethylhexane-1,6-diyl, 4,4,5-trimethylhexane-1,6-diyl, 2,3,4,5-tetramethylhexane-1,6-diyl, 3-ethylhexane-1,6-diyl, 4-ethylhexane-1,6-diyl, 3-ethyl-2-methylhexane-1,6-diyl, 3-ethyl-4-methylhexane-1,6-diyl, 3-ethyl-5-methylhexane-1,6-diyl, 4-ethyl-2-methylhexane-1,6-diyl, 4-ethyl-3-methylhexane-1,6-diyl, 4-ethyl-5-methylhexane-1,6-diyl, 2,4-dimethyl-3-ethylhexane-1,6-diyl, 2,5-dimethyl-3-ethylhexane-1,6-diyl, 4,5-dimethyl-3-ethylhexane-1,6-diyl, 2,3-dimethyl-4-ethylhexane-1,6-diyl, 2,5-dimethyl-4-ethylhexane-1,6-diyl, 3,5-dimethyl-4-ethylhexane-1,6-diyl, 3,4-diethylhexane-1,6-diyl, 2-methylheptane-1,7-diyl, 3-methylheptane-1,7-diyl, 4-methylheptane-1,7-diyl, 5-methylheptane-1,7-diyl, 6-methylheptane-1,7-diyl, 2,3-dimethylheptane-1,7-diyl, 2,4-dimethylheptane-1,7-diyl, 2,5-dimethylheptane-1,7-diyl, 2,6-dimethylheptane-1,7-diyl, 3,3-dimethylheptane-1,7-diyl, 3,4-dimethylheptane-1,7-diyl, 3,5-dimethylheptane-1,7-diyl, 3,6-dimethylheptane-1,7-diyl, 4,4-dimethylheptane-1,7-diyl, 4,5-dimethylheptane-1,7-diyl, 4,6-dimethylheptane-1,7-diyl, 5,5-dimethylheptane-1,7-diyl, 5,6-dimethylheptane-1,7-diyl, 2,3,3-trimethylheptane-1,7-diyl, 2,3,4-trimethylheptane-1,7-diyl, 2,3,5-trimethylheptane-1,7-diyl, 2,3,6-trimethylheptane-1,7-diyl, 2,4,4-trimethylheptane-1,7-diyl, 2,4,5-trimethylheptane-1,7-diyl, 2,4,6-trimethylheptane-1,7-diyl, 2,5,5-trimethylheptane-1,7-diyl, 2,5,6-trimethylheptane-1,7-diyl, 3,3,4-trimethylheptane-1,7-diyl, 3,3,5-trimethylheptane-1,7-diyl, 3,3,6-trimethylheptane-1,7-diyl, 3,4,4-trimethylheptane-1,7-diyl, 3,4,5-trimethylheptane-1,7-diyl, 3,4,6-trimethylheptane-1,7-diyl, 3,5,5-trimethylheptane-1,7-diyl, 3,5,6-trimethylheptane-1,7-diyl, 4,4,5-trimethylheptane-1,7-diyl, 4,4,6-trimethylheptane-1,7-diyl, 4,5,5-trimethylheptane-1,7-diyl, 4,5,6-trimethylheptane-1,7- diyl, 3-ethylheptane-1,7-diyl, 4-ethylheptane-1,7-diyl, 5-ethylheptane-1,7-diyl, 3-ethyl-2-methylheptane-1,7-diyl, 3-ethyl-4-methylheptane-1,7-diyl, 3-ethyl-5-methylheptane-1,7-diyl, 3-ethyl-6-methylheptane-1,7-diyl, 4-ethyl-2-methylheptane-1,7-diyl, 4-ethyl-3-methylheptane-1,7-diyl, 4-ethyl-4-methylheptane-1,7-diyl, 4-ethyl-5-methylheptane-1,7-diyl, 4-ethyl-6-methylheptane-1,7-diyl, 5-ethyl-2-methylheptane-1,7-diyl, 5-ethyl-3-methylheptane-1,7-diyl, 5-ethyl-4-methylheptane-1,7-diyl, 5-ethyl-5-methylheptane-1,7-diyl, 5-ethyl-6-methylheptane-1,7-diyl, 4-n-propylheptane-1,7-diyl, 4-i-propylheptane-1,7-diyl, 2-methyloctane-1,8-diyl, 3-methyloctane-1,8-diyl, 3-methyloctane-1,8-diyl, 4-methyloctane-1,8-diyl, 5-methyloctane-1,8-diyl, 6-methyloctane-1,8-diyl, 7-methyloctane-1,8-diyl, 2,3-dimethyloctane-1,8-diyl, 2,4-dimethyloctane-1,8-diyl, 2,5-dimethyloctane-1,8-diyl, 2,6-dimethyloctane-1,8-diyl, 2,7-dimethyloctane-1,8-diyl, 3,3-dimethyloctane-1,8-diyl, 3,4-dimethyloctane-1,8-diyl, 3,5-dimethyloctane-1,8-diyl, 3,6-dimethyloctane-1,8-diyl, 3,7-dimethyloctane-1,8-diyl, 4,4-dimethyloctane-1,8-diyl, 4,5-dimethyloctane-1,8-diyl, 4,6-dimethyloctane-1,8-diyl, 4,7-dimethyloctane-1,8-diyl, 5,5-dimethyloctane-1,8-diyl, 5,6-dimethyloctane-1,8-diyl, 5,7-dimethyloctane-1,8-diyl, 6,6-dimethyloctane-1,8-diyl, 6,7-dimethyloctane-1,8-diyl, 3-ethyloctane-1,8-diyl, 4-ethyloctane-1,8-diyl, 5-ethyloctane-1,8-diyl, 6-ethyloctane-1,8-diyl, 2-methylnonane-1,9-diyl, 3-methylnonane-1,9-diyl, 4-methylnonane-1,9-diyl, 5-methylnonane-1,9-diyl, 6-methylnonane-1,9-diyl, 7-methylnonane-1,9-diyl, 8-methylnonane-1,9-diyl, 2-methyldecane-1,10-diyl, 3-methyldecane-1,10-diyl, 4-methyldecane-1,10-diyl, 5-methyldecane-1,10-diyl, 6-methyldecane-1,10-diyl, 7-methyldecane-1,10-diyl, 8-methyldecane-1,10-diyl, 4-ethyldecane-1,10-diyl, 5-ethyldecane-1,10-diyl, 6-ethyldecane-1,10-diyl, 7-ethyldecane-1,10-diyl, 5-n-propyldecane-1,10-diyl, 6-n-propyldecane-1,10-diyl, 3-ethyl-2-methyldecane-1,10-diyl, 4-ethyl-2-methyldecane-1,10-diyl, 5-ethyl-2-methyldecane-1,10-diyl, 6-ethyl-2-methyldecane-1,10-diyl, 7-ethyl-2-methyldecane-1,10-diyl, 3-ethyl-3-methyldecane-1,10-diyl, 4-ethyl-3-methyldecane-1,10-diyl, 5-ethyl-3-methyldecane-1,10-diyl, 6-ethyl-3-methyldecane-1,10-diyl, 7-ethyl-3-methyldecane-1,10-diyl, 3-ethyl-4-methyldecane-1,10-diyl, 4-ethyl-4-methyldecane-1,10-diyl, 5-ethyl-4-methyldecane-1,10-diyl, 6-ethyl-4-methyldecane-1,10-diyl, 7-ethyl-4-methyldecane-1,10-diyl, 3-ethyl-5-methyldecane-1,10-diyl, 4-ethyl-5-methyldecane-1,10-diyl, 5-ethyl-5-methyldecane-1,10-diyl, 6-ethyl-5-methyl-decane-1,10-diyl, 7-ethyl-5-methyldecane-1,10-diyl, 2-methylundecane-1,11-diyl, 3-methylundecane-1,11-diyl, 4-methylundecane-1,11-diyl, 5-methylundecane-1,11-diyl, 6-methylundecane-1,11-diyl, 7-methylundecane-1,11-diyl, 8-methylundecane-1,11-diyl, 9-methylundecane-1,11-diyl, 10-methylundecane-1,11-diyl, 3-ethylundecane-1,11-diyl, 4-ethylundecane-1,11-diyl, 5-ethylundecane-1,11-diyl, 6-ethylundecane-1,11-diyl, 7-ethylundecane-1,11-diyl, 8-ethylundecane-1,11-diyl, 9-ethylundecane-1,11-diyl, 2-methyldodecane-1,12-diyl, 3-methyldodecane-1,12-diyl, 4-methyldodecane-1,12-diyl, 5-methyldodecane-1,12-diyl, 6-methyldodecane-1,12-diyl, 7-methyldodecane-1,12-diyl, 8-methyldodecane-1,12-diyl, 9-methyldodecane-1,12-diyl, 10-methyldodecane-1,12-diyl, 11-methyldodecane-1,12-diyl, 3-ethyldodecane-1,12-diyl, 4-ethyldodecane-1,12-diyl, 5-ethyldodecane-1,12-diyl, 6-ethyldodecane-1,12-diyl, 7-ethyldodecane-1,12-diyl, 8-ethyldodecane-1,12-diyl, 9-ethyldodecane-1,12-diyl, 10-ethyldodecane-1,12-diyl, 2-methyltridecane-1,13-diyl, 3-methyltridecane-1,13-diyl, 4-methyltridecane-1,13-diyl, 5-methyltridecane-1,13-diyl, 6-methyltridecane-1,13-diyl, 7-methyltridecane-1,13-diyl, 8-methyltridecane-1,13-diyl, 9-methyltridecane-1,13-diyl, 10-methyltridecane-1,13-diyl, 11-methyltridecane-1,13-diyl, 12-methyltridecane-1,13-diyl, 3-ethyltridecane-1,13-diyl, 4-ethyltridecane-1,13-diyl, 5-ethyltridecane-1,13-diyl, 6-ethyltridecane-1,13-diyl, 7-ethyltridecane-1,13-diyl, 8-ethyltridecane-1,13-diyl, 9-ethyltridecane-1,13-diyl, 10-ethyltridecane-1,13-diyl, 11-ethyltridecane-1,13-diyl, 2-methyltetradecane-1,14-diyl, 3-methyltetradecane-1,14-diyl, 4-methyltetradecane-1,14-diyl, 5-methyltetradecane-1,14-diyl, 6-methyltetradecane-1,14-diyl, 7-methyltetradecane-1,14-diyl, 8-methyltetradecane-1,14-diyl, 9-methyltetradecane-1,14-diyl, 10-methyltetradecane-1,14-diyl, 11-methyltetradecane-1,14-diyl, 12-methyltetradecane-1,14-diyl, 13-methyltetradecane-1,14-diyl, 3-ethyltetradecane-1,14-diyl, 4-ethyltetradecane-1,14-diyl, 5-ethyltetradecane-1,14-diyl, 6-ethyltetradecane-1,14-diyl, 7-ethyltetradecane-1,14-diyl, 8-ethyltetradecane-1,14-diyl, 9-ethyltetradecane-1,14-diyl, 10-ethyltetradecane-1,14-diyl, 11-ethyltetradecane-1,14-diyl, 12-ethyltetradecane-1,14-diyl, 2-methylpentadecane-1,15-diyl, 3-methylpentadecane-1,15-diyl, 4-methylpentadecane-1,15-diyl, 5-methylpentadecane-1,15-diyl, 6-methylpentadecane-1,15-diyl, 7-methylpentadecane-1,15-diyl, 8-methylpentadecane-1,15-diyl, 9-methylpentadecane-1,15-diyl, 10-methylpentadecane-1,15-diyl, 11-methylpentadecane-1,15-diyl, 12-methylpentadecane-1,15-diyl, 13-methylpentadecane-1,15-diyl, 14-methylpentadecane-1,15-diyl, 3-ethylpentadecane-1,15-diyl, 4-ethylpentadecane-1,15-diyl, 5-ethylpentadecane-1,15-diyl, 6-ethylpentadecane-1,15-diyl, 7-ethylpentadecane-1,15-diyl, 8-ethylpentadecane-1,15-diyl, 9-ethylpentadecane-1,15-diyl, 10-ethylpentadecane-1,15-diyl, 11-ethylpentadecane-1,15-diyl, 12-ethylpentadecane-1,15-diyl, 13-ethylpentadecane-1,15-diyl, 2-methylhexadecane-1,16-diyl, 3-methylhexadecane-1,16-diyl, 4-methylhexadecane-1,16-diyl, 5-methylhexadecane-1,16-diyl, 6-methylhexadecane-1,16-diyl, 7-methylhexadecane-1,16-diyl, 8-methylhexadecane-1,16-diyl, 9-methylhexadecane-1,16-diyl, 10-methylhexadecane-1,16-diyl, 11-methylhexadecane-1,16-diyl, 12-methylhexadecane-1,16-diyl, 13-methylhexadecane-1,16-diyl, 14-methylhexadecane-1,16-diyl, 15-methylhexadecane-1,16-diyl, 3-ethylhexadecane-1,16-diyl, 4-ethylhexadecane-1,16-diyl, 5-ethylhexadecane-1,16-diyl, 6-ethylhexadecane-1,16-diyl, 7-ethylhexadecane-1,16-diyl, 8-ethylhexadecane-1,16-diyl, 9-ethylhexadecane-1,16-diyl, 10-ethylhexadecane-1,16-diyl, 11-ethylhexadecane-1,16-diyl, 12-ethylhexadecane-1,16-diyl, 13-ethylhexadecane-1,16-diyl, 14-ethylhexadecane-1,16-diyl, 2-methylheptadecane-1,17-diyl, 3-methylheptadecane-1,17-diyl, 4-methylheptadecane-1,17-diyl, 5-methylheptadecane-1,17-diyl, 6-methylheptadecane-1,17-diyl, 7-methylheptadecane-1,17-diyl, 8-methylheptadecane-1,17-diyl, 9-methylheptadecane-1,17-diyl, 10-methylheptadecane-1,17-diyl, 11-methylheptadecane-1,17-diyl, 12-methylheptadecane-1,17-diyl, 13-methylheptadecane-1,17-diyl, 14-methylheptadecane-1,17-diyl, 15-methylheptadecane-1,17-diyl, 16-methylheptadecane-1,17-diyl, 3-ethylheptadecane-1,17-diyl, 4-ethylheptadecane-1,17-diyl, 5-ethylheptadecane-1,17-diyl, 6-ethylheptadecane-1,17-diyl, 7-ethylheptadecane-1,17-diyl, 8-ethylheptadecane-1,17-diyl, 9-ethylheptadecane-1,17-diyl, 10-ethylheptadecane-1,17-diyl, 11-ethylheptadecane-1,17-diyl, 12-ethylheptadecane-1,17-diyl, 13-ethylheptadecane-1,17-diyl, 14-ethylheptadecane-1,17-diyl, 15-ethylheptadecane-1,17-diyl, 2-methyloctadecane-1,18-diyl, 3-methyloctadecane-1,18-diyl, 4-methyloctadecane-1,18-diyl, 5-methyloctadecane-1,18-diyl, 6-methyloctadecane-1,18-diyl, 7-methyloctadecane-1,18-diyl, 8-methyloctadecane-1,18-diyl, 9-methyloctadecane-1,18-diyl, 10-methyloctadecane-1,18-diyl, 11-methyloctadecane-1,18-diyl, 12-methyloctadecane-1,18-diyl, 13-methyloctadecane-1,18-diyl, 14-methyloctadecane-1,18-diyl, 15-methyloctadecane-1,18-diyl, 16-methyloctadecane-1,18-diyl, 17-methyloctadecane-1,18-diyl, 3-ethyloctadecane-1,18-diyl, 4-ethyloctadecane-1,18-diyl, 5-ethyloctadecane-1,18-diyl, 6-ethyloctadecane-1,18-diyl, 7-ethyloctadecane-1,18-diyl, 8-ethyloctadecane-1,18-diyl, 9-ethyloctadecane-1,18-diyl, 10-ethyloctadecane-1,18-diyl, 11-ethyloctadecane-1,18-diyl, 12-ethyloctadecane-1,18-diyl, 13-ethyloctadecane-1,18-diyl, 14-ethyloctadecane-1,18-diyl, 15-ethyloctadecane-1,18-diyl, 16-ethyloctadecane-1,18-diyl, 2-methylnonadecane-1,19-diyl, 3-methylnonadecane-1,19-diyl, 4-methylnonadecane-1,19-diyl, 5-methylnonadecane-1,19-diyl, 6-methylnonadecane-1,19-diyl, 7-methylnonadecane-1,19-diyl, 8-methylnonadecane-1,19-diyl, 9-methylnonadecane-1,19-diyl, 10-methylnonadecane-1,19-diyl, 11-methylnonadecane-1,19-diyl, 12-methylnonadecane-1,19-diyl, 13-methylnonadecane-1,19-diyl, 14-methylnonadecane-1,19-diyl, 15-methylnonadecane-1,19-diyl, 16-methylnonadecane-1,19-diyl, 17-methylnonadecane-1,19-diyl, 18-methylnonadecane-1,19-diyl, 3-ethylnonadecane-1,19-diyl, 4-ethylnonadecane-1,19-diyl, 5-ethylnonadecane-1,19-diyl, 6-ethylnonadecane-1,19-diyl, 7-ethylnonadecane-1,19-diyl, 8-ethylnonadecane-1,19-diyl, 9-ethylnonadecane-1,19-diyl, 10-ethylnonadecane-1,19-diyl, 11-ethylnonadecane-1,19-diyl, 12-ethylnonadecane-1,19-diyl, 13-ethylnonadecane-1,19-diyl, 14-ethylnonadecane-1,19-diyl, 15-ethylnonadecane-1,19-diyl, 16-ethylnonadecane-1,19-diyl, 17-ethylnonadecane-1,19-diyl, 2-methylicosane-1,20-diyl, 3-methylicosane-1,20-diyl, 4-methylicosane-1,20-diyl, 5-methylicosane-1,20-diyl, 6-methylicosane-1,20-diyl, 7-methylicosane-1,20-diyl, 8-methylicosane-1,20-diyl, 9-methylicosane-1,20-diyl, 10-methylicosane-1,20-diyl, 11-methylicosane-1,20-diyl, 12-methylicosane-1,20-diyl, 13-methylicosane-1,20-diyl, 14-methylicosane-1,20-diyl, 15-methylicosane-1,20-diyl, 16-methylicosane-1,20-diyl, 17-methylicosane-1,20-diyl, 18-methylicosane-1,20-diyl, 19-methylicosane-1,20-diyl, 3-ethylicosane-1,20-diyl, 4-ethylicosane-1,20-diyl, 5-ethylicosane-1,20-diyl, 6-ethylicosane-1,20-diyl, 7-ethylicosane-1,20-diyl, 8-ethylicosane-1,20-diyl, 9-ethylicosane-1,20-diyl, 10-ethylicosane-1,20-diyl, 11-ethylicosane-1,20-diyl, 12-ethylicosane-1,20-diyl, 13-ethylicosane-1,20-diyl, 14-ethylicosane-1,20-diyl, 15-ethylicosane-1,20-diyl, 16-ethylicosane-1,20-diyl, 17-ethylicosane-1,20-diyl, 18-ethylicosane-1,20-diyl, 2-methylhenicosane-1,21-diyl, 3-methylhenicosane-1,21-diyl, 4-methylhenicosane-1,21-diyl, 5-methylhenicosane-1,21-diyl, 6-methylhenicosane-1,21-diyl, 7-methylhenicosane-1,21-diyl, 8-methylhenicosane-1,21-diyl, 9-methylhenicosane-1,21-diyl, 10-methylhenicosane-1,21-diyl, 11-methylhenicosane-1,21-diyl, 12-methylhenicosane-1,21-diyl, 13-methylhenicosane-1,21-diyl, 14-methylhenicosane-1,21-diyl, 15-methylhenicosane-1,21-diyl, 16-methylhenicosane-1,21-diyl, 17-methylhenicosane-1,21-diyl, 18-methylhenicosane-1,21-diyl, 19-methylhenicosane-1,21-diyl, 20-methylhenicosane-1,21-diyl, 3-ethylhenicosane-1,21-diyl, 4-ethylhenicosane-1,21-diyl, 5-ethylhenicosane-1,21-diyl, 6-ethylhenicosane-1,21-diyl, 7-ethylhenicosane-1,21-diyl, 8-ethylhenicosane-1,21-diyl, 9-ethylhenicosane-1,21-diyl, 10-ethylhenicosane-1,21-diyl, 11-ethylhenicosane-1,21-diyl, 12-ethylhenicosane-1,21-diyl, 13-ethylhenicosane-1,21-diyl, 14-ethylhenicosane-1,21-diyl, 15-ethylhenicosane-1,21-diyl, 16-ethylhenicosane-1,21-diyl, 17-ethylhenicosane-1,21-diyl, 18-ethylhenicosane-1,21-diyl, 19-ethylhenicosane-1,21-diyl, 2-methyldocosane-1,22-diyl, 3-methyldocosane-1,22-diyl, 4-methyldocosane-1,22-diyl, 5-methyldocosane-1,22-diyl, 6-methyldocosane-1,22-diyl, 7-methyldocosane-1,22-diyl, 8-methyldocosane-1,22-diyl, 9-methyldocosane-1,22-diyl, 10-methyldocosane-1,22-diyl, 11-methyldocosane-1,22-diyl, 12-methyldocosane-1,22-diyl, 13-methyldocosane-1,22-diyl, 14-methyldocosane-1,22-diyl, 15-methyldocosane-1,22-diyl, 16-methyldocosane-1,22-diyl, 17-methyldocosane-1,22-diyl, 18-methyldocosane-1,22-diyl, 19-methyldocosane-1,22-diyl, 20-methyldocosane-1,22-diyl, 21-methyldocosane-1,22-diyl, 3-ethyldocosane-1,22-diyl, 4-ethyldocosane-1,22-diyl, 5-ethyldocosane-1,22-diyl, 6-ethyldocosane-1,22-diyl, 7-ethyldocosane-1,22-diyl, 8-ethyldocosane-1,22-diyl, 9-ethyldocosane-1,22-diyl, 10-ethyldocosane-1,22-diyl, 11-ethyldocosane-1,22-diyl, 12-ethyldocosane-1,22-diyl, 13-ethyldocosane-1,22-diyl, 14-ethyldocosane-1,22-diyl, 15-ethyldocosane-1,22-diyl, 16-ethyldocosane-1,22-diyl, 17-ethyldocosane-1,22-diyl, 18-ethyldocosane-1,22-diyl, 19-ethyldocosane-1,22-diyl, 20-ethyldocosane-1,22-diyl, 2-methyltricosane-1,23-diyl, 3-methyltricosane-1,23-diyl, 4-methyltricosane-1,23-diyl, 5-methyltricosane-1,23-diyl, 6-methyltricosane-1,23-diyl, 7-methyltricosane-1,23-diyl, 8-methyltricosane-1,23-diyl, 9-methyltricosane-1,23-diyl, 10-methyltricosane-1,23-diyl, 11-methyltricosane-1,23-diyl, 12-methyltricosane-1,23-diyl, 13-methyltricosane-1,23-diyl, 14-methyltricosane-1,23-diyl, 15-methyltricosane-1,23-diyl, 16-methyltricosane-1,23-diyl, 17-methyltricosane-1,23-diyl, 18-methyltricosane-1,23-diyl, 19-methyltricosane-1,23-diyl, 20-methyltricosane-1,23-diyl, 21-methyltricosane-1,23-diyl, 22-methyltricosane-1,23-diyl, 3-ethyltricosane-1,23-diyl, 4-ethyltricosane-1,23-diyl, 5-ethyltricosane-1,23-diyl, 6-ethyltricosane-1,23-diyl, 7-ethyltricosane-1,23-diyl, 8-ethyltricosane-1,23-diyl, 9-ethyltricosane-1,23-diyl, 10-ethyltricosane-1,23-diyl, 11-ethyltricosane-1,23-diyl, 12-ethyltricosane-1,23-diyl, 13-ethyltricosane-1,23-diyl, 14-ethyltricosane-1,23-diyl, 15-ethyltricosane-1,23-diyl, 16-ethyltricosane-1,23-diyl, 17-ethyltricosane-1,23-diyl, 18-ethyltricosane-1,23-diyl, 19-ethyltricosane-1,23-diyl, 20-ethyltricosane-1,23-diyl, 21-ethyltricosane-1,23-diyl, 2-methyltetracosane-1,24-diyl, 3-methyltetracosane-1,24-diyl, 4-methyltetracosane-1,24-diyl, 5-methyltetracosane-1,24-diyl, 6-methyltetracosane-1,24-diyl, 7-methyltetracosane-1,24-diyl, 8-methyltetracosane-1,24-diyl, 9-methyltetracosane-1,24-diyl, 10-methyltetracosane-1,24-diyl, 11-methyltetracosane-1,24-diyl, 12-methyltetracosane-1,24-diyl, 13-methyltetracosane-1,24-diyl, 14-methyltetracosane-1,24-diyl, 15-methyltetracosane-1,24-diyl, 16-methyltetracosane-1,24-diyl, 17-methyltetracosane-1,24-diyl, 18-methyltetracosane-1,24-diyl, 19-methyltetracosane-1,24-diyl, 20-methyltetracosane-1,24-diyl, 21-methyltetracosane-1,24-diyl, 22-methyltetracosane-1,24-diyl, 23-methyltetracosane-1,24-diyl, 3-ethyltetracosane-1,24-diyl, 4-ethyltetracosane-1,24-diyl, 5-ethyltetracosane-1,24-diyl, 6-ethyltetracosane-1,24-diyl, 7-ethyltetracosane-1,24-diyl, 8-ethyltetracosane-1,24-diyl, 9-ethyltetracosane-1,24-diyl, 10-ethyltetracosane-1,24-diyl, 11-ethyltetracosane-1,24-diyl, 12-ethyltetracosane-1,24-diyl, 13-ethyltetracosane-1,24-diyl, 14-ethyltetracosane-1,24-diyl, 15-ethyltetracosane-1,24-diyl, 16-ethyltetracosane-1,24-diyl, 17-ethyltetracosane-1,24-diyl, 18-ethyltetracosane-1,24-diyl, 19-ethyltetracosane-1,24-diyl, 20-ethyltetracosane-1,24-diyl, 21-ethyltetracosane-1,24-diyl, 22-ethyltetracosane-1,24-diyl, 2-methylpentacosane-1,25-diyl, 3-methylpentacosane-1,25-diyl, 4-methylpentacosane-1,25-diyl, 5-methylpentacosane-1,25-diyl, 6-methylpentacosane-1,25-diyl, 7-methylpentacosane-1,25-diyl, 8-methylpentacosane-1,25-diyl, 9-methylpentacosane-1,25-diyl, 10-methylpentacosane-1,25-diyl, 11-methylpentacosane-1,25-diyl, 12-methylpentacosane-1,25-diyl, 13-methylpentacosane-1,25-diyl, 14-methylpentacosane-1,25-diyl, 15-methylpentacosane-1,25-diyl, 16-methylpentacosane-1,25-diyl, 17-methylpentacosane-1,25-diyl, 18-methylpentacosane-1,25-diyl, 19-methylpentacosane-1,25-diyl, 20-methylpentacosane-1,25-diyl, 21-methylpentacosane-1,25-diyl, 22-methylpentacosane-1,25-diyl, 23-methylpentacosane-1,25-diyl, 24-methylpentacosane-1,25-diyl, 3-ethylpentacosane-1,25-diyl, 4-ethylpentacosane-1,25-diyl, 5-ethylpentacosane-1,25-diyl, 6-ethylpentacosane-1,25-diyl, 7-ethylpentacosane-1,25-diyl, 8-ethylpentacosane-1,25-diyl, 9-ethylpentacosane-1,25-diyl, 10-ethylpentacosane-1,25-diyl, 11-ethylpentacosane-1,25-diyl, 12-ethylpentacosane-1,25-diyl, 13-ethylpentacosane-1,25-diyl, 14-ethylpentacosane-1,25-diyl, 15-ethylpentacosane-1,25-diyl, 16-ethylpentacosane-1,25-diyl, 17-ethylpentacosane-1,25-diyl, 18-ethylpentacosane-1,25-diyl, 19-ethylpentacosane-1,25-diyl, 20-ethylpentacosane-1,25-diyl, 21-ethylpentacosane-1,25-diyl, 22-ethylpentacosane-1,25-diyl, 23-ethylpentacosane-1,25-diyl, 2-methylhexacosane-1,26-diyl, 3-methylhexacosane-1,26-diyl, 4-methylhexacosane-1,26-diyl, 5-methylhexacosane-1,26-diyl, 6-methylhexacosane-1,26-diyl, 7-methylhexacosane-1,26-diyl, 8-methylhexacosane-1,26-diyl, 9-methylhexacosane-1,26-diyl, 10-methylhexacosane-1,26-diyl, 11-methylhexacosane-1,26-diyl, 12-methylhexacosane-1,26-diyl, 13-methylhexacosane-1,26-diyl, 14-methylhexacosane-1,26-diyl, 15-methylhexacosane-1,26-diyl, 16-methylhexacosane-1,26-diyl, 17-methylhexacosane-1,26-diyl, 18-methylhexacosane-1,26-diyl, 19-methylhexacosane-1,26-diyl, 20-methylhexacosane-1,26-diyl, 21-methylhexacosane-1,26-diyl, 22-methylhexacosane-1,26-diyl, 23-methylhexacosane-1,26-diyl, 24-methylhexacosane-1,26-diyl, 25-methylhexacosane-1,26-diyl, 3-ethylhexacosane-1,26-diyl, 4-ethylhexacosane-1,26-diyl, 5-ethylhexacosane-1,26-diyl, 6-ethylhexacosane-1,26-diyl, 7-ethylhexacosane-1,26-diyl, 8-ethylhexacosane-1,26-diyl, 9-ethylhexacosane-1,26-diyl, 10-ethylhexacosane-1,26-diyl, 11-ethylhexacosane-1,26-diyl, 12-ethylhexacosane-1,26-diyl, 13-ethylhexacosane-1,26-diyl, 14-ethylhexacosane-1,26-diyl, 15-ethylhexacosane-1,26-diyl, 16-ethylhexacosane-1,26-diyl, 17-ethylhexacosane-1,26-diyl, 18-ethylhexacosane-1,26-diyl, 19-ethylhexacosane-1,26-diyl, 20-ethylhexacosane-1,26-diyl, 21-ethylhexacosane-1,26-diyl, 22-ethylhexacosane-1,26-diyl, 23-ethylhexacosane-1,26-diyl, 24-ethylhexacosane-1,26-diyl, 2-methylheptacosane-1,27-diyl, 3-methylheptacosane-1,27-diyl, 4-methylheptacosane-1,27-diyl, 5-methylheptacosane-1,27-diyl, 6-methylheptacosane-1,27-diyl, 7-methylheptacosane-1,27-diyl, 8-methylheptacosane-1,27-diyl, 9-methylheptacosane-1,27-diyl, 10-methylheptacosane-1,27-diyl, 11-methylheptacosane-1,27-diyl, 12-methylheptacosane-1,27-diyl, 13-methylheptacosane-1,27-diyl, 14-methylheptacosane-1,27-diyl, 15-methylheptacosane-1,27-diyl, 16-methylheptacosane-1,27-diyl, 17-methylheptacosane-1,27-diyl, 18-methylheptacosane-1,27-diyl, 19-methylheptacosane-1,27-diyl, 20-methylheptacosane-1,27-diyl, 21-methylheptacosane-1,27-diyl, 22-methylheptacosane-1,27-diyl, 23-methylheptacosane-1,27-diyl, 24-methylheptacosane-1,27-diyl, 25-methylheptacosane-1,27-diyl, 26-methylheptacosane-1,27-diyl, 3-ethylheptacosane-1,27-diyl, 4-ethylheptacosane-1,27-diyl, 5-ethylheptacosane-1,27-diyl, 6-ethylheptacosane-1,27-diyl, 7-ethylheptacosane-1,27-diyl, 8-ethylheptacosane-1,27-diyl, 9-ethylheptacosane-1,27-diyl, 10-ethylheptacosane-1,27-diyl, 11-ethylheptacosane-1,27-diyl, 12-ethylheptacosane-1,27-diyl, 13-ethylheptacosane-1,27-diyl, 14-ethylheptacosane-1,27-diyl, 15-ethylheptacosane-1,27-diyl, 16-ethylheptacosane-1,27-diyl, 17-ethylheptacosane-1,27-diyl, 18-ethylheptacosane-1,27-diyl, 19-ethylheptacosane-1,27-diyl, 20-ethylheptacosane-1,27-diyl, 21-ethylheptacosane-1,27-diyl, 22-ethylheptacosane-1,27-diyl, 23-ethylheptacosane-1,27-diyl, 24-ethylheptacosane-1,27-diyl, 25-ethylheptacosane-1,27-diyl, 2-methyloctacosane-1,28-diyl, 3-methyloctacosane-1,28-diyl, 4-methyloctacosane-1,28-diyl, 5-methyloctacosane-1,28-diyl, 6-methyloctacosane-1,28-diyl, 7-methyloctacosane-1,28-diyl, 8-methyloctacosane-1,28-diyl, 9-methyloctacosane-1,28-diyl, 10-methyloctacosane-1,28-diyl, 11-methyloctacosane-1,28-diyl, 12-methyloctacosane-1,28-diyl, 13-methyloctacosane-1,28-diyl, 14-methyloctacosane-1,28-diyl, 15-methyloctacosane-1,28-diyl, 16-methyloctacosane-1,28-diyl, 17-methyloctacosane-1,28-diyl, 18-methyloctacosane-1,28-diyl, 19-methyloctacosane-1,28-diyl, 20-methyloctacosane-1,28-diyl, 21-methyloctacosane-1,28-diyl, 22-methyloctacosane-1,28-diyl, 23-methyloctacosane-1,28-diyl, 24-methyloctacosane-1,28-diyl, 25-methyloctacosane-1,28-diyl, 26-methyloctacosane-1,28-diyl, 27-methyloctacosane-1,28-diyl, 3-ethyloctacosane-1,28-diyl, 4-ethyloctacosane-1,28-diyl, 5-ethyloctacosane-1,28-diyl, 6-ethyloctacosane-1,28-diyl, 7-ethyloctacosane-1,28-diyl, 8-ethyloctacosane-1,28-diyl, 9-ethyloctacosane-1,28-diyl, 10-ethyloctacosane-1,28-diyl, 11-methyloctacosane-1,28-diyl, 12-ethyloctacosane-1,28-diyl, 13-ethyloctacosane-1,28-diyl, 14-ethyloctacosane-1,28-diyl, 15-ethyloctacosane-1,28-diyl, 16-ethyloctacosane-1,28-diyl, 17-ethyloctacosane-1,28-diyl, 18-ethyloctacosane-1,28-diyl, 19-ethyloctacosane-1,28-diyl, 20-ethyloctacosane-1,28-diyl, 21-ethyloctacosane-1,28-diyl, 22-ethyloctacosane-1,28-diyl, 23-ethyloctacosane-1,28-diyl, 24-ethyloctacosane-1,28-diyl, 25-ethyloctacosane-1,28-diyl, 26-ethyloctacosane-1,28-diyl, 2-methylnonacosane-1,29-diyl, 3-methylnonacosane-1,29-diyl, 4-methylnonacosane-1,29-diyl, 5-methylnonacosane-1,29-diyl, 6-methylnonacosane-1,29-diyl, 7-methylnonacosane-1,29-diyl, 8-methylnonacosane-1,29-diyl, 9-methylnonacosane-1,29-diyl, 10-methylnonacosane-1,29-diyl, 11-methylnonacosane-1,29-diyl, 12-methylnonacosane-1,29-diyl, 13-methylnonacosane-1,29-diyl, 14-methylnonacosane-1,29-diyl, 15-methylnonacosane-1,29-diyl, 16-methylnonacosane-1,29-diyl, 17-methylnonacosane-1,29-diyl, 18-methylnonacosane-1,29-diyl, 19-methylnonacosane-1,29-diyl, 20-methylnonacosane-1,29-diyl, 21-methylnonacosane-1,29-diyl, 22-methylnonacosane-1,29-diyl, 23-methylnonacosane-1,29-diyl, 24-methylnonacosane-1,29-diyl, 25-methylnonacosane-1,29-diyl, 26-methylnonacosane-1,29-diyl, 27-methylnonacosane-1,29-diyl and 28-methylnonacosane-1,29-diyl.

Examples of a linear or branched $C_2$–$C_{30}$ alkenylene group in the optionally substituted linear or branched $C_2$–$C_{30}$ alkenylene group as G include:

linear alkenylene groups such as ethylene-1,2-diyl, 1-propen-1,3-diyl, 2-propen-1,3-diyl, 1-butene-1,4-diyl, 2-butene-1,4-diyl, 3-butene-1,4-diyl, 1,3-butadiene-1,4-diyl, 2-pentene-1,5-diyl, 3-pentene-1,5-diyl, 2,4-pentadiene-1,5-diyl, 2-hexene-1,6-diyl, 3-hexene-1,6-diyl, 4-hexene-1,6-diyl, 2,4-hexadiene-1,6-diyl, 2-heptene-1,7-diyl, 3-heptene-1,7-diyl, 4-heptene-1,7-diyl, 5-heptene-1,7-diyl, 2,4-heptadiene-1,7-diyl, 2,5-heptadiene-1,7-diyl, 3,5-heptadiene-1,7-diyl, 2-octene-1,8-diyl, 3-octene-1,8-diyl, 4-octene-1,8-diyl, 5-octene-1,8-diyl, 6-octene-1,8-diyl, 2,4-octadiene-1,8-diyl, 2,5-octadiene-1,8-diyl, 2,6-octadiene-1,8-diyl, 2,4,6-octatriene-1,8-diyl, 2-nonene-1,9-diyl, 3-nonene-1,9-diyl, 4-nonene-1,9-diyl, 5-nonene-1,9-diyl, 6-nonene-1,9-diyl, 7-nonene-1,9-diyl, 2-decene-1,10-diyl, 3-decene-1,10-diyl, 4-decene-1,10-diyl, 5-decene-1,10-diyl, 6-decene-1,10-diyl, 7-decene-1,10-diyl, 8-decene-1,10-diyl, 2-undecene-1,11-diyl, 3-undecene-1,11-diyl, 4-undecene-1,11-diyl, 5-undecene-1,11-diyl, 6-undecene-1,11-diyl, 7-undecene-1,11-diyl, 8-undecene-1,11-diyl, 9-undecene-1,11-diyl, 2-dodecene-1,12-diyl, 3-dodecene-1,12-diyl, 4-dodecene-1,12-diyl, 5-dodecene-1,12-diyl, 6-dodecene-1,12-diyl, 7-dodecene-1,12-diyl, 8-dodecene-1,12-diyl, 9-dodecene-1,12-diyl, 10-dodecene-1,12-diyl, 2-tridecene-1,13-diyl, 3-tridecene-1,13-diyl, 4-tridecene-1,13-diyl, 5-tridecene-1,13-diyl, 6-tridecene-1,13-diyl, 7-tridecene-1,13-diyl, 8-tridecene-1,13-diyl, 9-tridecene-1,13-diyl, 10-tridecene-1,13-diyl, 11-tridecene-1,13-diyl, 2-tetradecene-1,14-diyl, 3-tetradecene-1,14-diyl, 4-tetradecene-1,14-diyl, 5-tetradecene-1,14-diyl, 6-tetradecene-1,14-diyl, 7-tetradecene-1,14-diyl, 8-tetradecene-1,14-diyl, 9-tetradecene-1,14-diyl, 10-tetradecene-1,14-diyl, 11-tetradecene-1,14-diyl, 12-tetradecene-1,14-diyl, 2-pentadecene-1,15-diyl, 3-pentadecene-1,15-diyl, 4-pentadecene-1,15-diyl, 5-pentadecene-1,15-diyl, 6-pentadecene-1,15-diyl, 7-pentadecene-1,15-diyl, 8-pentadecene-1,15-diyl, 9-pentadecene-1,15-diyl, 10-pentadecene-1,15-diyl, 11-pentadecene-1,15-diyl, 12-pentadecene-1,15-diyl, 13-pentadecene-1,15-diyl, 2-hexadecene-1,16-diyl, 3-hexadecene-1,16-diyl, 4-hexadecene-1,16-diyl, 5-hexadecene-1,16-diyl, 6-hexadecene-1,16-diyl, 7-hexadecene-1,16-diyl, 8-hexadecene-1,16-diyl, 9-hexadecene-1,16-diyl, 10-hexadecene-1,16-diyl, 11-hexadecene-1,16-diyl, 12-hexadecene-1,16-diyl, 13-hexadecene-1,16-diyl, 14-hexadecene-1,16-diyl, 2-heptadecene-1,17-diyl, 3-heptadecene-1,17-diyl, 4-heptadecene-1,17-diyl, 5-heptadecene-1,17-diyl, 6-heptadecene-1,17-diyl, 7-heptadecene-1,17-diyl, 8-heptadecene-1,17-diyl, 9-heptadecene-1,17-diyl, 10-heptadecene-1,17-diyl, 11-heptadecene-1,17-diyl, 12-heptadecene-1,17-diyl, 13-heptadecene-1,17-diyl, 14-heptadecene-1,17-diyl, 15-heptadecene-1,17-diyl, 2-octadecene-1,18-diyl, 3-octadecene-1,18-diyl, 4-octadecene-1,18-diyl, 5-octadecene-1,18-diyl, 6-octadecene-1,18-diyl, 7-octadecene-1,18-diyl, 8-octadecene-1,18-diyl, 9-octadecene-1,18-diyl, 10-octadecene-1,18-diyl, 11-octadecene-1,18-diyl, 12-octadecene-1,18-diyl, 13-octadecene-1,18-diyl, 14-octadecene-1,18-diyl, 15-octadecene-1,18-diyl, 16-octadecene-1,18-diyl, 2-nonadecene-1,19-diyl, 3-nonadecene-1,19-diyl, 4-nonadecene-1,19-diyl, 5-nonadecene-1,19-diyl, 6-nonadecene-1,19-diyl, 7-nonadecene-1,19-diyl, 8-nonadecene-1,19-diyl, 9-nonadecene-1,19-diyl, 10-nonadecene-1,19-diyl, 11-nonadecene-1,19-diyl, 12-nonadecene-1,19-diyl, 13-nonadecene-1,19-diyl, 14-nonadecene-1,19-diyl, 15-nonadecene-1,19-diyl, 16-nonadecene-1,19-diyl, 17-nonadecene-1,19-diyl, 2-icosene-1,20-diyl, 3-icosene-1,20-diyl, 4-icosene-1,20-diyl, 5-icosene-1,20-diyl, 6-icosene-1,20-diyl, 7-icosene-1,20-diyl, 8-icosene-1,20-diyl, 9-icosene-1,20-diyl, 10-icosene-1,20-diyl, 11-icosene-1,20-diyl, 12-icosene-1,20-diyl, 13-icosene-1,20-diyl, 14-icosene-1,20-diyl, 15-icosene-1,20-diyl, 16-icosene-1,20-diyl, 17-icosene-1,20-diyl, 18-icosene-1,20-diyl, 2-henicosene-1,21-diyl, 3-henicosene-1,21-diyl, 4-henicosene-1,21-diyl, 5-henicosene-1,21-diyl, 6-henicosene-1,21-diyl, 7-henicosene-1,21-diyl, 8-henicosene-1,21-diyl, 9-henicosene-1,21-diyl, 10-henicosene-1,21-diyl, 11-henicosene-1,21-diyl, 12-henicosene-1,21-diyl, 13-henicosene-1,21-diyl, 14-henicosene-1,21-diyl, 15-henicosene-1,21-diyl, 16-henicosene-1,21-diyl, 17-henicosene-1,21-diyl, 18-henicosene-1,21-diyl, 19-henicosene-1,21-diyl, 2-docosene-1,22-diyl, 3-docosene-1,22-diyl, 4-docosene-1,22-diyl, 5-docosene-1,22-diyl, 6-docosene-1,22-diyl, 7-docosene-1,22-diyl, 8-docosene-1,22-diyl, 9-docosene-1,22-diyl, 10-docosene-1,22-diyl, 11-docosene-1,22-diyl, 12-docosene-1,22-diyl, 13-docosene-1,22-diyl, 14-docosene-1,22-diyl, 15-docosene-1,22-diyl, 16-docosene-1,22-diyl, 17-docosene-1,22-diyl, 18-docosene-1,22-diyl, 19-docosene-1,22-diyl, 20-docosene-1,22-diyl, 2-tricosene-1,23-diyl, 3-tricosene-1,23-diyl, 4-tricosene-1,23-diyl, 5-tricosene-1,23-diyl, 6-tricosene-1,23-diyl, 7-tricosene-1,23-diyl, 8-tricosene-1,23-diyl, 9-tricosene-1,23-diyl, 10-tricosene-1,23-diyl, 11-tricosene-1,23-diyl, 12-tricosene-1,23-diyl, 13-tricosene-1,23-diyl, 14-tricosene-1,23-diyl, 15-tricosene-1,23-diyl, 16-tricosene-1,23-diyl, 17-tricosene-1,23-diyl, 18-tricosene-1,23-diyl, 19-tricosene-1,23-diyl, 20-tricosene-1,23-diyl, 21-tricosene-1,23-diyl, 2-tetracosene-1,24-diyl, 3-tetracosene-1,24-diyl, 4-tetracosene-1,24-diyl, 5-tetracosene-1,24-diyl, 6-tetracosene-1,24-diyl, 7-tetracosene-1,24-diyl, 8-tetracosene-1,24-diyl, 9-tetracosene-1,24-diyl, 10-tetracosene-1,24-diyl, 11-tetracosene-1,24-diyl, 12-tetracosene-1,24-diyl, 13-tetracosene-1,24-diyl, 14-tetracosene-1,24-diyl, 15-tetracosene-1,24-diyl, 16-tetracosene-1,24-diyl, 17-tetracosene-1,24-diyl, 18-tetracosene-1,24-diyl, 19-tetracosene-1,24-diyl, 20-tetracosene-1,24-diyl, 21-tetracosene-1,24-diyl, 22-tetracosene-1,24-diyl, 2-pentacosene-1,25-diyl, 3-pentacosene-1,25-diyl, 4-pentacosene-1,25-diyl, 5-pentacosene-1,25-diyl, 6-pentacosene-1,25-diyl, 7-pentacosene-1,25-diyl, 8-pentacosene-1,25-diyl, 9-pentacosene-1,25-diyl, 10-pentacosene-1,25-diyl, 11-pentacosene-1,25-diyl, 12-pentacosene-1,25-diyl, 13-pentacosene-1,25-diyl, 14-pentacosene-1,25-diyl, 15-pentacosene-1,25-diyl, 16-pentacosene-1,25-diyl, 17-pentacosene-1,25-diyl, 18-pentacosene-1,25-diyl, 19-pentacosene-1,25-diyl, 20-pentacosene-1,25-diyl, 21-pentacosene-1,25-diyl, 22-pentacosene-1,25-diyl, 23-pentacosene-1,25-diyl, 2-hexacosene-1,26-diyl, 3-hexacosene-1,26-diyl, 4-hexacosene-1,26-diyl, 5-hexacosene-1,26-diyl, 6-hexacosene-1,26-diyl, 7-hexacosene-1,26-diyl, 8-hexacosene-1,26-diyl, 9-hexacosene-1,26-diyl, 10-hexacosene-1,26-diyl, 11-hexacosene-1,26-diyl, 12-hexacosene-1,26-diyl, 13-hexacosene-1,26-diyl, 14-hexacosene-1,26-diyl, 15-hexacosene-1,26-diyl, 16-hexacosene-1,26-diyl, 17-hexacosene-1,26-diyl, 18-hexacosene-1,26-diyl, 19-hexacosene-1,26-diyl, 20-hexacosene-1,26-diyl, 21-hexacosene-1,26-diyl, 22-hexacosene-1,26-diyl, 23-hexacosene-1,26-diyl, 24-hexacosene-1,26-diyl, 2-heptacosene-1,27-diyl, 3-heptacosene-1,27-diyl, 4-heptacosene-1,27-diyl, 5-heptacosene-1,27-diyl, 6-heptacosene-1,27-diyl, 7-heptacosene-1,27-diyl, 8-heptacosene-1,27-diyl, 9-heptacosene-1,27-diyl, 10-heptacosene-1,27-diyl, 11-heptacosene-1,27-diyl, 12-heptacosene-1,27-diyl, 13-heptacosene-1,27-diyl, 14-heptacosene-1,27-diyl, 15-heptacosene-1,27-diyl, 16-heptacosene-1,27-diyl, 17-heptacosene-1,27-diyl, 18-heptacosene-1,27-diyl, 19-heptacosene-1,27-diyl, 20-heptacosene-1,27-diyl, 21-heptacosene-1,27-diyl, 22-heptacosene-1,27-diyl, 23-heptacosene-1,27-diyl, 24-heptacosene-1,27-diyl, 25-heptacosene-1,27-diyl, 2-octacosene-1,28-diyl, 3-octacosene-1,28-diyl, 4-octacosene-1,28-diyl, 5-octacosene-1,28-diyl, 6-octacosene-1,28-diyl, 7-octacosene-1,28-diyl, 8-octacosene-1,28-diyl, 9-octacosene-1,28-diyl, 10-octacosene-1,28-diyl, 11-octacosene-1,28-diyl, 12-octacosene-1,28-diyl, 13-octacosene-1,28-diyl, 14-octacosene-1,28-diyl, 15-octacosene-1,28-diyl, 16-octacosene-1,28-diyl, 17-octacosene-1,28-diyl, 18-octacosene-1,28-diyl, 19-octacosene-1,28-diyl, 20-octacosene-1,28-diyl, 21-octacosene-1,28-diyl, 22-octacosene-1,28-diyl, 23-octacosene-1,28-diyl, 24-octacosene-1,28-diyl, 25-octacosene-1,28-diyl, 26-octacosene-1,28-diyl, 2-nonacosene-1,29-diyl, 3-nonacosene-1,29-diyl, 4-nonacosene-1,29-diyl, 5-nonacosene-1,29-diyl, 6-nonacosene-1,29-diyl, 7-nonacosene-1,29-diyl, 8-nonacosene-1,29-diyl, 9-nonacosene-1,29-diyl, 10-nonacosene-1,29-diyl, 11-nonacosene-1,29-diyl, 12-nonacosene-1,29-diyl, 13-nonacosene-1,29-diyl, 14-nonacosene-1,29-diyl, 15-nonacosene-1,29-diyl, 16-nonacosene-1,29-diyl, 17-nonacosene-1,29-diyl, 18-nonacosene-1,29-diyl, 19-nonacosene-1,29-diyl, 20-nonacosene-1,29-diyl, 21-nonacosene-1,29-diyl, 22-nonacosene-1,29-diyl, 23-nonacosene-1,29-diyl, 24-nonacosene-1,29-diyl, 25-nonacosene-1,29-diyl, 26-nonacosene-1,29-diyl, 27-nonacosene-1,29-diyl, 2-triacontene-1,30-diyl, 3-triacontene-1,30-diyl, 4-triacontene-1,30-diyl, 5-triacontene-1,30-diyl, 6-triacontene-1,30-diyl, 7-triacontene-1,30-diyl, 8-triacontene-1,30-diyl, 9-triacontene-1,30-diyl, 10-triacontene-1,30-diyl, 11-triacontene-1,30-diyl, 12-triacontene-1,30-diyl, 13-triacontene-1,30-diyl, 14-triacontene-1,30-diyl, 15-triacontene-1,30-diyl, 16-triacontene-1,30-diyl, 17-triacontene-1,30-diyl, 18-triacontene-1,30-diyl, 19-triacontene-1,30-diyl, 20-triacontene-1,30-diyl, 21-triacontene-1,30-diyl, 22-triacontene-1,30-diyl, 23-triacontene-1,30-diyl, 24-triacontene-1,30-diyl, 25-triacontene-1,30-diyl, 26-triacontene-1,30-diyl, 27-triacontene-1,30-diyl and 28-triacontene-1,30-diyl; and branched alkenylene groups such as 1-methylethylene-1,2-diyl, 2-methyl-1-propen-1,3-diyl, 2-methyl-2-propen-1,3-diyl, 2-methyl-1-butene-1,4-diyl, 3-methyl-2-butene-1,4-diyl, 2-methyl-3-butene-1,4-diyl, 2,3-dimethyl-1,3-butadiene-1,4-diyl, 3-ethyl-2-propen-1,5-diyl, 4-methyl-3-propen-1,5-diyl, 3-methyl-2,4-propadiene-1,5-diyl, 3,4-diethyl-2-hexene-1,6-diyl, 4-methyl-3-hexene-1,6-diyl, 2-methyl-4-hexene-1,6-diyl, 3,5-dimethyl-2,4-hexadiene-1,6-diyl, 5-ethyl-3-methyl-2-heptene-1,7-diyl, 5-methyl-3-heptene-1,7-diyl, 4-n-propyl-4-heptene-1,7-diyl, 3,6-dimethyl-5-heptene-1,7-diyl, 5-ethyl-2,4-heptadiene-1,7-diyl, 2,6-dimethyl-2,5-heptadiene-1,7-diyl, 4-ethyl-3,5-heptadiene-1,7-diyl, 4-ethyl-6,6-dimethyl-2-octene-1,8-diyl, 5-n-propyl-3-octene-1,8-diyl, 3-ethyl-4-octene-1,8-diyl, 4-ethyl-2-methyl-6-i-propyl-5-octene-1,8-diyl, 3,4,5-trimethyl-6-octene-1,8-diyl, 5-ethyl-7-methyl-2,4-octadiene-1,8-diyl, 3-methyl-2,5-octadiene-1,8-diyl, 5-n-propyl-2,6-octadiene-1,8-diyl, 4-methyl-2,4,6-octatriene-1,8-diyl, 5-ethyl-2-nonene-1,9-diyl, 3,5,6-trimethyl-3-nonene-1,9-diyl, 2,4,5,7-tetramethyl-4-nonene-1,9-diyl, 3,4-diethyl-5-nonene-1,9-diyl, 4-i-propyl-6-nonene-1,9-diyl, 3-ethyl-7-nonene-1,9-diyl, 5-n-butyl-2-decene-1,10-diyl, 6-i-propyl-3-decene-1,10-diyl, 5-ethyl-4-decene-1,10-diyl, 6,7-dimethyl-5-decene-1,10-diyl, 4-ethyl-6-decene-1,10-diyl, 5-methyl-7-decene-1,10-diyl, 6-ethyl-4-methyl-8-decene-1,10-diyl, 6-methyl-2-undecene-1,11-diyl, 4-ethyl-3-undecene-1,11-diyl, 5-methyl-4-undecene-1,11-diyl, 7-ethyl-5-undecene-1,11-diyl, 5-methyl-6-undecene-1,11-diyl, 9-ethyl-7-undecene-1,11-diyl, 3-methyl-8-undecene-1,11-diyl, 4-ethyl-9-undecene-1,11-diyl, 4-ethyl-2-dodecene-1,12-diyl, 5-methyl-3-dodecene-1,12-diyl, 6-ethyl-4-dodecene-1,12-diyl, 7-methyl-5-dodecene-1,12-diyl, 8-ethyl-6-dodecene-1,12-diyl, 9-methyl-7-dodecene-1,12-diyl, 10-ethyl-8-dodecene-1,12-diyl, 2-methyl-9-dodecene-1,12-diyl, 5-ethyl-10-dodecene-1,12-diyl, 4,7,9-trimethyl-2-tridecene-1,13-diyl, 10-methyl-3-tridecene-1,13-diyl, 8-ethyl-4-tridecene-1,13-diyl, 4-methyl-5-tridecene-1,13-diyl, 5-ethyl-6-tridecene-1,13-diyl, 3,6-diethyl-7-tridecene-1,13-diyl, 5-methyl-8-tridecene-1,13-diyl, 7-ethyl-9-tridecene-1,13-diyl, 4-methyl-10-tridecene-1,13-diyl, 6-ethyl-11-tridecene-1,13-diyl, 7-methyl-2-tetradecene-1,14-diyl, 8-ethyl-3-tetradecene-1,14-diyl, 6-n-propyl-4-tetradecene-1,14-diyl, 8-methyl-5-tetradecene-1,14-diyl, 3-ethyl-6-tetradecene-1,14-diyl, 10-methyl-7-tetradecene-1,14-diyl, 6-i-propyl-8-tetradecene-1,14-diyl, 5,7,11-trimethyl-9-tetradecene-1,14-diyl, 5-ethyl-10-tetradecene-1,14-diyl, 6-methyl-11-tetradecene-1,14-diyl, 4-n-butyl-12-tetradecene-1,14-diyl, 4-methyl-2-pentadecene-1,15-diyl, 6-ethyl-3-pentadecene-1,15-diyl, 8-methyl-4-pentadecene-1,15-diyl, 10-ethyl-5-pentadecene-1,15-diyl, 4,9-dimethyl-6-pentadecene-1,15-diyl, 10-ethyl-7-pentadecene-1,15-diyl, 6-methyl-8-pentadecene-1,15-diyl, 8-n-propyl-9-pentadecene-1,15-diyl, 5-methyl-10-pentadecene-1,15-diyl, 4,7-diethyl-11-pentadecene-1,15-diyl, 5-methyl-12-pentadecene-1,15-diyl, 8-ethyl-13-pentadecene-1,15-diyl, 8-i-propyl-2-hexadecene-1,16-diyl, 6-methyl-3-hexadecene-1,16-diyl, 8-ethyl-4-hexadecene-1,16-diyl, 9-methyl-5-hexadecene-1,16-diyl, 10-ethyl-6-hexadecene-1,16-diyl, 5-methyl-7-hexadecene-1,16-diyl, 5,10-dimethyl-8-hexadecene-1,16-diyl, 5-ethyl-9-hexadecene-1,16-diyl, 7,12-diethyl-10-hexadecene-1,16-diyl, 5-ethyl-7-methyl-11-hexadecene-1,16-diyl, 5-methyl-12-hexadecene-1,16-diyl, 8-s-butyl-13-hexadecene-1,16-diyl, 5-ethyl-14-hexadecene-1,16-diyl, 11-methyl-2-heptadecene-1,17-diyl, 9-ethyl-3-heptadecene-1,17-diyl, 6-i-propyl-4-heptadecene-1,17-diyl, 8-methyl-5-heptadecene-1,17-diyl, 4-ethyl-6-heptadecene-1,17-diyl, 10-methyl-7-heptadecene-1,17-diyl, 5,11-dimethyl-8-heptadecene-1,17-diyl, 5-ethyl-9-heptadecene-1,17-diyl, 8-ethyl-10-heptadecene-1,17-diyl, 7-methyl-11-heptadecene-1,17-diyl, 5-i-propyl-12-heptadecene-1,17-diyl, 9-ethyl-13-heptadecene-1,17-diyl, 8-methyl-14-heptadecene-1,17-diyl, 7-s-butyl-15-heptadecene-1,17-diyl, 10,15-dimethyl-2-octadecene-1,18-diyl, 6-ethyl-3-octadecene-1,18-diyl, 10-methyl-4-octadecene-1,18-diyl, 11-methyl-5-octadecene-1,18-diyl, 12-ethyl-6-octadecene-1,18-diyl, 10-methyl-7-octadecene-1,18-diyl, 5-methyl-8-octadecene-1,18-diyl, 8-ethyl-9-octadecene-1,18-diyl, 7-methyl-10-octadecene-1,18-diyl, 9-n-butyl-11-octadecene-1,18-diyl, 7-methyl-12-octadecene-1,18-diyl, 9-ethyl-13-octadecene-1,18-diyl, 10-i-propyl-14-octadecene-1,18-diyl, 7-methyl-15-octadecene-1,18-diyl, 10-ethyl-16-octadecene-1,18-diyl, 10-methyl-2-nonadecene-1,19-diyl, 10,12-diethyl-3-nonadecene-1,19-diyl, 6-methyl-4-nonadecene-1,19-diyl, 7-ethyl-5-nonadecene-1,19-diyl, 9-n-propyl-6-nonadecene-1,19-diyl, 10-methyl-7-nonadecene-1,19-diyl, 12-i-propyl-8-nonadecene-1,19-diyl, 5,15-dimethyl-9-nonadecene-1,19-diyl, 7-ethyl-13-methyl-10-nonadecene-1,19-diyl, 6-methyl-11-nonadecene-1,19-diyl, 6-ethyl-12-nonadecene-1,19-diyl, 7,15-diethyl-13-nonadecene-1,19-diyl, 9-s-butyl-14-nonadecene-1,19-diyl, 8-methyl-15-nonadecene-1,19-diyl, 10-ethyl-16-nonadecene-1,19-diyl, 10-i-propyl-17-nonadecene-1,19-diyl, 8-methyl-2-icosene-1,20-diyl, 6-ethyl-3-icosene-1,20-diyl, 10-i-propyl-4-icosene-1,20-diyl, 11-n-propyl-5-icosene-1,20-diyl, 12-methyl-6-icosene-1,20-diyl, 11-ethyl-7-icosene-1,20-diyl, 13-n-propyl-8-icosene-1,20-diyl, 8-i-propyl-9-icosene-1,20-diyl, 8-n-propyl-10-icosene-1,20-diyl, 7-methyl-11-icosene-1,20-diyl, 8-ethyl-12-icosene-1,20-diyl, 10-n-propyl-13-icosene-1,20-diyl, 9-i-propyl-14-icosene-1,20-diyl, 10-n-butyl-15-icosene-1,20-diyl, 8-s-butyl-16-icosene-1,20-diyl, 7-i-butyl-17-icosene-1,20-diyl, 9-methyl-18-icosene-1,20-diyl, 11-methyl-2-henicosene-1,21-diyl, 12-n-butyl-3-henicosene-1,21-diyl, 10-n-pentyl-4-henicosene-1,21-diyl, 8-ethyl-5-henicosene-1,21-diyl, 10-i-propyl-6-henicosene-1,21-diyl, 5-n-propyl-7-henicosene-1,21-diyl, 13-n-butyl-8-henicosene-1,21-diyl, 15-s-butyl-9-henicosene-1,21-diyl, 5-methyl-10-henicosene-1,21-diyl, 15-ethyl-6-methyl-11-henicosene-1,21-diyl, 8-ethyl-12-henicosene-1,21-diyl, 7-methyl-13-henicosene-1,21-diyl, 11-ethyl-14-henicosene-1,21-diyl, 6-ethyl-15-henicosene-1,21-diyl, 9-methyl-16-henicosene-1,21-diyl, 5-ethyl-9-methyl-17-henicosene-1,21-diyl, 10,10-dimethyl-18-henicosene-1,21-diyl, 9-ethyl-19-henicosene-1,21-diyl, 11-methyl-2-docosene-1,22-diyl, 12-ethyl-3-docosene-1,22-diyl, 13-i-propyl-4-docosene-1,22-diyl, 10-n-propyl-5-docosene-1,22-diyl, 10-n-butyl-6-docosene-1,22-diyl, 15-s-butyl-7-docosene-1,22-diyl, 11-i-butyl-8-docosene-1,22-diyl, 5,15-dimethyl-9-docosene-1,22-diyl, 8,14-diethyl-10-docosene-1,22-diyl, 5-methyl-11-docosene-1,22-diyl, 7-ethyl-12-docosene-1,22-diyl, 10-methyl-13-docosene-1,22-diyl, 10-ethyl-14-docosene-1,22-diyl, 9-ethyl-15-docosene-1,22-diyl, 8-methyl-16-docosene-1,22-diyl, 7-i-propyl-17-docosene-1,22-diyl, 10-i-butyl-18-docosene-1,22-diyl, 9,10-dimethyl-19-docosene-1,22-diyl, 13-ethyl-20-docosene-1,22-diyl, 19-methyl-2-tricosene-1,23-diyl, 10,15-dimethyl-3-tricosene-1,23-diyl, 3,11,16-trimethyl-4-tricosene-1,23-diyl, 12-ethyl-5-tricosene-1,23-diyl, 6,13-diethyl-6-tricosene-1,23-diyl, 4,12,18-triethyl-7-tricosene-1,23-diyl, 18-i-propyl-8-tricosene-1,23-diyl, 14-n-propyl-9-tricosene-1,23-diyl, 8-n-butyl-10-tricosene-1,23-diyl, 15-s-butyl-11-tricosene-1,23-diyl, 5-i-butyl-12-tricosene-1,23-diyl, 7-ethyl-9-methyl-13-tricosene-1,23-diyl, 9-methyl-14-tricosene-1,23-diyl, 4,18-dimethyl-15-tricosene-1,23-diyl, 3,4,11-trimethyl-16-tricosene-1,23-diyl, 9-ethyl-17-tricosene-1,23-diyl, 10,13-diethyl-18-tricosene-1,23-diyl, 5,8,21-triethyl-19-tricosene-1,23-diyl, 15-i-propyl-20-tricosene-1,23-diyl, 17-n-propyl-21-tricosene-1,23-diyl, 16-n-butyl-2-tetracosene-1,24-diyl, 11-s-butyl-3-tetracosene-1,24-diyl, 8-i-butyl-4-tetracosene-1,24-diyl, 18-ethyl-9-methyl-5-tetracosene-1,24-diyl, 13-methyl-6-tetracosene-1,24-diyl, 4,19-dimethyl-7-tetracosene-1,24-diyl, 5,10,17-triethyl-8-tetracosene-1,24-diyl, 6-ethyl-9-tetracosene-1,24-diyl, 7,16-diethyl-10-tetracosene-1,24-diyl, 5,9,18-triethyl-11-tetracosene-1,24-diyl, 10-n-propyl-12-tetracosene-1,24-diyl, 20-i-propyl-13-tetracosene-1,24-diyl, 9-n-butyl-14-tetracosene-1,24-diyl, 11-s-butyl-15-tetracosene-1,24-diyl, 13-i-butyl-16-tetracosene-1,24-diyl, 10-ethyl-13-methyl-17-tetracosene-1,24-diyl, 6-methyl-18-tetracosene-1,24-diyl, 5,7-dimethyl-19-tetracosene-1,24-diyl, 4,8,13-trimethyl-20-tetracosene-1,24-diyl, 18-ethyl-21-tetracosene-1,24-diyl, 6,10-diethyl-22-tetracosene-1,24-diyl, 9,13,16-trimethyl-2-pentacosene-1,25-diyl, 12-n-propyl-3-pentacosene-1,25-diyl, 11-i-propyl-4-pentacosene-1,25-diyl, 20-n-butyl-5-pentacosene-1,25-diyl, 17-i-butyl-6-pentacosene-1,25-diyl, 15-s-butyl-7-pentacosene-1,25-diyl, 15-ethyl-23-methyl-8-pentacosene-1,25-diyl, 11-methyl-8-pentacosene-1,25-diyl, 13,17-dimethyl-9-pentacosene-1,25-diyl, 5,8,21-trimethyl-10-pentacosene-1,25-diyl, 17-ethyl-11-pentacosene-1,25-diyl, 8,18-diethyl-12-pentacosene-1,25-diyl, 10,15,18-trimethyl-13-pentacosene-1,25-diyl, 4-n-propyl-14-pentacosene-1,25-diyl, 20-i-propyl-15-pentacosene-1,25-diyl, 8-n-butyl-16-pentacosene-1,25-diyl, 11-s-butyl-17-pentacosene-1,25-diyl, 5,22-dimethyl-18-pentacosene-1,25-diyl, 5-i-butyl-19-pentacosene-1,25-diyl, 9-methyl-13-ethyl-20-pentacosene-1,25-diyl, 15-methyl-21-pentacosene-1,25-diyl, 6,13-dimethyl-22-pentacosene-1,25-diyl, 4,8,12-trimethyl-23-pentacosene-1,25-diyl, 13-ethyl-2-hexacosene-1,26-diyl, 5,16-diethyl-3-hexacosene-1,26-diyl, 7,11,16-trimethyl-4-hexacosene-1,26-diyl, 12-n-propyl-5-hexacosene-1,26-diyl, 21-i-propyl-6-hexacosene-1,26-diyl, 6-n-butyl-7-hexacosene-1,26-diyl, 13-s-butyl-8-hexacosene-1,26-diyl, 19-i-butyl-9-hexacosene-1,26-diyl, 13-ethyl-18-methyl-10-hexacosene-1,26-diyl, 10-methyl-11-hexacosene-1,26-diyl, 10,20-dimethyl-12-hexacosene-1,26-diyl, 7,9,17-trimethyl-13-hexacosene-1,26-diyl, 8-ethyl-14-hexacosene-1,26-diyl, 5,22-diethyl-15-hexacosene-1,26-diyl, 7,10,21-trimethyl-16-hexacosene-1,26-diyl, 15-n-propyl-17-hexacosene-1,26-diyl, 13-i-propyl-18-hexacosene-1,26-diyl, 8-n-butyl-19-hexacosene-1,26-diyl, 11-s-butyl-20-hexacosene-1,26-diyl, 14-i-butyl-21-hexacosene-1,26-diyl, 5-ethyl-21-methyl-22-hexacosene-1,26-diyl, 7-methyl-23-hexacosene-1,26-diyl, 8,14-dimethyl-24-hexacosene-1,26-diyl, 7,16,24-trimethyl-2-heptacosene-1,27-diyl, 9-ethyl-3-heptacosene-1,27-diyl, 7,16-dimethyl-4-heptacosene-1,27-diyl, 9,13,21-trimethyl-5-heptacosene-1,27-diyl, 13-n-propyl-6-heptacosene-1,27-diyl, 10-i-propyl-7-heptacosene-1,27-diyl, 16-n-propyl-8-heptacosene-1,27-diyl, 18-methyl-9-heptacosene-1,27-diyl, 9-i-propyl-10-heptacosene-1,27-diyl, 15-ethyl-7-methyl-11-heptacosene-1,27-diyl, 25-methyl-12-heptacosene-1,27-diyl, 8,21-dimethyl-13-heptacosene-1,27-diyl, 5,11,23- trimethyl-14-heptacosene-1,27-diyl, 9-ethyl-15-heptacosene-1,27-diyl, 8,20-dimethyl-16-heptacosene-1,27-diyl, 4,8,19-trimethyl-17-heptacosene-1,27-diyl, 7-n-propyl-18-heptacosene-1,27-diyl, 21-i-propyl-19-heptacosene-1,27-diyl, 14-n-propyl-20-heptacosene-1,27-diyl, 8-ethyl-21-heptacosene-1,27-diyl, 11-i-propyl-22-heptacosene-1,27-diyl, 5-ethyl-13-methyl-23-heptacosene-1,27-diyl, 16-methyl-24-heptacosene-1,27-diyl, 7-ethyl-25-heptacosene-1,27-diyl, 14-ethyl-2-octacosene-1,28-diyl, 20-methyl-3-octacosene-1,28-diyl, 7,22-dimethyl-4-octacosene-1,28-diyl, 19-ethyl-5-octacosene-1,28-diyl, 11-methyl-6-octacosene-1,28-diyl, 13,16-dimethyl-7-octacosene-1,28-diyl, 13-ethyl-8-octacosene-1,28-diyl, 6-methyl-9-octacosene-1,28-diyl, 9,16-dimethyl-10-octacosene-1,28-diyl, 7-ethyl-11-octacosene-1,28-diyl, 16-methyl-12-octacosene-1,28-diyl, 6,15-dimethyl-13-octacosene-1,28-diyl, 22-ethyl-14-octacosene-1,28-diyl, 6-methyl-15-octacosene-1,28-diyl, 8,11-dimethyl-16-octacosene-1,28-diyl, 23-ethyl-17-octacosene-1,28-diyl, 4-methyl-18-octacosene-1,28-diyl, 7,14-dimethyl-19-octacosene-1,28-diyl, 13-ethyl-20-octacosene-1,28-diyl, 8-methyl-21-octacosene-1,28-diyl, 11,17-dimethyl-22-octacosene-1,28-diyl, 10-ethyl-23-octacosene-1,28-diyl, 9-methyl-24-octacosene-1,28-diyl, 7,19-dimethyl-25-octacosene-1,28-diyl, 12-ethyl-26-octacosene-1,28-diyl, 15-methyl-2-nonacosene-1,29-diyl, 14-methyl-3-nonacosene-1,29-diyl, 12-methyl-4-nonacosene-1,29-diyl, 13-methyl-5-nonacosene-1,29-diyl, 11-methyl-6-nonacosene-1,29-diyl, 10-methyl-7-nonacosene-1,29-diyl, 25-methyl-8-nonacosene-1,29-diyl, 24-methyl-9-nonacosene-1,29-diyl, 23-methyl-10-nonacosene-1,29-diyl, 22-methyl-11-nonacosene-1,29-diyl, 21-methyl-12-nonacosene-1,29-diyl, 20-methyl-13-nonacosene-1,29-diyl, 19-methyl-14-nonacosene-1,29-diyl, 18-methyl-15-nonacosene-1,29-diyl, 27-methyl-16-nonacosene-1,29-diyl, 26-methyl-17-nonacosene-1,29-diyl, 25-methyl-18-nonacosene-1,29-diyl, 24-methyl-19-nonacosene-1,29-diyl, 23-methyl-20-nonacosene-1,29-diyl, 20-methyl-21-nonacosene-1,29-diyl, 19-methyl-22-nonacosene-1,29-diyl, 18-methyl-23-nonacosene-1,29-diyl, 17-methyl-24-nonacosene-1,29-diyl, 16-methyl-25-nonacosene-1,29-diyl, 6-methyl-26-nonacosene-1,29-diyl and 5-methyl-27-nonacosene-1,29-diyl.

Examples of a linear or branched $C_2$–$C_{30}$ alkynylene group in the optionally substituted linear or branched $C_2$–$C_{30}$ alkynylene group as G include:

linear alkynylene groups such as acetylene-1,2-diyl, 1-propyne-1,3-diyl, 2-propyne-1,3-diyl, 1-butyne-1,4-diyl, 2-butyne-1,4-diyl, 3-butyne-1,4-diyl, 1,3-butadiyne-1,4-diyl, 2-pentyne-1,5-diyl, 3-pentyne-1,5-diyl, 2,4-pentadiyne-1,5-diyl, 2-hexyne-1,6-diyl, 3-hexyne-1,6-diyl, 4-hexyne-1,6-diyl, 2,4-hexadiyne-1,6-diyl, 2-heptyne-1,7-diyl, 3-heptyne-1,7-diyl, 4-heptyne-1,7-diyl, 5-heptyne-1,7-diyl, 2,4-heptadiyne-1,7-diyl, 2,5-heptadiyne-1,7-diyl, 3,5-heptadiyne-1,7-diyl, 2-octyne-1,8-diyl, 3-octyne-1,8-diyl, 4-octyne-1,8-diyl, 5-octyne-1,8-diyl, 6-octyne-1,8-diyl, 2,4-octadiyne-1,8-diyl, 2,5-octadiyne-1,8-diyl, 2,6-octadiyne-1,8-diyl, 2,4,6-octatriyne-1,8-diyl, 2-nonyne-1,9-diyl, 3-nonyne-1,9-diyl, 4-nonyne-1,9-diyl, 5-nonyne-1,9-diyl, 6-nonyne-1,9-diyl, 7-nonyne-1,9-diyl, 2-decyne-1,10-diyl, 3-decyne-1,10-diyl, 4-decyne-1,10-diyl, 5-decyne-1,10-diyl, 6-decyne-1,10-diyl, 7-decyne-1,10-diyl, 8-decyne-1,10-diyl, 2-undecyne-1,11-diyl, 3-undecyne-1,11-diyl, 4-undecyne-1,11-diyl, 5-undecyne-1,11-diyl, 6-undecyne-1,11-diyl, 7-undecyne-1,11-diyl, 8-undecyne-1,11-diyl, 9-undecyne-1,11-diyl, 2-dodecyne-1,12-diyl, 3-dodecyne-1,12-diyl, 4-dodecyne-1,12-diyl, 5-dodecyne-1,12-diyl, 6-dodecyne-1,12-diyl, 7-dodecyne-1,12-diyl, 8-dodecyne-1,12-diyl, 9-dodecyne-1,12-diyl, 10-dodecyne-1,12-diyl, 2-tridecyne-1,13-diyl, 3-tridecyne-1,13-diyl, 4-tridecyne-1,13-diyl, 5-tridecyne-1,13-diyl, 6-tridecyne-1,13-diyl, 7-tridecyne-1,13-diyl, 8-tridecyne-1,13-diyl, 9-tridecyne-1,13-diyl, 10-tridecyne-1,13-diyl, 11-tridecyne-1,13-diyl, 2-tetradecyne-1,14-diyl, 3-tetradecyne-1,14-diyl, 4-tetradecyne-1,14-diyl, 5-tetradecyne-1,14-diyl, 6-tetradecyne-1,14-diyl, 7-tetradecyne-1,14-diyl, 8-tetradecyne-1,14-diyl, 9-tetradecyne-1,14-diyl, 10-tetradecyne-1,14-diyl, 11-tetradecyne-1,14-diyl, 12-tetradecyne-1,14-diyl, 2-pentadecyne-1,15-diyl, 3-pentadecyne-1,15-diyl, 4-pentadecyne-1,15-diyl, 5-pentadecyne-1,15-diyl, 6-pentadecyne-1,15-diyl, 7-pentadecyne-1,15-diyl, 8-pentadecyne-1,15-diyl, 9-pentadecyne-1,15-diyl, 10-pentadecyne-1,15-diyl, 11-pentadecyne-1,15-diyl, 12-pentadecyne-1,15-diyl, 13-pentadecyne-1,15-diyl, 2-hexadecyne-1,16-diyl, 3-hexadecyne-1,16-diyl, 4-hexadecyne-1,16-diyl, 5-hexadecyne-1,16-diyl, 6-hexadecyne-1,16-diyl, 7-hexadecyne-1,16-diyl, 8-hexadecyne-1,16-diyl, 9-hexadecyne-1,16-diyl, 10-hexadecyne-1,16-diyl, 11-hexadecyne-1,16-diyl, 12-hexadecyne-1,16-diyl, 13-hexadecyne-1,16-diyl, 14-hexadecyne-1,16-diyl, 2-heptadecyne-1,17-diyl, 3-heptadecyne-1,17-diyl, 4-heptadecyne-1,17-diyl, 5-heptadecyne-1,17-diyl, 6-heptadecyne-1,17-diyl, 7-heptadecyne-1,17-diyl, 8-heptadecyne-1,17-diyl, 9-heptadecyne-1,17-diyl, 10-heptadecyne-1,17-diyl, 11-heptadecyne-1,17-diyl, 12-heptadecyne-1,17-diyl, 13-heptadecyne-1,17-diyl, 14-heptadecyne-1,17-diyl, 15-heptadecyne-1,17-diyl, 2-octadecyne-1,18-diyl, 3-octadecyne-1,18-diyl, 4-octadecyne-1,18-diyl, 5-octadecyne-1,18-diyl, 6-octadecyne-1,18-diyl, 7-octadecyne-1,18-diyl, 8-octadecyne-1,18-diyl, 9-octadecyne-1,18-diyl, 10-octadecyne-1,18-diyl, 11-octadecyne-1,18-diyl, 12-octadecyne-1,18-diyl, 13-octadecyne-1,18-diyl, 14-octadecyne-1,18-diyl, 15-octadecyne-1,18-diyl, 16-octadecyne-1,18-diyl, 2-nonadecyne-1,19-diyl, 3-nonadecyne-1,19-diyl, 4-nonadecyne-1,19-diyl, 5-nonadecyne-1,19-diyl, 6-nonadecyne-1,19-diyl, 7-nonadecyne-1,19-diyl, 8-nonadecyne-1,19-diyl, 9-nonadecyne-1,19-diyl, 10-nonadecyne-1,19-diyl, 11-nonadecyne-1,19-diyl, 12-nonadecyne-1,19-diyl, 13-nonadecyne-1,19-diyl, 14-nonadecyne-1,19-diyl, 15-nonadecyne-1,19-diyl, 16-nonadecyne-1,19-diyl, 17-nonadecyne-1,19-diyl, 2-icosyne-1,20-diyl, 3-icosyne-1,20-diyl, 4-icosyne-1,20-diyl, 5-icosyne-1,20-diyl, 6-icosyne-1,20-diyl, 7-icosyne-1,20-diyl, 8-icosyne-1,20-diyl, 9-icosyne-1,20-diyl, 10-icosyne-1,20-diyl, 11-icosyne-1,20-diyl, 12-icosyne-1,20-diyl, 13-icosyne-1,20-diyl, 14-icosyne-1,20-diyl, 15-icosyne-1,20-diyl, 16-icosyne-1,20-diyl, 17-icosyne-1,20-diyl, 18-icosyne-1,20-diyl, 2-henicosyne-1,21-diyl, 3-henicosyne-1,21-diyl, 4-henicosyne-1,21-diyl, 5-henicosyne-1,21-diyl, 6-henicosyne-1,21-diyl, 7-henicosyne-1,21-diyl, 8-henicosyne-1,21-diyl, 9-henicosyne-1,21-diyl, 10-henicosyne-1,21-diyl, 11-henicosyne-1,21-diyl, 12-henicosyne-1,21-diyl, 13-henicosyne-1,21-diyl, 14-henicosyne-1,21-diyl, 15-henicosyne-1,21-diyl, 16-henicosyne-1,21-diyl, 17-henicosyne-1,21-diyl, 18-henicosyne-1,21-diyl, 19-henicosyne-1,21-diyl, 2-docosyne-1,22-diyl, 3-docosyne-1,22-diyl, 4-docosyne-1,22-diyl, 5-docosyne-1,22-diyl, 6-docosyne-1,22-diyl, 7-docosyne-1,22-diyl, 8-docosyne-1,22-diyl, 9-docosyne-1,22-diyl, 10-docosyne-1,22-diyl, 11-docosyne-1,22-diyl, 12-docosyne-1,22-diyl, 13-docosyne-1,22-diyl, 14-docosyne-1,22-diyl, 15-docosyne-1,22-diyl, 16-docosyne-1,22-diyl, 17-docosyne-1,22-diyl, 18-docosyne-1,22-diyl, 19-docosyne-1,22-diyl, 20-docosyne-1,22-diyl, 2-tricosyne-1,23-diyl, 3-tricosyne-1,23-diyl, 4-tricosyne-1,23-diyl, 5-tricosyne-1,23-diyl, 6-tricosyne-1,23-diyl, 7-tricosyne-1,23-diyl, 8-tricosyne-1,23-diyl, 9-tricosyne-1,23-diyl, 10-tricosyne-1,23-diyl, 11-tricosyne-1,23-diyl, 12-tricosyne-1,23-diyl, 13-tricosyne-1,23-diyl, 14-tricosyne-1,23-diyl, 15-tricosyne-1,23-diyl, 16-tricosyne-1,23-diyl, 17-tricosyne-1,23-diyl, 18-tricosyne-1,23-diyl, 19-tricosyne-1,23-diyl, 20-tricosyne-1,23-diyl, 21-tricosyne-1,23-diyl, 2-tetracosyne-1,24-diyl, 3-tetracosyne-1,24-diyl, 4-tetracosyne-1,24-diyl, 5-tetracosyne-1,24-diyl, 6-tetracosyne-1,24-diyl, 7-tetracosyne-1,24-diyl, 8-tetracosyne-1,24-diyl, 9-tetracosyne-1,24-diyl, 10-tetracosyne-1,24-diyl, 11-tetracosyne-1,24-diyl, 12-tetracosyne-1,24-diyl, 13-tetracosyne-1,24-diyl, 14-tetracosyne-1,24-diyl, 15-tetracosyne-1,24-diyl, 16-tetracosyne-1,24-diyl, 17-tetracosyne-1,24-diyl, 18-tetracosyne-1,24-diyl, 19-tetracosyne-1,24-diyl, 20-tetracosyne-1,24-diyl, 21-tetracosyne-1,24-diyl, 22-tetracosyne-1,24-diyl, 2-pentacosyne-1,25-diyl, 3-pentacosyne-1,25-diyl, 4-pentacosyne-1,25-diyl, 5-pentacosyne-1,25-diyl, 6-pentacosyne-1,25-diyl, 7-pentacosyne-1,25-diyl, 8-pentacosyne-1,25-diyl, 8-pentacosyne-1,25-diyl, 9-pentacosyne-1,25-diyl, 10-pentacosyne-1,25-diyl, 11-pentacosyne-1,25-diyl, 12-pentacosyne-1,25-diyl, 13-pentacosyne-1,25-diyl, 14-pentacosyne-1,25-diyl, 15-pentacosyne-1,25-diyl, 16-pentacosyne-1,25-diyl, 17-pentacosyne-1,25-diyl, 18-pentacosyne-1,25-diyl, 19-pentacosyne-1,25-diyl, 20-pentacosyne-1,25-diyl, 21-pentacosyne-1,25-diyl, 22-pentacosyne-1,25-diyl, 23-pentacosyne-1,25-diyl, 2-hexacosyne-1,26-diyl, 3-hexacosyne-1,26-diyl, 4-hexacosyne-1,26-diyl, 5-hexacosyne-1,26-diyl, 6-hexacosyne-1,26-diyl, 7-hexacosyne-1,26-diyl, 8-hexacosyne-1,26-diyl, 9-hexacosyne-1,26-diyl, 10-hexacosyne-1,26-diyl, 11-hexacosyne-1,26-diyl, 12-hexacosyne-1,26-diyl, 13-hexacosyne-1,26-diyl, 14-hexacosyne-1,26-diyl, 15-hexacosyne-1,26-diyl, 16-hexacosyne-1,26-diyl, 17-hexacosyne-1,26-diyl, 18-hexacosyne-1,26-diyl, 19-hexacosyne-1,26-diyl, 20-hexacosyne-1,26-diyl, 21-hexacosyne-1,26-diyl, 22-hexacosyne-1,26-diyl, 23-hexacosyne-1,26-diyl, 24-hexacosyne-1,26-diyl, 2-heptacosyne-1,27-diyl, 3-heptacosyne-1,27-diyl, 4-heptacosyne-1,27-diyl, 5-heptacosyne-1,27-diyl, 6-heptacosyne-1,27-diyl, 7-heptacosyne-1,27-diyl, 8-heptacosyne-1,27-diyl, 9-heptacosyne-1,27-diyl, 10-heptacosyne-1,27-diyl, 11-heptacosyne-1,27-diyl, 12-heptacosyne-1,27-diyl, 13-heptacosyne-1,27-diyl, 14-heptacosyne-1,27-diyl, 15-heptacosyne-1,27-diyl, 16-heptacosyne-1,27-diyl, 17-heptacosyne-1,27-diyl, 18-heptacosyne-1,27-diyl, 19-heptacosyne-1,27-diyl, 20-heptacosyne-1,27-diyl, 21-heptacosyne-1,27-diyl, 22-heptacosyne-1,27-diyl, 23-heptacosyne-1,27-diyl, 24-heptacosyne-1,27-diyl, 25-heptacosyne-1,27-diyl, 2-octacosyne-1,28-diyl, 3-octacosyne-1,28-diyl, 4-octacosyne-1,28-diyl, 5-octacosyne-1,28-diyl, 6-octacosyne-1,28-diyl, 7-octacosyne-1,28-diyl, 8-octacosyne-1,28-diyl, 9-octacosyne-1,28-diyl, 10-octacosyne-1,28-diyl, 11-octacosyne-1,28-diyl, 12-octacosyne-1,28-diyl, 13-octacosyne-1,28-diyl, 14-octacosyne-1,28-diyl, 15-octacosyne-1,28-diyl, 16-octacosyne-1,28-diyl, 17-octacosyne-1,28-diyl, 18-octacosyne-1,28-diyl, 19-octacosyne-1,28-diyl, 20-octacosyne-1,28-diyl, 21-octacosyne-1,28-diyl, 22-octacosyne-1,28-diyl, 23-octacosyne-1,28-diyl, 24-octacosyne-1,28-diyl, 25-octacosyne-1,28-diyl, 26-octacosyne-1,28-diyl, 2-nonacosyne-1,29-diyl, 3-nonacosyne-1,29-diyl, 4-nonacosyne-1,29-diyl, 5-nonacosyne-1,29-diyl, 6-nonacosyne-1,29-diyl, 7-nonacosyne-1,29-diyl, 8-nonacosyne-1,29-diyl, 9-nonacosyne-1,29-diyl, 10-nonacosyne-1,29-diyl, 11-nonacosyne-1,29-diyl, 12-nonacosyne-1,29-diyl, 13-nonacosyne-1,29-diyl, 14-nonacosyne-1,29-diyl, 15-nonacosyne-1,29-diyl, 16-nonacosyne-1,29-diyl, 17-nonacosyne-1,29-diyl, 18-nonacosyne-1,29-diyl, 19-nonacosyne-1,29-diyl, 20-nonacosyne-1,29-diyl, 21-nonacosyne-1,29-diyl, 22-nonacosyne-1,29-diyl, 23-nonacosyne-1,29-diyl, 24-nonacosyne-1,29-diyl, 25-nonacosyne-1,29-diyl, 26-nonacosyne-1,29-diyl, 27-nonacosyne-1,29-diyl, 2-triacontyne-1,30-diyl, 3-triacontyne-1,30-diyl, 4-triacontyne-1,30-diyl, 5-triacontyne-1,30-diyl, 6-triacontyne-1,30-diyl, 7-triacontyne-1,30-diyl, 8-triacontyne-1,30-diyl, 9-triacontyne-1,30-diyl, 10-triacontyne-1,30-diyl, 11-triacontyne-1,30-diyl, 12-triacontyne-1,30-diyl, 13-triacontyne-1,30-diyl, 14-triacontyne-1,30-diyl, 15-triacontyne-1,30-diyl, 16-triacontyne-1,30-diyl, 17-triacontyne-1,30-diyl, 18-triacontyne-1,30-diyl, 19-triacontyne-1,30-diyl, 20-triacontyne-1,30-diyl, 21-triacontyne-1,30-diyl, 22-triacontyne-1,30-diyl, 23-triacontyne-1,30-diyl, 24-triacontyne-1,30-diyl, 25-triacontyne-1,30-diyl, 26-triacontyne-1,30-diyl, 27-triacontyne-1,30-diyl and 28-triacontyne-1,30-diyl; and branched alkynylene groups such as 3-methyl-1-butyne-1,4-diyl, 2-methyl-3-butyne-1,4-diyl, 4-methyl-2-pentyne-1,5-diyl, 2-methyl-3-pentyne-1,5-diyl, 4-ethyl-2-hexyne-1,6-diyl, 5-methyl-3-hexyne-1,6-diyl, 2-methyl-4-hexyne-1,6-diyl, 5-ethyl-6-methyl-2-heptyne-1,7-diyl, 5-methyl-3-heptyne-1,7-diyl, 3-n-propyl-4-heptyne-1,7-diyl, 4,4-dimethyl-5-heptyne-1,7-diyl, 6-methyl-2,4-heptadiyne-1,7-diyl, 4-methyl-2,5-heptadiyne-1,7-diyl, 2-methyl-3,5-heptadiyne-1,7-diyl, 4-ethyl-6,6-dimethyl-2-octyne-1,8-diyl, 5-n-propyl-3-octyne-1,8-diyl, 3-ethyl-4-octyne-1,8-diyl, 4-ethyl-2-methyl-5-octyne-1,8-diyl, 3,4,5-trimethyl-6-octyne-1,8-diyl, 7-methyl-2,4-octadiyne-1,8-diyl, 4-methyl-2,5-octadiyne-1,8-diyl, 5-n-propyl-2,6-octadiyne-1,8-diyl, 5-ethyl-2-nonyne-1,9-diyl, 5,6,7-trimethyl-3-nonyne-1,9-diyl, 2,3,6,7-tetramethyl-4-nonyne-1,9-diyl, 3,4-diethyl-5-nonyne-1,9-diyl, 4-i-propyl-6-nonyne-1,9-diyl, 3-ethyl-7-nonyne-1,9-diyl, 5-n-butyl-2-decyne-1,10-diyl, 6-i-propyl-3-decyne-1,10-diyl, 7-ethyl-4-decyne-1,10-diyl, 3,7-dimethyl-5-decyne-1,10-diyl, 4-ethyl-6-decyne-1,10-diyl, 5-methyl-7-decyne-1,10-diyl, 6-ethyl-4-methyl-8-decyne-1,10-diyl, 6-methyl-2-undecyne-1,11-diyl, 6-ethyl-3-undecyne-1,11-diyl, 7-methyl-4-undecyne-1,11-diyl, 7-ethyl-5-undecyne-1,11-diyl, 5-methyl-6-undecyne-1,11-diyl, 9-ethyl-7-undecyne-1,11-diyl, 3-methyl-8-undecyne-1,11-diyl, 4ethyl-9-undecyne-1,11-diyl, 5-ethyl-2-dodecyne-1,12-diyl, 6-methyl-3-dodecyne-1,12-diyl, 8-ethyl-4-dodecyne-1,12-diyl, 8-methyl-5-dodecyne-1,12-diyl, 9-ethyl-6-dodecyne-1,12-diyl, 6-methyl-7-dodecyne-1,12-diyl, 10-ethyl-8-dodecyne-1,12-diyl, 2-methyl-9-dodecyne-1,12-diyl, 5-ethyl-10-dodecyne-1,12-diyl, 4,7,9-trimethyl-2-tridecyne-1,13-diyl, 10-methyl-3-tridecyne-1,13-diyl, 8-ethyl-4-tridecyne-1,13-diyl, 4-methyl-5-tridecyne-1,13-diyl, 5-ethyl-6-tridecyne-1,13-diyl, 3,6-diethyl-7-tridecyne-1,13-diyl, 5-methyl-8- tridecyne-1,13-diyl, 7-ethyl-9-tridecyne-1,13-diyl, 4-methyl-10-tridecyne-1,13-diyl, 6-ethyl-11-tridecyne-1,13-diyl, 7-methyl-2-tetradecyne-1,14-diyl, 8-ethyl-3-tetradecyne-1,14-diyl, 6-n-propyl-4-tetradecyne-1,14-diyl, 8-methyl-5-tetradecyne-1,14-diyl, 3-ethyl-6-tetradecyne-1,14-diyl, 10-methyl-7-tetradecyne-1,14-diyl, 6-i-propyl-8-tetradecyne-1,14-diyl, 5,7,11-trimethyl-9-tetradecyne-1,14-diyl, 5-ethyl-10-tetradecyne-1,14-diyl, 6-methyl-11-tetradecyne-1,14-diyl, 4-n-butyl-12-tetradecyne-1,14-diyl, 4-methyl-2-pentadecyne-1,15-diyl, 6-ethyl-3-pentadecyne-1,15-diyl, 8-methyl-4-pentadecyne-1,15-diyl, 10-ethyl-5-pentadecyne-1,15-diyl, 4,9-dimethyl-6-pentadecyne-1,15-diyl, 10-ethyl-7-pentadecyne-1,15-diyl, 6-methyl-8-pentadecyne-1,15-diyl, 8-n-propyl-9-pentadecyne-1,15-diyl, 5-methyl-10-pentadecyne-1,15-diyl, 4,7-diethyl-11-pentadecyne-1,15-diyl, 5-methyl-12-pentadecyne-1,15-diyl, 8-ethyl-13-pentadecyne-1,15-diyl, 8-i-propyl-2-hexadecyne-1,16-diyl, 6-methyl-3-hexadecyne-1,16-diyl, 8-ethyl-4-hexadecyne-1,16-diyl, 9-methyl-5-hexadecyne-1,16-diyl, 10-ethyl-6-hexadecyne-1,16-diyl, 5-methyl-7-hexadecyne-1,16-diyl, 5,11-dimethyl-8-hexadecyne-1,16-diyl, 5-ethyl-9-hexadecyne-1,16-diyl, 7,13-diethyl-10-hexadecyne-1,16-diyl, 5-ethyl-7-methyl-11-hexadecyne-1,16-diyl, 5-methyl-12-hexadecyne-1,16-diyl, 8-s-butyl-13-hexadecyne-1,16-diyl, 5-ethyl-14-hexadecyne-1,16-diyl, 11-methyl-2-heptadecyne-1,17-diyl, 9-ethyl-3-heptadecyne-1,17-diyl, 7-i-propyl-4-heptadecyne-1,17-diyl, 8-methyl-5-heptadecyne-1,17-diyl, 4-ethyl-6-heptadecyne-1,17-diyl, 10-methyl-7-heptadecyne-1,17-diyl, 5,11-dimethyl-8-heptadecyne-1,17-diyl, 5-ethyl-9-heptadecyne-1,17-diyl, 8-ethyl-10-heptadecyne-1,17-diyl, 7-methyl-11-heptadecyne-1,17-diyl, 5-i-propyl-12-heptadecyne-1,17-diyl, 9-ethyl-13-heptadecyne-1,17-diyl, 8-methyl-14-heptadecyne-1,17-diyl, 7-s-butyl-15-heptadecyne-1,17-diyl, 10,15-dimethyl-2-octadecyne-1,18-diyl, 6-ethyl-3-octadecyne-1,18-diyl, 10-methyl-4-octadecyne-1,18-diyl, 11-methyl-5-octadecyne-1,18-diyl, 12-ethyl-6-octadecyne-1,18-diyl, 10-methyl-7-octadecyne-1,18-diyl, 5-methyl-8-octadecyne-1,18-diyl, 7-ethyl-9-octadecyne-1,18-diyl, 7-methyl-10-octadecyne-1,18-diyl, 8-n-butyl-11-octadecyne-1,18-diyl, 7-methyl-12-octadecyne-1,18-diyl, 9-ethyl-13-octadecyne-1,18-diyl, 10-i-propyl-14-octadecyne-1,18-diyl, 7-methyl-15-octadecyne-1,18-diyl, 10-ethyl-16-octadecyne-1,18-diyl, 10-methyl-2-nonadecyne-1,19-diyl, 10,12-diethyl-3-nonadecyne-1,19-diyl, 7-methyl-4-nonadecyne-1,19-diyl, 9-ethyl-5-nonadecyne-1,19-diyl, 9-n-propyl-6-nonadecyne-1,19-diyl, 10-methyl-7-nonadecyne-1,19-diyl, 12-i-propyl-8-nonadecyne-1,19-diyl, 5,15-dimethyl-9-nonadecyne-1,19-diyl, 7-ethyl-13-methyl-10-nonadecyne-1,19-diyl, 6-methyl-11-nonadecyne-1,19-diyl, 6-ethyl-12-nonadecyne-1,19-diyl, 7,16-diethyl-13-nonadecyne-1,19-diyl, 9-s-butyl-14-nonadecyne-1,19-diyl, 8-methyl-15-nonadecyne-1,19-diyl, 10-ethyl-16-nonadecyne-1,19-diyl, 10-i-propyl-17-nonadecyne-1,19-diyl, 8-methyl-2-icosyne-1,20-diyl, 6-ethyl-3-icosyne-1,20-diyl, 10-i-propyl-4-icosyne-1,20-diyl, 11-n-propyl-5-icosyne-1,20-diyl, 12-methyl-6-icosyne-1,20-diyl, 11-ethyl-7-icosyne-1,20-diyl, 13-n-propyl-8-icosyne-1,20-diyl, 6-i-propyl-9-icosyne-1,20-diyl, 5-n-propyl-10-icosyne-1,20-diyl, 7-methyl-11-icosyne-1,20-diyl, 8-ethyl-12-icosyne-1,20-diyl, 10-n-propyl-13-icosyne-1,20-diyl, 9-i-propyl-14-icosyne-1,20-diyl, 10-n-butyl-15-icosyne-1,20-diyl, 8-s-butyl-16-icosyne-1,20-diyl, 7-i-butyl-17-icosyne-1,20-diyl, 9-methyl-18-icosyne-1,20-diyl, 11-methyl-2-henicosyne-1,21-diyl, 12-n-butyl-3-henicosyne-1,21-diyl, 10-n-pentyl-4-henicosyne-1,21-diyl, 8-ethyl-5-henicosyne-1,21-diyl, 10-i-propyl-6-henicosyne-1,21-diyl, 5-n-propyl-7-henicosyne-1,21-diyl, 13-n-butyl-8-henicosyne-1,21-diyl, 15-s-butyl-9-henicosyne-1,21-diyl, 5-methyl-10-henicosyne-1,21-diyl, 15-ethyl-6-methyl-11-henicosyne-1,21-diyl, 8-ethyl-12-henicosyne-1,21-diyl, 7-methyl-13-henicosyne-1,21-diyl, 11-ethyl-14-henicosyne-1,21-diyl, 6-ethyl-15-henicosyne-1,21-diyl, 9-methyl-16-henicosyne-1,21-diyl, 5-ethyl-9-methyl-17-henicosyne-1,21-diyl, 10,10-dimethyl-18-henicosyne-1,21-diyl, 9-ethyl-19-henicosyne-1,21-diyl, 11-methyl-2-docosyne-1,22-diyl, 12-ethyl-3-docosyne-1,22-diyl, 13-i-propyl-4-docosyne-1,22-diyl, 10-n-propyl-5-docosyne-1,22-diyl, 10-n-butyl-6-docosyne-1,22-diyl, 15-s-butyl-7-docosyne-1,22-diyl, 11-i-butyl-8-docosyne-1,22-diyl, 5,15-dimethyl-9-docosyne-1,22-diyl, 8,14-diethyl-10-docosyne-1,22-diyl, 5-methyl-11-docosyne-1,22-diyl, 7-ethyl-12-docosyne-1,22-diyl, 10-methyl-13-docosyne-1,22-diyl, 10-ethyl-14-docosyne-1,22-diyl, 9-ethyl-15-docosyne-1,22-diyl, 8-methyl-16-docosyne-1,22-diyl, 7-i-propyl-17-docosyne-1,22-diyl, 10-i-butyl-18-docosyne-1,22-diyl, 9,10-dimethyl-19-docosyne-1,22-diyl, 13-ethyl-20-docosyne-1,22-diyl, 19-methyl-2-tricosyne-1,23-diyl, 10,15-dimethyl-3-tricosyne-1,23-diyl, 3,11,16-trimethyl-4-tricosyne-1,23-diyl, 12-ethyl-5-tricosyne-1,23-diyl, 6,13-diethyl-6-tricosyne-1,23-diyl, 4,12,18-triethyl-7-tricosyne-1,23-diyl, 18-i-propyl-8-tricosyne-1,23-diyl, 14-n-propyl-9-tricosyne-1,23-diyl, 8-n-butyl-10-tricosyne-1,23-diyl, 15-s-butyl-11-tricosyne-1,23-diyl, 5-i-butyl-12-tricosyne-1,23-diyl, 7-ethyl-9-methyl-13-tricosyne-1,23-diyl, 9-methyl-14-tricosyne-1,23-diyl, 4,18-dimethyl-15-tricosyne-1,23-diyl, 3,4,11-trimethyl-16-tricosyne-1,23-diyl, 9-ethyl-17-tricosyne-1,23-diyl, 10,13-diethyl-18-tricosyne-1,23-diyl, 5,8,15-triethyl-19-tricosyne-1,23-diyl, 15-i-propyl-20-tricosyne-1,23-diyl, 17-n-propyl-21-tricosyne-1,23-diyl, 16-n-butyl-2-tetracosyne-1,24-diyl, 11-s-butyl-3-tetracosyne-1,24-diyl, 8-i-butyl-4-tetracosyne-1,24-diyl, 18-ethyl-9-methyl-5-tetracosyne-1,24-diyl, 13-methyl-6-tetracosyne-1,24-diyl, 4,19-dimethyl-7-tetracosyne-1,24-diyl, 5,11,17-triethyl-8-tetracosyne-1,24-diyl, 6-ethyl-9-tetracosyne-1,24-diyl, 7,16-diethyl-10-tetracosyne-1,24-diyl, 5,9,18-triethyl-11-tetracosyne-1,24-diyl, 10-n-propyl-12-tetracosyne-1,24-diyl, 20-i-propyl-13-tetracosyne-1,24-diyl, 9-n-butyl-14-tetracosyne-1,24-diyl, 11-s-butyl-15-tetracosyne-1,24-diyl, 13-i-butyl-16-tetracosyne-1,24-diyl, 10-ethyl-13-methyl-17-tetracosyne-1,24-diyl, 6-methyl-18-tetracosyne-1,24-diyl, 5,7-dimethyl-19-tetracosyne-1,24-diyl, 4,8,13-trimethyl-20-tetracosyne-1,24-diyl, 18-ethyl-21-tetracosyne-1,24-diyl, 6,10-diethyl-22-tetracosyne-1,24-diyl, 9,13,16-trimethyl-2-pentacosyne-1,25-diyl, 12-n-propyl-3-pentacosyne-1,25-diyl, 11-i-propyl-4-pentacosyne-1,25-diyl, 20-n-butyl-5-pentacosyne-1,25-diyl, 17-i-butyl-6-pentacosyne-1,25-diyl, 15-s-butyl-7-pentacosyne-1,25-diyl, 15-ethyl-23-methyl-8-pentacosyne-1,25-diyl, 11-methyl-8-pentacosyne-1,25-diyl, 13,17-dimethyl-9-pentacosyne-1,25-diyl, 5,8,21-trimethyl-10-pentacosyne-1,25-diyl, 17-ethyl-11-pentacosyne-1,25-diyl, 8,18-diethyl-12-pentacosyne-1,25-diyl, 10,15,18-trimethyl-13-pentacosyne-1,25-diyl, 4-n-propyl-14-pentacosyne-1,25-diyl, 20-i-propyl-15-pentacosyne-1,25-diyl, 8-n-butyl-16-pentacosyne-1,25-diyl, 11-s-butyl-17-pentacosyne-1,25- diyl, 5,22-dimethyl-18-pentacosyne-1,25-diyl, 5-i-butyl-19-pentacosyne-1,25-diyl, 9-methyl-13-ethyl-20-pentacosyne-1,25-diyl, 15-methyl-21-pentacosyne-1,25-diyl, 6,13-dimethyl-22-pentacosyne-1,25-diyl, 4,8,12-trimethyl-23-pentacosyne-1,25-diyl, 13-ethyl-2-hexacosyne-1,26-diyl, 5,16-diethyl-3-hexacosyne-1,26-diyl, 7,11,16-trimethyl-4-hexacosyne-1,26-diyl, 12-n-propyl-5-hexacosyne-1,26-diyl, 21-i-propyl-6-hexacosyne-1,26-diyl, 6-n-butyl-7-hexacosyne-1,26-diyl, 13-s-butyl-8-hexacosyne-1,26-diyl, 19-i-butyl-9-hexacosyne-1,26-diyl, 13-ethyl-18-methyl-10-hexacosyne-1,26-diyl, 10-methyl-11-hexacosyne-1,26-diyl, 10,20-dimethyl-12-hexacosyne-1,26-diyl, 7,9,17-trimethyl-13-hexacosyne-1,26-diyl, 8-ethyl-14-hexacosyne-1,26-diyl, 5,22-diethyl-15-hexacosyne-1,26-diyl, 7,10,21-trimethyl-16-hexacosyne-1,26-diyl, 15-n-propyl-17-hexacosyne-1,26-diyl, 13-i-propyl-18-hexacosyne-1,26-diyl, 8-n-butyl-19-hexacosyne-1,26-diyl, 11-s-butyl-20-hexacosyne-1,26-diyl, 14-i-butyl-21-hexacosyne-1,26-diyl, 5-ethyl-21-methyl-22-hexacosyne-1,26-diyl, 7-methyl-23-hexacosyne-1,26-diyl, 8,14-dimethyl-24-hexacosyne-1,26-diyl, 7,16,24-trimethyl-2-heptacosyne-1,27-diyl, 9-ethyl-3-heptacosyne-1,27-diyl, 7,16-dimethyl-4-heptacosyne-1,27-diyl, 9,13,21-trimethyl-5-heptacosyne-1,27-diyl, 13-n-propyl-6-heptacosyne-1,27-diyl, 10-i-propyl-7-heptacosyne-1,27-diyl, 16-n-propyl-8-heptacosyne-1,27-diyl, 18-methyl-9-heptacosyne-1,27-diyl, 9-i-propyl-10-heptacosyne-1,27-diyl, 15-ethyl-7-methyl-11-heptacosyne-1,27-diyl, 25-methyl-12-heptacosyne-1,27-diyl, 8,21-dimethyl-13-heptacosyne-1,27-diyl, 5,11,23-trimethyl-14-heptacosyne-1,27-diyl, 9-ethyl-15-heptacosyne-1,27-diyl, 8,20-dimethyl-16-heptacosyne-1,27-diyl, 4,8,19-trimethyl-17-heptacosyne-1,27-diyl, 7-n-propyl-18-heptacosyne-1,27-diyl, 21-i-propyl-19-heptacosyne-1,27-diyl, 14-n-propyl-20-heptacosyne-1,27-diyl, 8-ethyl-21-heptacosyne-1,27-diyl, 11-i-propyl-22-heptacosyne-1,27-diyl, 5-ethyl-13-methyl-23-heptacosyne-1,27-diyl, 16-methyl-24-heptacosyne-1,27-diyl, 7-ethyl-25-heptacosyne-1,27-diyl, 14-ethyl-2-octacosyne-1,28-diyl, 20-methyl-3-octacosyne-1,28-diyl, 7,22-dimethyl-4-octacosyne-1,28-diyl, 19-ethyl-5-octacosyne-1,28-diyl, 11-methyl-6-octacosyne-1,28-diyl, 13,16-dimethyl-7-octacosyne-1,28-diyl, 13-ethyl-8-octacosyne-1,28-diyl, 6-methyl-9-octacosyne-1,28-diyl, 9,16-dimethyl-10-octacosyne-1,28-diyl, 7-ethyl-11-octacosyne-1,28-diyl, 16-methyl-12-octacosyne-1,28-diyl, 6,15-dimethyl-13-octacosyne-1,28-diyl, 22-ethyl-14-octacosyne-1,28-diyl, 6-methyl-15-octacosyne-1,28-diyl, 8,11-dimethyl-16-octacosyne-1,28-diyl, 23-ethyl-17-octacosyne-1,28-diyl, 4-methyl-18-octacosyne-1,28-diyl, 7,14-dimethyl-19-octacosyne-1,28-diyl, 13-ethyl-20-octacosyne-1,28-diyl, 8-methyl-21-octacosyne-1,28-diyl, 11,17-dimethyl-22-octacosyne-1,28-diyl, 10-ethyl-23-octacosyne-1,28-diyl, 9-methyl-24-octacosyne-1,28-diyl, 7,19-dimethyl-25-octacosyne-1,28-diyl, 12-ethyl-26-octacosyne-1,28-diyl, 15-methyl-2-nonacosyne-1,29-diyl, 14-methyl-3-nonacosyne-1,29-diyl, 12-methyl-4-nonacosyne-1,29-diyl, 13-methyl-5-nonacosyne-1,29-diyl, 11-methyl-6-nonacosyne-1,29-diyl, 10-methyl-7-nonacosyne-1,29-diyl, 25-methyl-8-nonacosyne-1,29-diyl, 24-methyl-9-nonacosyne-1,29-diyl, 23-methyl-10-nonacosyne-1,29-diyl, 22-methyl-11-nonacosyne-1,29-diyl, 21-methyl-12-nonacosyne-1,29-diyl, 20-methyl-13-nonacosyne-1,29-diyl, 19-methyl-14-nonacosyne-1,29-diyl, 18-methyl-15-nonacosyne-1,29-diyl, 27-methyl-16-nonacosyne-1,29-diyl, 26-methyl-17-nonacosyne-1,29-diyl, 25-methyl-18-nonacosyne-1,29-diyl, 24-methyl-19-nonacosyne-1,29-diyl, 23-methyl-20-nonacosyne-1,29-diyl, 20-methyl-21-nonacosyne-1,29-diyl, 19-methyl-22-nonacosyne-1,29-diyl, 18-methyl-23-nonacosyne-1,29-diyl, 17-methyl-24-nonacosyne-1,29-diyl, 16-methyl-25-nonacosyne-1,29-diyl, 6-methyl-26-nonacosyne-1,29-diyl and 5-methyl-27-nonacosyne-1,29-diyl.

Typically, G is preferably an optionally substituted linear $C_1$–$C_{30}$ alkylene group, more preferably an optionally substituted linear $C_2$–$C_{15}$ alkylene group, even more preferably a linear $C_2$–$C_{13}$ alkylene group which may be substituted with a hydroxyl group. Above all, particularly preferred are ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, 2-hydroxypropane-1,3-diyl, 3-hydroxy-octane-1,8-diyl, 3-hydroxynonane-1,9-diyl and 3-hydroxydecane-1,10-diyl. More particularly preferred are linear $C_2$–$C_5$ alkylene groups such as ethane-1,2-diyl, propane-1,3-diyl, butane-1,4-diyl and pentane-1,5-diyl.

The optionally substituted linear or branched $C_2$–$C_{30}$ alkylene group, the optionally substituted linear or branched $C_2$–$C_{30}$ alkenylene group and the optionally substituted linear or branched $C_2$–$C_{30}$ alkynylene group as G are each linked to A and E at their positions 1 and ω, respectively, and vice versa. Preferably, G is linked to A at its position 1 and linked to E at its position ω.

E represents a group selected from the following formulae $E^1$ to $E^{10}$:

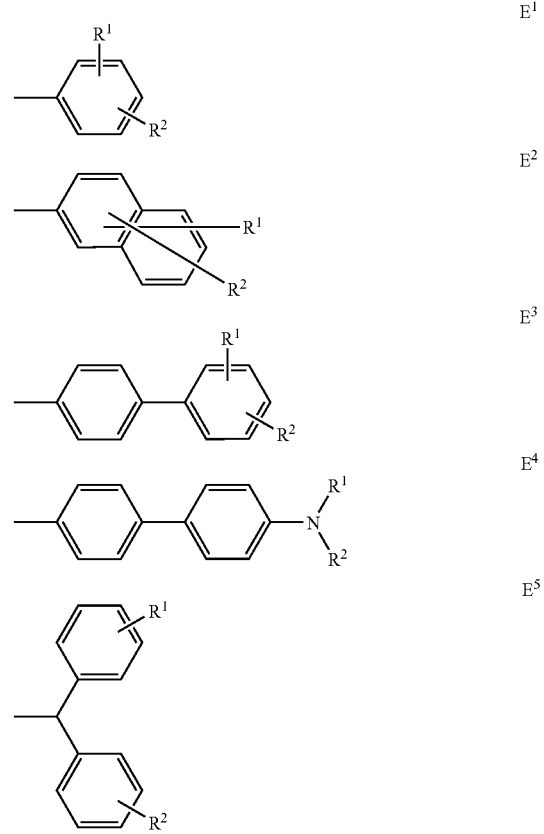

-continued

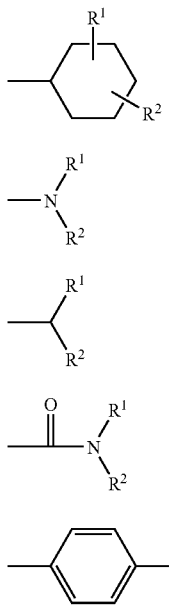

E⁶

E⁷

E⁸

E⁹

E¹⁰

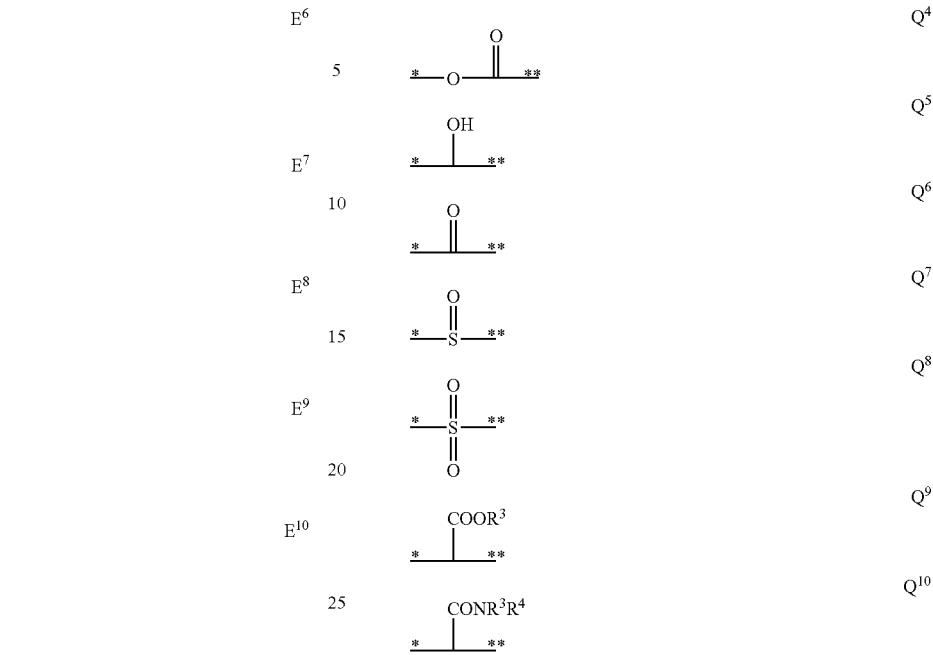

Q⁴

Q⁵

Q⁶

Q⁷

Q⁸

Q⁹

Q¹⁰

(wherein R¹ and R² are as defined above). Above all, E is preferably E¹, E², E³, E⁴ or E¹⁰, more preferably E¹. In a case where E is E¹, E¹ preferably has the substituents R¹ and R² at the meta-positions to the point where E is linked to G. R¹ and R² in formulae E¹ to E¹⁰ may be the same or different.

In general formula (III) defined as R¹ and R², J represents a single bond, a methylene group or —O—, and preferably represents —O—.

G² in general formula (III) represents a single bond, an optionally substituted linear or branched $C_1$–$C_{10}$ alkylene group, an optionally substituted linear or branched $C_2$–$C_{10}$ alkenylene group, or an optionally substituted linear or branched $C_2$–$C_{10}$ alkynylene group, preferably represents an optionally substituted linear or branched $C_1$–$C_{10}$ alkylene group, and more preferably represents a linear $C_1$–$C_5$ alkylene group. By way of typical examples for such groups, appropriate ones can be selected from the specific examples listed for the optionally substituted linear or branched $C_1$–$C_{30}$ alkylene group, the optionally substituted linear or branched $C_2$–$C_{30}$ alkenylene group and the optionally substituted linear or branched $C_2$–$C_{30}$ alkynylene group as G.

Q in general formula (III) represents a single bond or a group selected from the following formulae Q¹ to Q¹⁰:

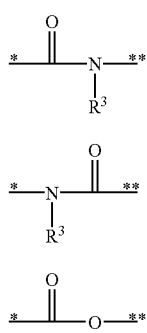

Q¹

Q²

Q³

(wherein R³ and R⁴ are as defined above and * and ** are as illustrated above), and preferably represents Q¹, Q⁷ or Q⁹. Above all, Q is preferably Q¹ in which more preferably R³ is a hydrogen atom. The binding hands marked with * in formulae Q¹ to Q¹⁰ mean that Q is linked to the G² side in general formula (III), while the binding hands marked with ** mean that Q is linked to the Z side in general formula (III). R³ and R⁴ in formulae Q², Q⁹ and Q¹⁰, which are the same or different, each represent a hydrogen atom or a linear or branched $C_1$–$C_{10}$ lower alkyl group, and preferably represent a hydrogen atom.

Z in general formula (III) represents a hydrogen atom, a linear or branched $C_1$–$C_{10}$ alkyl group which may be substituted with a halogen atom, a linear or branched $C_2$–$C_{10}$ alkenyl group which may be substituted with a halogen atom, a linear or branched $C_2$–$C_{10}$ alkynyl group which may be substituted with a halogen atom, or a group of general formula (IV):

$$—O—R^d \qquad (IV)$$

(wherein $R^d$ represents a hydrogen atom or a protecting group for a hydroxyl group). Examples of a halogen atom in the linear or branched $C_1$–$C_{10}$ alkyl group which may be substituted with a halogen atom, the linear or branched $C_2$–$C_{10}$ alkenyl group which may be substituted with a halogen atom and the linear or branched $C_2$–$C_{10}$ alkynyl group which may be substituted with a halogen atom as Z include fluorine, chlorine, bromine and iodine, with fluorine being preferred. When substituted, Z contains 1 to 10 halogen atoms, preferably 3 to 9 halogen atoms, and most preferably 5 halogen atoms. Preferably, all hydrogen atoms on a certain carbon atom are substituted with halogen atoms (e.g., a trihalomethyl group, a 1,1,3,3,3-pentahalopropyl group).

Examples of a linear or branched $C_1$–$C_{10}$ alkyl group in the linear or branched $C_1$–$C_{10}$ alkyl group which may be substituted with a halogen atom as Z include:

linear alkyl groups such as methyl, ethyl, n-propyl, n-butyl, n-pentyl, n-hexyl, n-heptyl, n-octyl, n-nonyl and n-decyl; and branched alkyl groups such as 1-methylethyl, 1-methylpropyl, 2-methylpropyl, 1-methylbutyl, 2-methylbutyl, 3-methylbutyl, 1,1-dimethylpropyl, 1,2-dimethylpropyl, 2,2-dimethylpropyl, 1-ethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1-methylhexyl, 2-methylhexyl, 3-methylhexyl, 4-methylhexyl, 5-methylhexyl, 1-ethylpentyl, 2-ethylpentyl, 3-ethylpentyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 3,3-dimethylpentyl, 3,4-dimethylpentyl, 4,4-dimethylpentyl, 1-propylbutyl, 1-ethyl-1-methylbutyl, 1-ethyl-2-methylbutyl, 1-ethyl-3-methylbutyl, 2-ethyl-1-methylbutyl, 2-ethyl-2-methylbutyl, 2-ethyl-3-methylbutyl, 1,1,2-trimethylbutyl, 1,1,3-trimethylbutyl, 1,2,2-trimethylbutyl, 1,2,3-trimethylbutyl, 1,3,3-trimethylbutyl, 2,2,3-trimethylbutyl, 2,3,3-trimethylbutyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 4-ethylhexyl, 1,1-dimethylhexyl, 1,2-dimethylhexyl, 1,3-dimethylhexyl, 1,4-dimethylhexyl, 1,5-dimethylhexyl, 2,2-dimethylhexyl, 2,3-dimethylhexyl, 2,4-dimethylhexyl, 2,5-dimethylhexyl, 3,3-dimethylhexyl, 3,4-dimethylhexyl, 3,5-dimethylhexyl, 4,4-dimethylhexyl, 4,5-dimethylhexyl, 5,5-dimethylhexyl, 1-propylpentyl, 2-propylpentyl, 1-ethyl-1-methylpentyl, 1-ethyl-2-methylpentyl, 1-ethyl-3-methylpentyl, 1-ethyl-4-methylpentyl, 2-ethyl-1-methylpentyl, 2-ethyl-2-methylpentyl, 2-ethyl-3-methylpentyl, 2-ethyl-4-methylpentyl, 3-ethyl-1-methylpentyl, 3-ethyl-2-methylpentyl, 3-ethyl-3-methylpentyl, 3-ethyl-4-methylpentyl, 1,1,2-trimethylpentyl, 1,1,3-trimethylpentyl, 1,1,4-trimethylpentyl, 1,2,2-trimethylpentyl, 1,2,3-trimethylpentyl, 1,2,4-trimethylpentyl, 1,3,3-trimethylpentyl, 1,3,4-trimethylpentyl, 1,4,4-trimethylpentyl, 2,2,3-trimethylpentyl, 2,2,4-trimethylpentyl, 2,3,3-trimethylpentyl, 2,3,4-trimethylpentyl, 2,4,4-trimethylpentyl, 3,3,4-trimethylpentyl, 3,4,4-trimethylpentyl, 1-methyl-1-propylbutyl, 2-methyl-1-propylbutyl, 3-methyl-1-propylbutyl, 1,1-diethylbutyl, 1,2-diethylbutyl, 2,2-diethylbutyl, 1,2-dimethyl-1-ethylbutyl, 1,3-dimethyl-1-ethylbutyl, 2,2-dimethyl-1-ethylbutyl, 2,3-dimethyl-1-ethylbutyl, 3,3-dimethyl-1-ethylbutyl, 1,1-dimethyl-2-ethylbutyl, 1,2-dimethyl-2-ethylbutyl, 1,3-dimethyl-2-ethylbutyl, 2,3-dimethyl-2-ethylbutyl, 3,3-dimethyl-2-ethylbutyl, 1,1-diethyl-2-methylpropyl, 1-methyloctyl, 2-methyloctyl, 3-methyloctyl, 4-methyloctyl, 5-methyloctyl, 6-methyloctyl, 7-methyloctyl, 1-ethylheptyl, 2-ethylheptyl, 3-ethylheptyl, 4-ethylheptyl, 5-ethylheptyl, 1,1-dimethylheptyl, 1,2-dimethylheptyl, 1,3-dimethylheptyl, 1,4-dimethylheptyl, 1,5-dimethylheptyl, 1,6-dimethylheptyl, 2,2-dimethylheptyl, 2,3-dimethylheptyl, 2,4-dimethylheptyl, 2,5-dimethylheptyl, 2,6-dimethylheptyl, 3,3-dimethylheptyl, 3,4-dimethylheptyl, 3,5-dimethylheptyl, 3,6-dimethylheptyl, 4,4-dimethylheptyl, 4,5-dimethylheptyl, 4,6-dimethylheptyl, 5,5-dimethylheptyl, 5,6-dimethylheptyl, 6,6-dimethylheptyl, 1-propylhexyl, 2-propylhexyl, 3-propylhexyl, 1-ethyl-1-methylhexyl, 1-ethyl-2-methylhexyl, 1-ethyl-3-methylhexyl, 1-ethyl-4-methylhexyl, 1-ethyl-5-methylhexyl, 2-ethyl-1-methylhexyl, 2-ethyl-2-methylhexyl, 2-ethyl-4-methylhexyl, 2-ethyl-5-methylhexyl, 3-ethyl-1-methylhexyl, 3-ethyl-2-methylhexyl, 3-ethyl-3-methylhexyl, 3-ethyl-4-methylhexyl, 3-ethyl-5-methylhexyl, 4-ethyl-1-methylhexyl, 4-ethyl-2-methylhexyl, 4-ethyl-3-methylhexyl, 4-ethyl-4-methylhexyl, 4-ethyl-5-methylhexyl, 1,1,2-trimethylhexyl, 1,1,3-trimethylhexyl, 1,1,4-trimethylhexyl, 1,1,5-trimethylhexyl, 1,2,2-trimethylhexyl, 1,2,3-trimethylhexyl, 1,2,4-trimethylhexyl, 1,2,5-trimethylhexyl, 1,3,3-trimethylhexyl, 1,3,4-trimethylhexyl, 1,3,5-trimethylhexyl, 1,4,4-trimethylhexyl, 1,4,5-trimethylhexyl, 1,5,5-trimethylhexyl, 2,2,3-trimethylhexyl, 2,2,4-trimethylhexyl, 2,2,5-trimethylhexyl, 2,3,3-trimethylhexyl, 2,3,4-trimethylhexyl, 2,3,5-trimethylhexyl, 2,4,4-trimethylhexyl, 2,4,5-trimethylhexyl, 2,5,5-trimethylhexyl, 3,3,4-trimethylhexyl, 3,3,5-trimethylhexyl, 3,4,4-trimethylhexyl, 3,4,5-trimethylhexyl, 3,5,5-trimethylhexyl, 4,4,5-trimethylhexyl, 4,5,5-trimethylhexyl, 1-methyl-nonyl, 2-methyl-nonyl, 3-methyl-nonyl, 4-methyl-nonyl, 5-methyl-nonyl, 6-methyl-nonyl, 7-methyl-nonyl, 8-methyl-nonyl and 9-methyl-nonyl. Preferred are linear $C_3$–$C_{10}$ alkyl groups, and particularly preferred is n-pentyl.

Examples of a linear or branched $C_2$–$C_{10}$ alkenyl group in the linear or branched $C_2$–$C_{10}$ alkenyl group which may be substituted with a halogen atom as Z include:

linear alkenyl groups such as vinyl, 1-propenyl, 2-propenyl, 1-butenyl, 2-butenyl, 3-butenyl, 1,3-butadienyl, 2-pentenyl, 3-pentenyl, 2,4-pentadienyl, 2-hexenyl, 3-hexenyl, 4-hexenyl, 2,4-hexadienyl, 2-heptenyl, 3-heptenyl, 4-heptenyl, 5-heptenyl, 2,4-heptadienyl, 2,5-heptadienyl, 3,5-heptadienyl, 2-octenyl, 3-octenyl, 4-octenyl, 5-octenyl, 6-octenyl, 2,4-octadienyl, 2,5-octadienyl, 2,6-octadienyl, 2,4,6-octatrienyl, 2-nonenyl, 3-nonenyl, 4-nonenyl, 5-nonenyl, 6-nonenyl, 7-nonenyl, 2-decenyl, 3-decenyl, 4-decenyl, 5-decenyl, 6-decenyl, 7-decenyl and 8-decenyl; and branched alkenyl groups such as 1-methylethenyl, 2-methyl-1-propenyl, 2-methyl-2-propenyl, 2-methyl-1-butenyl, 3-methyl-2-butenyl, 2-methyl-3-butenyl, 2,3-dimethyl-1,3-butadienyl, 3-ethyl-2-propenyl, 4-methyl-3-propenyl, 3-methyl-2,4-propadienyl, 3,4-diethyl-2-hexenyl, 4-methyl-3-hexenyl, 2-methyl-4-hexenyl, 3,5-dimethyl-2,4-hexadienyl, 5-ethyl-3-methyl-2-heptenyl, 5-methyl-3-heptenyl, 4-n-propyl-4-heptenyl, 3,6-dimethyl-5-heptenyl, 5-ethyl-2,4-heptadienyl, 2,6-dimethyl-2,5-heptadienyl, 4-ethyl-3,5-heptadienyl, 4,6-dimethyl-2-octenyl, 5-ethyl-3-octenyl, 3-ethyl-4-octenyl, 3-ethyl-5-octenyl, 3,4-dimethyl-6-octenyl, 5-ethyl-2,4-octadienyl, 3-methyl-2,5-octadienyl, 5-ethyl-2,6-octadienyl, 4-methyl-2,4,6-octatrienyl, 5-methyl-2-nonenyl, 6-methyl-3-nonenyl, 7-methyl-4-nonenyl, 3-methyl-5-nonenyl, 4-methyl-6-nonenyl and 3-methyl-7-nonenyl.

Examples of a linear or branched $C_2$–$C_{10}$ alkynyl group in the linear or branched $C_2$–$C_{10}$ alkynyl group which may be substituted with a halogen atom as Z include:

linear alkynyl groups such as ethynyl, 1-propynyl, 2-propynyl, 1-butynyl, 2-butynyl, 3-butynyl, 1,3-butadiynyl, 2-pentynyl, 3-pentynyl, 2,4-pentadiynyl, 2-hexynyl, 3-hexynyl, 4-hexynyl, 2,4-hexadiynyl, 2-heptynyl, 3-heptynyl, 4-heptynyl, 5-heptynyl, 2,4-heptadiynyl, 2,5-heptadiynyl, 3,5-heptadiynyl, 2-octynyl, 3-octynyl, 4-octynyl, 5-octynyl, 6-octynyl, 2,4-octadiynyl, 2,5-octadiynyl, 2,6-octadiynyl, 2,4,6-octatriynyl, 2-nonynyl, 3-nonynyl, 4-nonynyl, 5-nonynyl, 6-nonynyl, 7-nonynyl, 2-decynyl, 3-decynyl, 4-decynyl, 5-decynyl, 6-decynyl, 7-decynyl and 8-decynyl and;

branched alkynyl groups such as 1-methyl-2-propynyl, 3-methyl-1-butynyl, 2-methyl-3-butynyl, 4-methyl-2-pentynyl, 2-methyl-3-pentynyl, 4-ethyl-2-hexynyl, 5-methyl-3-hexynyl, 2-methyl-4-hexynyl, 5-ethyl-6-methyl-2-heptynyl, 5-methyl-3-heptynyl, 3-n-propyl-4-heptynyl, 4,4-dimethyl-5-heptynyl, 6-methyl-2,4-heptadiynyl, 4-methyl-2,5-heptadiynyl, 2-methyl-3,5-heptadiynyl, 6,6-dimethyl-2-octynyl, 6-methyl-3-octynyl, 3-ethyl-4-octynyl, 4-methyl-5-octynyl, 4,8-dimethyl-6-octynyl, 7-methyl-2,4-octadiynyl, 4-methyl-2,5-octadiynyl, 5-ethyl-2,6-octadiynyl, 5-methyl-2-nonynyl, 6-methyl-3-nonynyl, 7-methyl-4-nonynyl, 8-methyl-5-nonynyl, 4-methyl-6-nonynyl and 3-methyl-7-nonynyl.

In a case where Z is —O—$R^d$, $R^d$ represents a hydrogen atom or a protecting group for a hydroxyl group, and preferably represents a hydrogen atom. Examples of a protecting group for a hydroxyl group include the same ones as listed for the protecting group for a hydroxyl group as $R^a$. Preferred and particularly preferred ones are also the same as for $R^a$.

Typically, Z is preferably a linear or branched $C_1$–$C_{10}$ alkyl group which may be substituted with a halogen atom, more preferably a linear or branched $C_3$–$C_{10}$ alkyl group which is substituted with a halogen atom, in particular, a linear or branched $C_3$–$C_8$ alkyl group which is substituted with a fluorine atom, and even more preferably a 4,4,5,5,5-pentafluoropentyl group. In a case where J, $G^2$ and Q simultaneously represent a single bond, Z is not a hydrogen atom.

A compound of general formula (I) wherein Z is —O—$R^d$ (wherein $R^d$ is as defined above) is also useful as an intermediate for compounds of general formula (I) wherein Z is not —O—$R^d$ (wherein $R^d$ is as defined above).

$X^1$ and $X^2$ preferably have such structure that can prevent the folding of helix 12 in the androgen receptor when a compound of general formula (I) binds to the androgen receptor. Specific examples of such structure include 3-{3,5-bis(carbamoylmethoxy)phenyl}propyl, 3-{3,5-bis(pentylcarbamoylmethoxy)phenyl}propyl, 3-{3,5-bis(2-carbamoylethoxy)phenyl}propyl, 3-[3,5-bis{2-(pentylcarbamoyl)ethoxy}phenyl]propyl, 3-{3,5-bis(3-carbamoylpropoxy)phenyl}propyl, 3-[3,5-bis{3-(pentylcarbamoyl)propoxy}phenyl]propyl, 3-{3,5-bis(4-carbamoylbutoxy)phenyl}propyl, 3-[3,5-bis{4-(pentylcarbamoyl)butoxy}phenyl]propyl, 3-{3,5-bis(5-carbamoylpentyloxy)phenyl}propyl and 3-[3,5-bis{5-(pentylcarbamoyl)pentyloxy}phenyl]propyl, with 3-{3,5-bis(carbamoylmethoxy)phenyl}propyl and 3-{3,5-bis(pentylcarbamoylmethoxy)phenyl}propyl being preferred.

Specific examples of a compound represented by general formula (I) include:

17β-hydroxy-7α-[3-{3,5-bis(carbamoylmethoxy)phenyl}propyl]androstan-3-one;
17β-hydroxy-11β-[3-{3,5-bis(carbamoylmethoxy)phenyl}propyl]androstan-3-one;
17β-hydroxy-7α-[3-{3,5-bis(pentylcarbamoylmethoxy)phenyl}propyl]androstan-3-one;
17β-hydroxy-11β-[3-{3,5-bis(pentylcarbamoylmethoxy)phenyl}propyl]androstan-3-one;
17β-hydroxy-7α-[3-{3,5-bis(2-carbamoylethoxy)phenyl}propyl]androstan-3-one;
17β-hydroxy-11β-[3-{3,5-bis(2-carbamoylethoxy)phenyl}propyl]androstan-3-one;
17β-hydroxy-7α-(3-[3,5-bis{2-(pentylcarbamoyl)ethoxy}phenyl]propyl)androstan-3-one;
17β-hydroxy-11β-(3-[3,5-bis{2-(pentylcarbamoyl)ethoxy}phenyl]propyl)androstan-3-one;
17β-hydroxy-7α-[3-{3,5-bis(3-carbamoylpropoxy)phenyl}propyl]androstan-3-one;
17β-hydroxy-11β-[3-{3,5-bis(3-carbamoylpropoxy)phenyl}propyl]androstan-3-one;
17β-hydroxy-7α-(3-[3,5-bis{3-(pentylcarbamoyl)propoxy}phenyl]propyl)androstan-3-one;
17β-hydroxy-11β-(3-[3,5-bis{3-(pentylcarbamoyl)propoxy}phenyl]propyl)androstan-3-one;
17β-hydroxy-7α-[3-{3,5-bis(4-carbamoylbutoxy)phenyl}propyl]androstan-3-one;
17β-hydroxy-11β-[3-{3,5-bis(4-carbamoylbutoxy)phenyl}propyl]androstan-3-one;
17β-hydroxy-7α-(3-[3,5-bis{4-(pentylcarbamoyl)butoxy}phenyl]propyl)androstan-3-one;
17β-hydroxy-11β-(3-[3,5-bis{4-(pentylcarbamoyl)butoxy}phenyl]propyl)androstan-3-one;
17β-hydroxy-7α-[3-{3,5-bis(5-carbamoylpentyloxy)phenyl}propyl]androstan-3-one;
17β-hydroxy-11β-[3-{3,5-bis(5-carbamoylpentyloxy)phenyl}propyl]androstan-3-one;
17β-hydroxy-7α-(3-[3,5-bis{5-(pentylcarbamoyl)pentyloxy}phenyl]propyl)androstan-3-one; and
17β-hydroxy-11β-(3-[3,5-bis{5-(pentylcarbamoyl)pentyloxy}phenyl]propyl)androstan-3-one.

The structures of these compounds will be shown below:

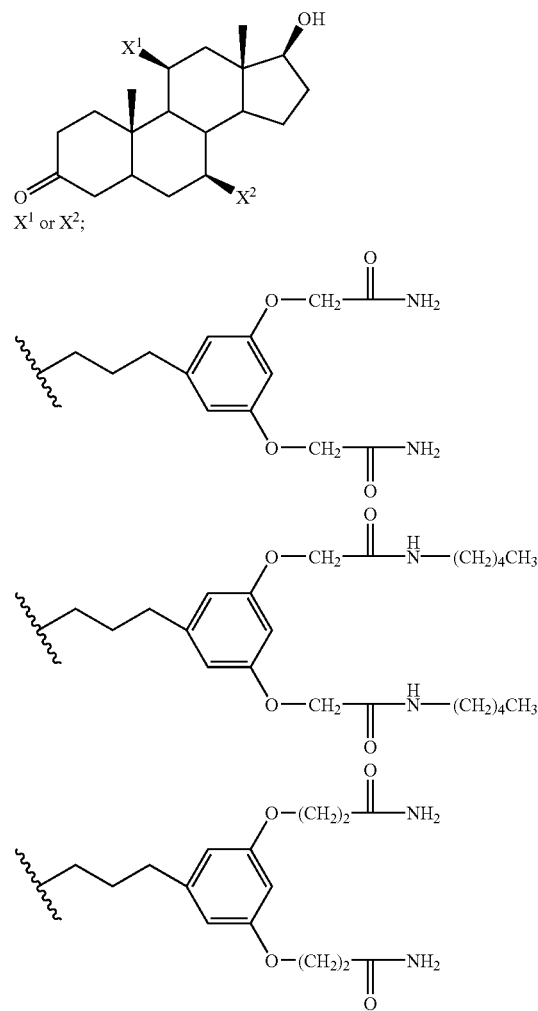

-continued

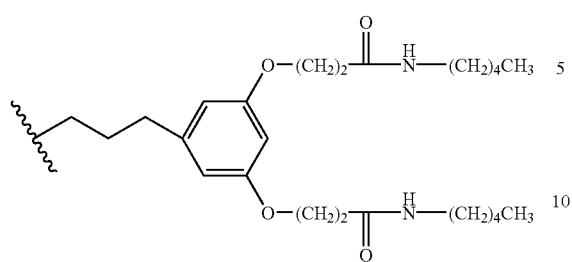

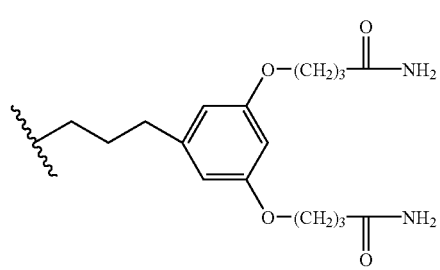

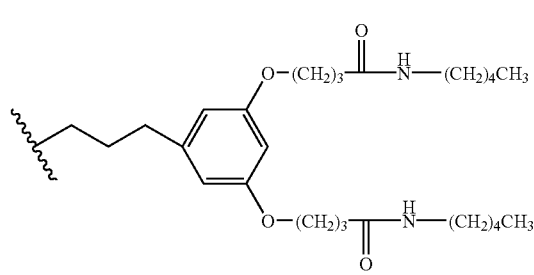

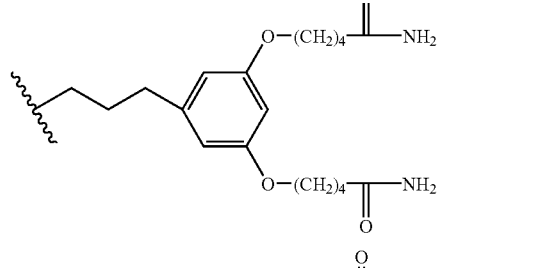

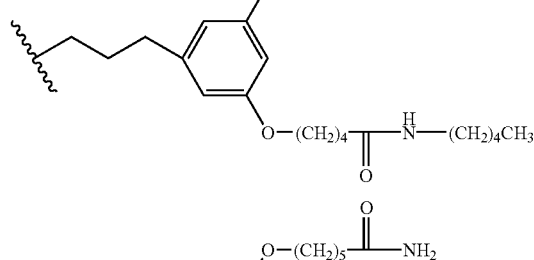

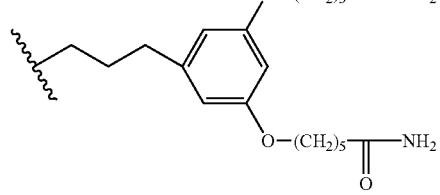

-continued

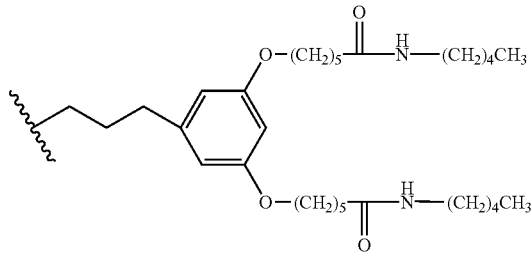

In a case where a compound of general formula (I) has one or more asymmetric carbon atoms in its molecule, all enantiomers having R-configuration and S-configuration with respect to individual asymmetric carbon atoms and all mixtures containing these enantiomers at any ratio are intended to be within the scope of the present invention.

$X^1$ and $X^2$ each preferably represent a group of general formula (V):

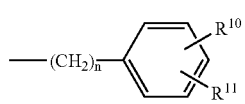 (V)

wherein n represents an integer of 1 to 10, $R^{10}$ represents a hydroxyl group, an alkoxy group or an alkoxycarbonyl group, and $R^{11}$ represents an alkoxy group, an alkoxycarbonyl group or a group of general formula (VI):

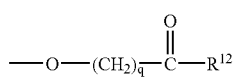 (VI)

wherein q represents an integer of 1 to 10, and $R^{12}$ represents a hydroxyl group or an alkylamino group.

n in general formula (V) is preferably an integer of 1 to 10, more preferably an integer of 1 to 6, and most preferably 3.

The alkoxy group as $R^{10}$ is preferably a $C_1$–$C_6$ alkoxy group, more preferably a $C_1$–$C_3$ alkoxy group, and most preferably a methoxy group.

The alkoxycarbonyl group as $R^{10}$ is preferably a $C_1$–$C_6$ alkoxycarbonyl group, more preferably a $C_1$–$C_3$ alkoxycarbonyl group, and most preferably a methoxycarbonyl group.

Above all, $R^{10}$ is preferably a hydroxyl group, a methoxy group or a methoxycarbonyl group, and more preferably a hydroxyl group.

The alkoxy group as $R^{11}$ is preferably a $C_1$–$C_6$ alkoxy group, more preferably a $C_1$–$C_3$ alkoxy group, and most preferably a methoxy group.

The alkoxycarbonyl group as $R^{11}$ is preferably a $C_1$–$C_6$ alkoxycarbonyl group, more preferably a $C_1$–$C_3$ alkoxycarbonyl group, and most preferably a methoxycarbonyl group.

In a case where $R^{11}$ is a group of general formula (VI), q is preferably an integer of 1 to 10, more preferably an integer of 1 to 6, and most preferably 3.

R¹² in general formula (VI) is preferably an alkylamino group. The alkylamino group as $R^{12}$ refers to a monoalkylamino group or a dialkylamino group, but a dialkylamino group is preferred. An alkyl group in the alkylamino group as $R^{12}$ is preferably a $C_1$–$C_6$ alkyl group, more preferably a $C_1$–$C_3$ alkyl group, and most preferably a methyl group. In particular, the alkylamino group as $R^{12}$ is preferably a dimethylamino group.

Above all, $R^{11}$ is preferably a group of general formula (VI).

As a group of general formula (V), a group represented by the following general formula (VIII) is particularly preferred:

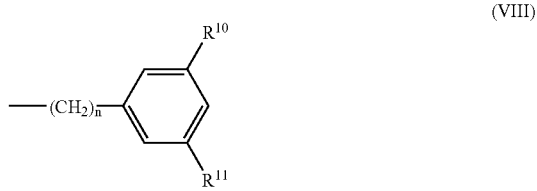

(VIII)

wherein n, $R^{10}$ and $R^{11}$ are as defined above.

As a compound of general formula (I), a compound represented by the following general formula (VII) is particularly preferred:

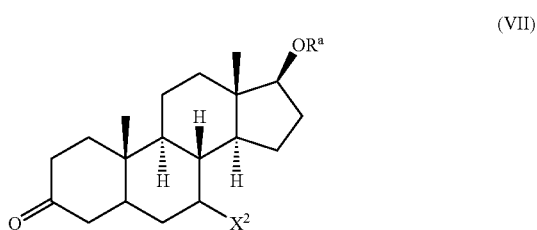

(VII)

wherein $R^a$ and $X^2$ are as defined above.

Specific examples of a preferred compound represented by general formula (I) include:
17β-hydroxy-7α-(3-(3-hydroxy-5-(3-(N,N-dimethylaminocarbonyl)propoxy)phenyl)propyl)-5α-androstan-3-one;
17β-hydroxy-7α-(3-(3,5-dimethoxyphenyl)propyl)-5α-androstan-3-one;
17β-hydroxy-7α-(3-(3-methoxy-4-hydroxyphenyl)propyl)-5α-androstan-3-one;
17β-hydroxy-7α-(3-(3-methoxycarbonyl-4-hydroxyphenyl)propyl)-5α-androstan-3-one;
17β-hydroxy-7α-(3-(3-hydroxy-4-(3-(N,N-dimethylaminocarbonyl)propoxy)phenyl)propyl)-5α-androstan-3-one;
17β-hydroxy-7α-(3-(3-methoxycarbonyl-4-(3-carboxypropoxy)phenyl)propyl)-5α-androstan-3-one; and
17β-hydroxy-7α-(3-(3-methoxycarbonyl-4-(3-(N,N-dimethylaminocarbonyl)propoxy)phenyl)propyl)-5α-androstan-3-one; with 17β-hydroxy-7α-(3-(3-hydroxy-5-(3-(N,N-dimethylaminocarbonyl)propoxy)phenyl)propyl)-5α-androstan-3-one being more preferred.

Speaking of the substance of the present invention that serves as an antagonist against androgen receptor and that is substantially free of agonistic effects, the expression "substantially free of agonistic effects" means that the substance provides a 1- to 5-fold increase in transcriptional activity at a concentration of 0.1 nmol/L to 10 μmol/L, as compared to the value for the absence of the substance, in the androgen receptor gene assay shown below.

Twenty-four hours before transfection, $1.0 \times 10^5$ HeLa cells (purchased from Dainippon Pharmaceutical Co., Ltd.) are cultured in a 12-well microplate containing phenol red-free Dulbecco's Modified Eagle Medium (phenol red-free DMEM) supplemented with charcoal-treated FBS (DCC-FBS; 5%). The HeLa cells are-transfected with 500 ng/well MMTV-Luc vector (a luciferase-reporter plasmid with mouse tumor long terminal repeat containing an androgen-responsive element; a vector prepared by modifying GM-CAT vector purchased from A.T.C.C. (A.T.C.C. No. 67282) to replace its chloramphenicol acetyltransferase gene by the firefly luciferase gene), 100 ng/well pSG5-hAR (a human androgen receptor expression vector carrying the androgen receptor gene under the control of the SV40 promoter) and 5 ng/well Renilla Luc vector (an internal control vector containing the Renilla luciferase gene integrated thereinto). Transfection is performed in phenol red-free DMEM medium using 3 μL/well lipofectamine (Gibco BRL). Nine hours after transfection, the medium is replaced by phenol red-free DMEM/3% DCC-FBS supplemented with 10 μmol/L of the compound represented by general formula (I) or the substance serving as an antagonist against androgen receptor and substantially free of agonistic effects. Forty-eight hours after the replacement of the medium, transcriptional activity is determined by a Dual-Luciferase Reporter Assay System (promega) according to the following equation: (transcriptional activity)=(firefly luciferase activity)/(Renilla luciferase activity). To effect this assay, reference may be made to J. Biol. Chem., vol. 270, p. 19998–20003, 1995.

WO97/49709 discloses hydroxyflutamide (an in vivo active form of flutamide) and bicalutamide as substances serving as antagonists against androgen receptor without having agonistic effects. However, the expression "without having agonistic effects," as used in this document, is defined to mean that the agonist efficacy given by the equation shown below is 0% to 20% at a concentration of 10 μmol/L or above in an androgen reporter gene assay using CV-1 cells; this definition is therefore clearly distinguished from the definition of "free of agonistic effects" in the present invention.

Agonist efficacy (%)=(transcriptional activity induced by a selected non-steroidal compound)/ (the maximum transcriptional activity induced by DHT)×100

In the androgen receptor reporter gene assay used to define the expression "free of agonistic effects" in the present invention, both hydroxyflutamide and bicalutamide were observed to have agonistic effects at a concentration of 10 μmol/L (see Example 1 shown below).

In contrast, the expression "serving as an antagonist," as used herein, means that the transcriptional activity induced by 0.1 nmol/L dihydrotestosterone (DHT) is inhibited to 0% to 50% by the substance of the present invention at any concentration between 0.1 nmol/L and 10 μmol/L in the androgen receptor reporter gene assay shown below.

Twenty-four hours before transfection, $1.0 \times 10^5$ HeLa cells are cultured in a 12-well microplate containing phenol red-free DMEM/5% DCC-FBS. The HeLa cells are transfected with 500 ng/well MMTV-Luc vector, 100 ng/well pSG5-hAR and 5 ng/well Renilla Luc vector. Transfection is performed in phenol red-free DMEM medium using 3

µL/well lipofectamine. Nine hours after transfection, the medium is replaced by phenol red-free DMEM/3% DCC-FBS supplemented with 0.1 nmol/L DHT and 1.0 µmol/L of the compound represented by general formula (I) or the substance serving as an antagonist against androgen receptor and substantially free of agonistic effects. Forty-eight hours after the replacement of the medium, transcriptional activity is determined by a Dual-Luciferase Reporter Assay System according to the following equation: (transcriptional activity)=(firefly luciferase activity)/(Renilla luciferase activity). To effect this assay, reference may be made to J. Biol. Chem., vol. 270, p. 19998–20003, 1995.

As stated above, the present inventors already filed two Japanese patent applications claiming compounds analogous to that of the present invention, i.e., Japanese Patent Application Nos. Hei 11-274956 (filed on Aug. 23, 1999) and Hei 11-338334 (filed on Oct. 22, 1999). When a comparison is made between the compound of the present invention and the compounds disclosed in Japanese Patent Application Nos. Hei 11-274956 and Hei 11-338334, Japanese Patent Application Nos. Hei 11-274956 and Hei 11-338334 recite the following in their claim 1:

"A compound of general formula (I):

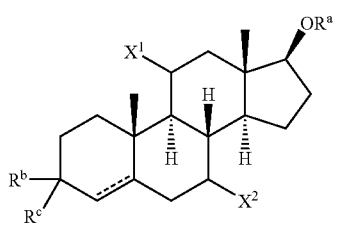

(I)

wherein $X^1$ and $X^2$ independently represent a hydrogen atom or a group of general formula (II):

(II), $R^a$ represents a hydrogen atom or a protecting group for a hydroxyl group, $R^b$ and $R^c$ form an optionally protected —(C=O)— together with the 3-position carbon atom attached to $R^b$ and $R^c$, and the broken line forms a single bond or a double bond together with the solid line, wherein Ar represents a single bond or an aromatic hydrocarbon group, A represents a methylene group or —O—, $R^1$ represents an optionally substituted alkyl group, an optionally substituted alkenyl group or an optionally substituted alkynyl group, provided that $X^1$ and $X^2$ do not simultaneously represent a hydrogen atom, or a pharmaceutically acceptable salt of the compound or a prodrug thereof." In contrast, the present invention is characterized by introducing the side chain "-G-E" instead of the "-$R^1$" in Japanese Patent Application Nos. Hei 11-274956 and Hei 11-338334. The feature "-G-E" of the present invention falls within the widest scope of the definition stating "$R^1$ represents an optionally substituted alkyl group, an optionally substituted alkenyl group or an optionally substituted alkynyl group" in Japanese Patent Application Nos. Hei 11-274956 and Hei 11-338334. By reference to claim 2 and the disclosures of Japanese Patent Application Nos. Hei 11-274956 and Hei 11-338334, the definition of $R^1$ in these applications is considered to be the most relevant to the compound of the present invention when $R^1$ represents -G-E-J-Y-L-Q-Z and J represents an optionally substituted aromatic hydrocarbon group. By taking into account the definition of a substituent on the "optionally substituted aromatic hydrocarbon group," however, the definitions of $R^1$ and $R^2$ as given in the present invention cannot be found in Japanese Patent Application Nos. Hei 11-274956 and Hei 11-338334. Further, the detailed structure and the preparation method of the compound having a terminal-branched side chain as defined in the present invention are neither disclosed nor suggested in any part of Japanese Patent Application No. Hei 11-274956 and Application B.

After filing Japanese Patent Application Nos. Hei 11-274956 and Hei 11-338334, the present inventors made further research efforts on the crystal structure of androgen receptor. As a result, the present inventors found that antagonist activity could be exhibited when helix 12 located at the C-terminal of the androgen receptor ligand-binding domain remained unfolded and dangling, and therefore concluded that a pure antagonist against androgen receptor could be designed by preventing the folding of helix 12.

Hormone-induced transcriptional activation is mediated by nuclear receptors including androgen receptor and starts with binding of hormones to nuclear receptors. Upon binding to hormones, the receptors appear to undergo a conformational change, which allows stimulation of transcription. The mechanism of transcriptional activation by hormones has been studied structurally (Curr. Opinion Cell Biol., vol. 10, 384–391, 1988). As shown in FIG. 1, there are known three possible types for the modes of binding between hormone and nuclear receptor: binding without ligand (apo type); binding between agonist and receptor, which allows stimulation of transcription (agonist type); and binding between antagonist and receptor, which allows substantial inhibition of transcription (antagonist type). The present inventors newly created, as a fourth type, a structure of binding between pure antagonist and receptor, which allows complete inhibition of transcription (pure antagonist type).

Among these modes, the apo type structure has been clarified by X-ray crystal structure analysis on apo-RXRα (see Nature, vol. 375, 377–382, 1995) and helix 12 was found to take an open conformation. In the agonist type structure, helix 12 was found to cover a ligand pocket created by its binding, as studied by X-ray crystal structure analysis on a complex between RARγ and retinoic acid (see Nature, vol. 378, 681–689, 1995). In contrast, the mechanism of inhibition in the antagonist type structure has been clarified by X-ray crystal structure analysis on a complex between estrogen receptor and raloxifene or tamoxifen (see Nature, vol. 389, 753–758, 1997 and Cell, vol. 95, 927–937, 1998). The analysis data indicated that upon binding of raloxifene or tamoxifen, helix 12 was found to occur in the coactivator-binding region composed of helixes 3, 4 and 5. This suggests a mechanism in which helix 12 prevents a coactivator from binding to the region, which in turn inhibits transcriptional activation. Raloxifene and tamoxifen are partial agonists because they stimulate transcription through AF-1 region which is not a ligand-binding region (see Science, vol. 264, 1455–1458, 1994). A structure of the pure antagonist type has not yet been reported. Based upon computer modeling on the structure of a complex between ICI182780 (known as a pure antagonist of estrogen) and estrogen receptor, the present inventors found that helix 12 remained unfixed and flexible in the mode of binding of the pure antagonist type to nuclear receptors, and hence concluded that a pure antagonist against androgen receptor could also be designed by preventing the folding of helix 12 in the androgen receptor. More specifically, the present inventors expected that a compound having a side chain could prevent the folding of helix 12 if the side chain was placed into a position where the folding occurred, and made further research efforts on compounds having such a molecular structure, which finally led to the completion of the invention.

Compounds having such a molecular structure may be represented by general formula (I) wherein a side chain has two branches at its terminal. Upon binding to the androgen receptor, such a branched side chain enables the compounds to prevent the fixing of helix 12 more broadly than compounds having no branched structure. In a case where the branches of the side chain extend in opposite directions, the side chain ensures more positive prevention of the folding of helix 12. This is an entirely new fact which is not disclosed in Japanese Patent Application Nos. Hei 11-274956 and Hei 11-338334, nor in any other prior art documents. Therefore, a more potent pure antagonist activity against androgen receptor is expected than can be offered by the compounds disclosed in Application A and Japanese Patent Application No. Hei 11-338334.

Recently, a report on the crystal structure of androgen receptor has been published, which is entitled "Structural evidence for ligand specificity in the binding domain of the human Androgen receptor: implications for pathogenic gene mutations" (JBC Papers in Press, published on Jun. 5, 2000; Pedro M. Matias et al.).

This report shows the result of a structure analysis performed on a complex between androgen receptor binding domain and a synthetic ligand as well as a complex between progesteron receptor binding domain and a synthetic ligand. The introduction section of this report contains an explanation for the binding modes of the agonist and antagonist types by way of example for helix folding. However, the point of this explanation is directed to the relationship between helix folding and pathological conditions caused by partial mutation of androgen receptors. This report therefore fails to provide any information for obtaining more potent pure antagonist activity against androgen receptor as proposed in the present invention.

The compound of general formula (I) according to the present invention may be obtained as a pharmaceutically acceptable salt. Examples of a pharmaceutically acceptable salt include inorganic acid salts such as hydrochloride, hydrobromate, hydrolodate, sulfate and phosphate; organic acid salts such as formate, acetate, oxalate, maleate, fumarate, methanesulfonate, benzenesulfonate, p-toluenesulfonate, succinate, malonate, citrate, gluconate, mandelate, benzoate, salicylate, trifluoroacetate, tartrate, propionate and glutarate; inorganic base salts such as sodium salt, potassium salt, magnesium salt and zinc salt; and organic base salts such as ammonium salt.

The compound of general formula (I) according to the present invention and a pharmaceutically acceptable salt thereof may be obtained as prodrugs. A prodrug refers to a compound that is rapidly converted in the body through hydrolysis in blood or other mechanisms to yield the compound of general formula (I) or a pharmaceutically acceptable salt thereof or the substance of the present invention that serves as an antagonist against androgen receptor and is substantially free of agonistic effects or a pharmaceutically acceptable salt thereof. T. Higuchi and V. Stella have detailed the concept of prodrugs in "Prodrugs as Novel Delivery Systems," vol. 14 of the A.C.S. Symposium Series, American Chemical Society (1975). Such prodrugs may be active or inactive by themselves, but usually almost inactive. Also, reference may be made to other documents, for example, D. E. V. Wilman, "Prodrugs in Cancer Chemotherapy," Biochemical Society Transactions, vol. 14, pp. 375–382 (615th Meeting, Belfast, 1986) and V. J. Stella et al., "Prodrugs: Chemical Approach to Target-Directed Drug Delivery," Directed Drug Delivery, edited by R. Borchardt et al., pp. 247–267, Humana Press, 1985. In certain cases where a compound of general formula (I) has a —COOH moiety, specific examples of its prodrug include ester, carbonate and carbamate.

The compound of general formula (I) according to the present invention can be prepared, for example, according to Procedures A to D shown below which may be partially modified as appropriate for the intended compounds.

In the chemical schemes shown in Procedures A to D, $R^5$ represents a linear or branched $C_1$–$C_{10}$ alkyl group which may be substituted with a halogen group, and preferably represents a 1,1,2,2,3,3,4,4-nonafluorobutyl group or a trifluoromethyl group. $R^6$ represents a halogen atom or $R^5$—S(O)$_2$—O—, and preferably represents a fluorine atom. $R^7$ represents a group such as —MgX, —ZnX or —Sn(R$^8$)$_3$ (wherein $R^8$ represents a linear or branched $C_1$–$C_6$ alkyl group, preferably a n-butyl group), and preferably represents —Sn(R$^8$)$_3$. $R^e$ represents an aralkyl group such as benzyl, preferably a benzyl group. X represents a halogen atom, preferably a bromine atom. $G^3$ represents a linear or branched $C_1$–$C_7$ alkylene group, a linear or branched $C_2$–$C_7$ alkenylene group, or a linear or branched $C_2$–$C_7$ alkynylene group. A wavy line represents a single bond in trans- or cis-configuration, preferably in trans-configuration, with respect to a double bond.

Procedure A is provided for preparing the following compounds 5 to 8:

a compound of general formula (I) wherein $X^2$ is a hydrogen atom, $X^1$ is a group of general formula (II) in β-configuration [wherein Ar is a single bond, A is a methylene group, G is —CH$_2$CH$_2$—, and E is $E^1$ (wherein $R^1$ and $R^2$ are each an —OH substituent at the meta-position to G)], $R^b$ and $R^c$ form 1,3-dioxolane together with the 3-position carbon atom attached to $R^b$ and $R^c$, and the broken line forms a single bond together with the solid line (compound 5);

a compound of general formula (I) wherein $X^2$ is a hydrogen atom, $X^1$ is a group of general formula (II) in β-configuration [wherein Ar is a single bond, A is a methylene group, G is —CH$_2$CH$_2$—, and E is $E^1$ (wherein $R^1$ and $R^2$ are each an —O-G$^2$-COOR$^3$ substituent at the meta-position to G)], $R^b$ and $R^c$ form 1,3-dioxolane together with the 3-position carbon atom attached to $R^b$ and $R^c$, and the broken line forms a single bond together with the solid line (compound 6);

a compound of general formula (I) wherein $X^2$ is a hydrogen atom, $X^1$ is a group of general formula (II) in β-configuration [wherein Ar is a single bond, A is a methylene group, G is —CH$_2$CH$_2$—, and E is $E^1$ (wherein $R^1$ and $R^2$ are each an —O-G$^2$-COOH substituent at the meta-position to G)], $R^a$ is a hydrogen atom, $R^b$ and $R^c$ form —(C=O)— together with the 3-position carbon atom attached to $R^b$ and $R^c$, and the broken line forms a single bond together with the solid line (compound 7); and a compound of general formula (I) wherein $X^2$ is a hydrogen atom, $X^1$ is a group of general formula (II) in β-configuration [wherein Ar is a single bond, A is a methylene group, G is —CH$_2$CH$_2$—, and E is $E^1$ (wherein $R^1$ and $R^2$ are each an —O-G$^2$-CON(R$^3$)-Z substituent at the meta-position to G)], $R^a$ is a hydrogen atom, $R^b$ and $R^c$ form —(C=O)— together with the 3-position carbon atom attached to $R^b$ and $R^c$, and the broken line forms a single bond together with the solid line (compound 8).

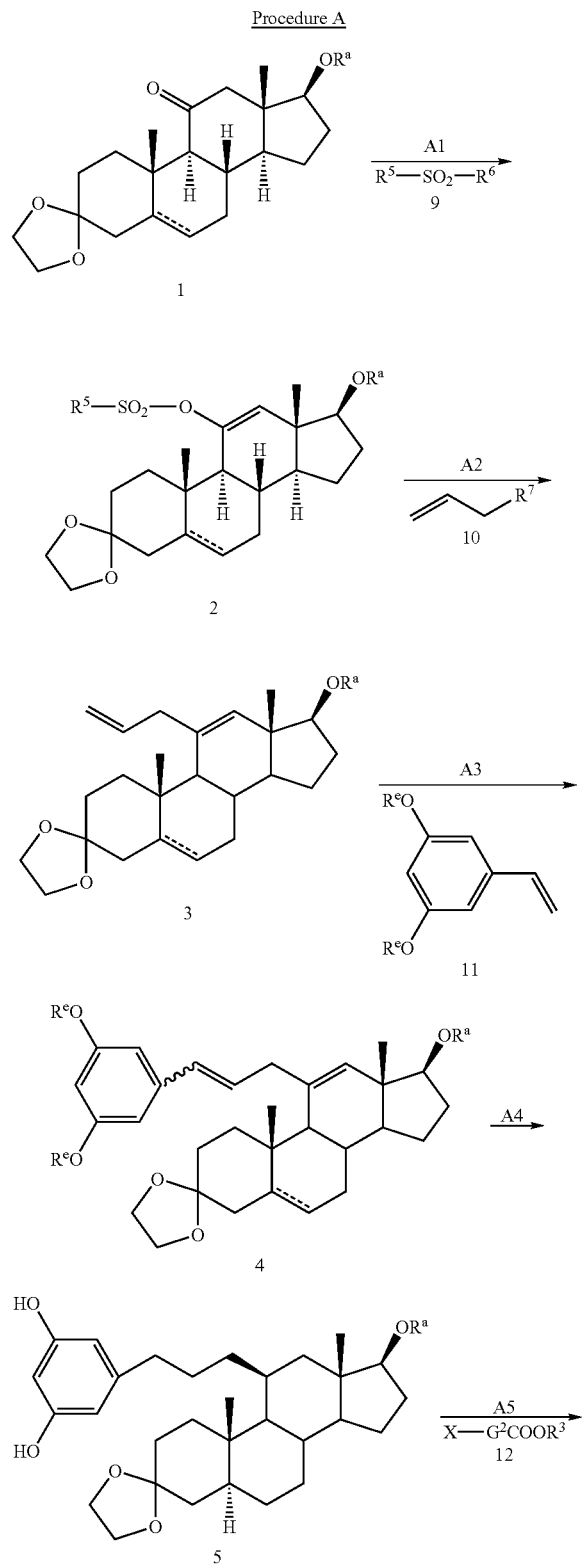

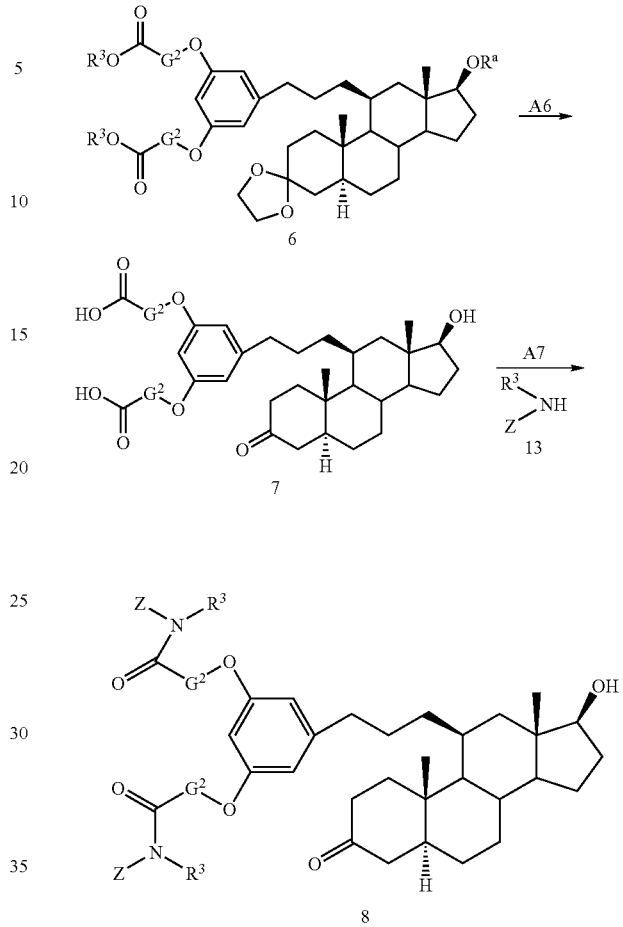

In Step A1, compound 1 is reacted with a base in an inert solvent to give a reactive derivative of compound 1, which in turn is reacted with compound 9 in an inert solvent to prepare compound 2.

Any inert solvent may be used as long as it does not affect the reaction, but preferred may be an ether solvent (e.g., ether, tetrahydrofuran, dioxane, dimethoxyethane), and more preferred is tetrahydrofuran. A base available for use is preferably n-butyllithium, lithium diisopropylamide and the like. The reaction temperature will vary depending on the type of solvent, etc., but is usually −100° C. to 50° C., preferably −78° C. to 30° C. The reaction time will vary depending on the reaction temperature, etc., but is usually 10 minutes to 48 hours, preferably 30 minutes to 24 hours.

In Step A2, compound 2 is reacted with compound 10 in an inert solvent and in the presence of a metal catalyst to prepare compound 3.

Any inert solvent may be used as long as it does not affect the reaction, but preferred may be an ether solvent (e.g., ether, tetrahydrofuran, dioxane, dimethoxyethane), and more preferred is tetrahydrofuran. Examples of a metal catalyst available for use include, but are not limited to, tetrakis(triphenylphosphine)palladium(0), palladium(II) acetate-triphenylphosphine and bis(triphenylphosphine)palladium(II) chloride, with tetrakis(triphenylphosphine)palladium(0) being preferred. The reaction temperature will vary depending on the type of solvent, etc., but is usually 0° C. to 100° C., preferably 100° C. to 80° C. The reaction time will vary depending on the reaction temperature, etc., but is usually 10 minutes to 48 hours, preferably 30 minutes to 24 hours.

In Step A3, compound 3 is reacted with compound 11 in an inert solvent and in the presence of an organometallic catalyst to prepare compound 4.

Any inert solvent may be used as long as it does not affect the reaction, but preferred may be a halogenated solvent (e.g., dichloromethane, chloroform), an ether solvent (e.g., ether, tetrahydrofuran, dioxane, dimethoxyethane) and an aromatic solvent (e.g., benzene, toluene, xylene, quinoline, chlorobenzene), and more preferred are dichloromethane and dimethoxyethane. An organometallic catalyst available for use is preferably benzylidene-bis(tricyclohexylphosphine)-dichlororuthenium. The reaction temperature will vary depending on the type of solvent, etc., but is usually −30° C. to 100° C., preferably 0° C. to 80° C. The reaction time will vary depending on the reaction temperature, etc., but is usually 10 minutes to 48 hours, preferably 30 minutes to 24 hours.

In Step A4, catalytic reduction is performed in an alcohol solvent or an inert solvent, which may be used in combination with each other, to prepare compound 5.

Examples of a solvent available for use include alcohol solvents (e.g., methanol, ethanol, n-propanol, i-propanol, n-butanol, s-butanol, t-butanol, pentanol, hexanol, cyclopropanol, cyclobutanol, cyclopentanol, cyclohexanol, ethylene glycol, 1,3-propanediol, 1,4-butanediol, 1,5-pentanediol), ether solvents (e.g., ether, tetrahydrofuran, dioxane, dimethoxyethane), aromatic solvents (e.g., benzene, toluene, xylene, quinoline, chlorobenzene), halogenated solvents (e.g., dichloromethane, chloroform, carbon tetrachloride), cyclohexane, dimethyl sulfoxide, dimethylacetamide, dimethylimidazolidinone, dimethylformamide, N-methylpyrrolidone, ethyl acetate, acetonitrile, nitromethane and acetic acid. Preferred are ethanol, dioxane, benzene, ethyl acetate and acetic acid.

The catalytic reduction may be performed under homogeneous conditions such as hydrogen-chlorotris(triphenylphosphine)rhodium(I), hydrogen-chlorotris(triparatolylphosphine)rhodium(I), hydrogen-chlorotris(triparamethoxyphenylphosphine)rhodium(I), hydrogen-hydridecarbonyltris(triphenylphosphine)rhodium(I), hydrogen-rhodium(II) acetate, hydrogen-ruthenium(II) acetate, hydrogen-chlorohydridetris(triphenylphosphine)ruthenium(II), hydrogen-carboxylatehydridetris(triphenylphosphine)ruthenium(II), hydrogen-hydridecarbonyltris(triphenylphosphine)iridium(I), hydrogen-platinum(II)-tin chloride complex, hydrogen-pentacyanocobalt(II) complex, hydrogen-tricyanobipyridineocobalt(II) complex, hydrogen-bis(dimethylglyoximate)cobalt(II) complex, hydrogen-methyl benzoate-tricarbonylchromium complex, hydrogen-bis(tricarbonylcyclopentadienylchromium), hydrogen-pentacarbonyliron, hydrogen-bis(cyclopentadienyl)dicarbonyltitanium, hydrogen-hydridecarbonylcobalt complex, hydrogen-octacarbonyldicobalt, hydrogen-hydridecarbonylrhodium, hydrogen-chromium(III)acetylacetonate-triisobutylaluminum, hydrogen-cobalt(II)acetylacetonate-triisobutylaluminum and hydrogen-nickel(II)-2-hexanoate-triethylaluminum, or under heterogeneous conditions such as hydrogen-platinum dioxide, hydrogen-platinum/carbon, hydrogen-palladium/carbon, hydrogen-palladium hydroxide/carbon, hydrogen-palladium/barium sulfate, hydrogen-palladium/calcium carbonate, hydrogen-Raney Nickel, hydrogen-copper chromite, hydrogen-rhodium/carbon, hydrogen-rhodium/alumina, hydrogen-ruthenium dioxide, hydrogen-ruthenium/carbon and hydrogen-iridium black. Preferably, the catalytic reduction is performed under hydrogen-palladium/carbon or hydrogen-iridium black.

The reaction temperature is usually 0° C. to 100° C., preferably 0° C. to 60° C. The reaction time will vary depending on the reaction temperature, etc., but is usually 10 minutes to 100 hours, preferably 10 hours to 96 hours.

In Step A5, compound 5 is reacted with a base in an inert solvent, either alone or in combination, to give a salt of compound 5, which in turn is reacted with compound 12 in an inert solvent to prepare compound 6.

Any inert solvent may be used as long as it does not affect the reaction. Examples include halogenated solvents (e.g., dichloromethane, chloroform, carbon tetrachloride), ether solvents (e.g., ether, tetrahydrofuran, dioxane, dimethoxyethane), aromatic solvents (e.g., benzene, toluene, xylene, quinoline, chlorobenzene), cyclohexane, dimethyl sulfoxide, dimethylacetamide, dimethylimidazolidinone, dimethylformamide, N-methylpyrrolidone and water. Preferred are ether solvents (e.g., ether, tetrahydrofuran, dioxane, dimethoxyethane), dimethyl sulfoxide, dimethylacetamide, dimethylimidazolidinone, dimethylformamide and N-methylpyrrolidone. Examples of a base available for use include metal hydrides (e.g., sodium hydride, potassium hydride, calcium hydride), alkyllithiums (e.g., methyllithium, ethyllithium, n-butyllithium, t-butyllithium), metal hydroxides (e.g., lithium hydroxide, sodium hydroxide, potassium hydroxide, calcium hydroxide, barium hydroxide, cesium hydroxide), carbonates (e.g., potassium carbonate, sodium carbonate), metal amides (e.g., sodium amide, potassium bistrimethylsilylamide, sodium bistrimethylsilylamide, lithium diisopropylamide), amines (e.g., triethylamine, diisopropylethylamine, 1,8-diazabicyclo[5.4.0]-7-undecene, pyridine, dimethylaminopyridine, pyrazine), sodium tetraborate, sodium iodide, lithium hexamethyldisilazide, sodium hexamethyldisilazide and potassium hexamethyldisilazide. Preferred are metal hydrides (e.g., sodium hydride, potassium hydride, calcium hydride) and carbonates (e.g., potassium carbonate, sodium carbonate). The reaction temperature will vary depending on the type of solvent, etc., but is usually −30° C. to 100° C., preferably 0° C. to 70° C. The reaction time will vary depending on the reaction temperature, etc., but is usually 10 minutes to 48 hours, preferably 30 minutes to 24 hours.

In Step A6, compound 6 is reacted with an acid in an aqueous solvent to prepare compound 7.

Any aqueous solvent may be used as long as it does not affect the reaction. Examples include combinations of water and an ether solvent (e.g., ether, tetrahydrofuran, dioxane), an alcohol solvent (e.g., methanol, ethanol) or a ketone solvent (e.g., acetone), with aqueous acetone being preferred.

Examples of an acid available for use include inorganic acids (e.g., hydrochloric acid, hydrobromic acid, hydroiodic acid, sulfuric acid, phosphoric acid) and organic acids (e.g., acetic acid, p-toluenesulfonic acid, pyridinium-p-toluenesulfonate), with hydrochloric acid being preferred. The reaction temperature will vary depending on the type of solvent, etc., but is usually 0° C. to 100° C., preferably 30° C. to 80° C. The reaction time will vary depending on the reaction temperature, etc., but is usually 15 minutes to 24 hours, preferably 30 minutes to 10 hours.

In Step A7, compound 7 or a reactive derivative thereof (acid halides, mixed acid anhydrides, or active esters) is reacted with compound 13 or an acid addition salt thereof in an inert solvent to prepare compound 8.

This reaction may be accomplished by the acid halide method, the mixed acid anhydride method, the active ester method or the condensation method. The acid halide method involves reacting compound 7 with a halogenating agent (e.g., thionyl chloride, oxalyl chloride, phosphorus pentachloride) in an inert solvent to prepare an acid halide, which in turn is reacted with compound 13 or an acid addition salt thereof in an inert solvent and in the presence or absence of a base, preferably in the presence of a base. Examples of a base available for use include organic amines (e.g., triethylamine, N-methylmorpholine, pyridine, 4-dimethylaminopyridine), alkali metal bicarbonates (e.g., sodium bicarbonate, potassium bicarbonate) and alkali metal carbonates (e.g., sodium carbonate, potassium carbonate), with organic amines (particularly triethylamine) being preferred.

Any inert solvent may be used as long as it does not affect the reaction. Examples include hydrocarbon solvents (e.g., hexane, cyclohexane, benzene, toluene, xylene), halogenated solvents (e.g., dichloromethane, 1,2-dichloroethane, carbon tetrachloride), ether solvents (e.g., ether, tetrahydrofuran, dioxane), ketone solvents (e.g., acetone), amide solvents (e.g., N,N-dimethylacetamide, N,N-dimethylformamide, N-methyl-2-pyrrolidone) and sulfoxide solvents (e.g., dimethyl sulfoxide). Preferred are hydrocarbon solvents, halogenated solvents or ether solvents, and more preferred are ether solvents (particularly tetrahydrofuran). Although the reaction temperature will vary depending on the type of solvent, etc., the reaction between a halogenating agent and compound 7 is usually performed at −20° C. to 150° C., preferably at −10° C. to 50° C., while the reaction between the resulting acid halide and compound 13 or an acid addition salt thereof is usually performed at −20° C. to 150° C., preferably at 0° C. to 100° C. The reaction time will vary depending on the reaction temperature, etc., but is usually 15 minutes to 24 hours, preferably 30 minutes to 15 hours.

The mixed acid anhydride method involves reacting compound 7 with a $C_1$–$C_6$ alkyl halogenocarbonate (wherein a $C_1$–$C_6$ alkyl refers to a linear or branched $C_1$–$C_6$ alkyl group), a di-$C_1$–$C_6$ alkyl cyanophosphate or a diaryl phosphoryl azide to prepare a mixed acid anhydride, which in turn is reacted with compound 13 or an acid addition salt thereof. The reaction for preparing a mixed acid anhydride is accomplished by reacting compound 7 with a $C_1$–$C_6$ alkyl halogenocarbonate (e.g., methyl chlorocarbonate, ethyl chlorocarbonate, isobutyl chlorocarbonate, hexyl chlorocarbonate, preferably ethyl chlorocarbonate or isobutyl chlorocarbonate), a di-$C_1$–$C_6$ alkyl cyanophosphate (e.g., dimethyl cyanophosphate, diethyl cyanophosphate, dihexyl cyanophosphate) or a di-$C_1$–$C_6$ alkylaryl phosphoryl azide (e.g., diphenyl phosphoryl azide, di-(p-nitrophenyl) phosphoryl azide, dinaphthyl phosphoryl azide, preferably diphenyl phosphoryl azide). Preferably, the reaction is performed in an inert solvent and in the presence of a base.

The base and inert solvent used in this reaction are the same as used in the acid halide method mentioned above. The reaction temperature will vary depending on the type of solvent, etc., but is usually −20° C. to 50° C., preferably 0° C. to 30° C. The reaction time will vary depending on the reaction temperature, etc., but is usually 15 minutes to 24 hours, preferably 30 minutes to 15 hours.

The reaction between a mixed acid anhydride and compound 13 or an acid addition salt thereof may be performed in an inert solvent and in the presence or absence of a base, preferably in the presence of a base. The base and inert solvent used in this reaction are the same as used in the acid halide method mentioned above. The reaction temperature will vary depending on the type of solvent, etc., but is usually −20° C. to 50° C., preferably 0° C. to 30° C. The reaction time will vary depending on the reaction temperature, etc., but is usually 15 minutes to 24 hours, preferably 30 minutes to 15 hours. In a case where a di-$C_1$–$C_6$ alkyl cyanophosphate or a di-$C_1$–$C_6$ alkylaryl phosphoryl azide is used in this method, compound 7 may be directly reacted with compound 13 or an acid addition salt thereof in the presence of a base.

The active ester method involves reacting compound 7 with an active esterifying agent (e.g., a N-hydroxy compound such as N-hydroxysuccinimide or N-hydroxybenzotriazole) in the presence of a condensing agent (e.g., dicyclohexylcarbodiimide, carbonyldiimidazole) to prepare an active ester, which in turn is reacted with compound 13 or an acid addition salt thereof. The reaction for preparing an active ester is preferably performed in an inert solvent. Examples of an inert solvent available for use include ether solvents (e.g., ether, tetrahydrofuran, dioxane, dimethoxyethane), halogenated solvents (e.g., dichloromethane, chloroform, carbon tetrachloride), dimethylformamide, ethyl acetate and acetonitrile, with dichloromethane, acetonitrile and ethyl acetate being preferred. Although the reaction temperature will vary depending on the type of solvent, etc., the active esterification is usually performed at −20° C. to 50° C., preferably at −10° C. to 30° C., while the reaction between the resulting active ester compound and compound 13 or an acid addition salt thereof is usually performed at −20° C. to 50° C., preferably at −10° C. to 30° C. The reaction time will vary depending on the reaction temperature, etc., but is usually 15 minutes to 24 hours, preferably 30 minutes to 15 hours, for both reactions.

The condensation method involves directly reacting compound 7 with compound 13 or an acid addition salt thereof in the presence of a condensing agent such as dicyclohexylcarbodiimide, carbonyldiimidazole or 1-(N,N-dimethylaminopropyl)-3-ethylcarbodiimide hydrochloride. This reaction may be performed in the same manner as used for active esterification.

Procedure B is provided for preparing the following compounds 14 to 18:

a compound of general formula (I) wherein $X^2$ is a hydrogen atom, $X^1$ is a group of general formula (II) in β-configuration [wherein Ar is a single bond, A is a methylene group, G is —$CH_2CH_2$—, and E is $E^1$ (wherein $R^1$ and $R^2$ are each an —O—$CH_2CH$=$CH_2$ substituent at the meta-position to G)], $R^b$ and $R^c$ form 1,3-dioxolane together with the 3-position carbon atom attached to $R^b$ and $R^c$, and the broken line forms a single bond together with the solid line (compound 14);

a compound of general formula (I) wherein $X^2$ is a hydrogen atom, $X^1$ is a group of general formula (II) in β-configuration [wherein Ar is a single bond, A is a methylene group, G is —$CH_2CH_2$—, and E is $E^1$ (wherein $R^1$ and $R^2$ are each an —O—$CH_2CH$=$CH$-$G^3$-$COOR^3$ substituent at the meta-position to G)], $R^b$ and $R^c$ form 1,3-dioxolane together with the 3-position carbon atom attached to $R^b$ and $R^c$, and the broken line forms a single bond together with the solid line (compound 15);

a compound of general formula (I) wherein $X^2$ is a hydrogen atom, $X^1$ is a group of general formula (II) in β-configuration [wherein Ar is a single bond, A is a methylene group, G is —$CH_2CH_2$—, and E is $E^1$ (wherein $R^1$ and $R^2$ are each an —O—$CH_2CH_2CH_2$-$G^3$-$COOR^3$ substituent at the meta-position to G)], $R^b$ and $R^c$ form 1,3-dioxolane together with the 3-position carbon atom attached to $R^b$ and $R^c$, and the broken line forms a single bond together with the solid line (compound 16);

a compound of general formula (I) wherein $X^2$ is a hydrogen atom, $X^1$ is a group of general formula (II) in β-configuration [wherein Ar is a single bond, A is a methylene group, G is —CH$_2$CH$_2$—, and E is $E^1$ (wherein $R^1$ and $R^2$ are each an —O—CH$_2$CH$_2$CH$_2$-G$^3$-COOH substituent at the meta-position to G)], $R^a$ is a hydrogen atom, $R^b$ and $R^c$ form —(C=O)— together with the 3-position carbon atom attached to $R^b$ and $R^c$, and the broken line forms a single bond together with the solid line (compound 17); and a compound of general formula (I) wherein $X^2$ is a hydrogen atom, $X^1$ is a group of general formula (II) in β-configuration [wherein Ar is a single bond, A is a methylene group, G is —CH$_2$CH$_2$—, and E is $E^1$ (wherein $R^1$ and $R^2$ are each an —O—CH$_2$CH$_2$CH$_2$-G$^3$-CON($R^3$)—Z substituent at the meta-position to G)], $R^a$ is a hydrogen atom, $R^b$ and $R^c$ form —(C=O)— together with the 3-position carbon atom attached to $R^b$ and $R^c$, and the broken line forms a single bond together with the solid line (compound 18).

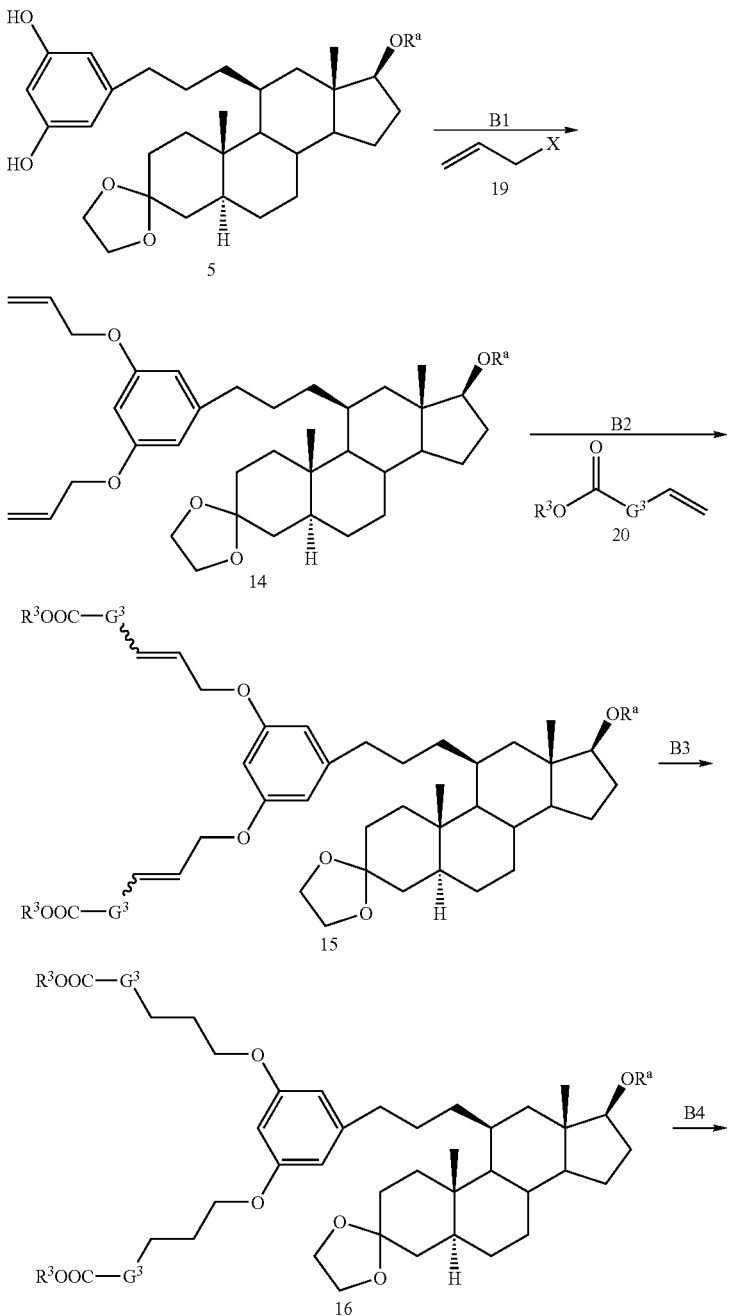

Procedure B

-continued

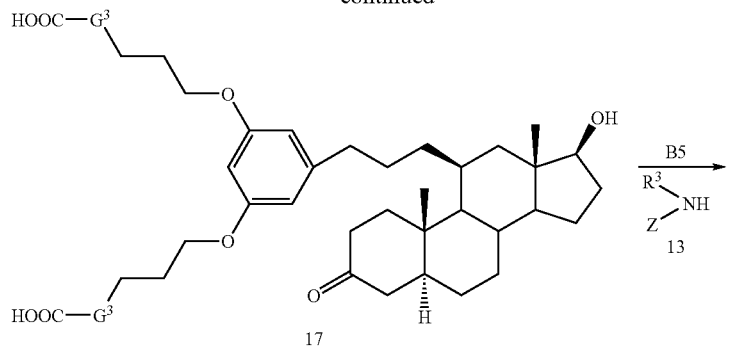

17

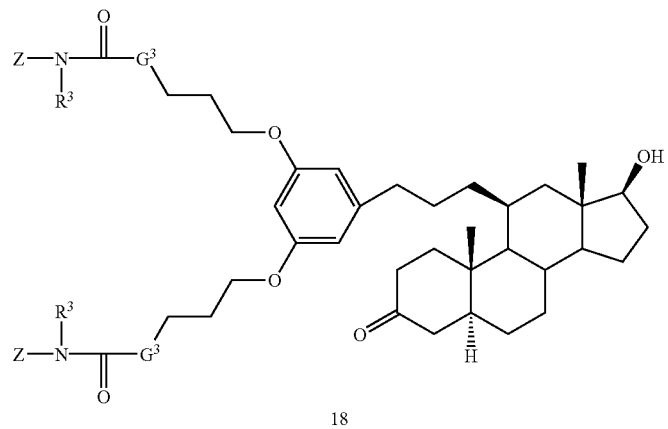

18

In Step B1, compound 5 is reacted with a base in an inert solvent, either alone or in combination, to give a salt of compound 5, which in turn is reacted with compound 19 in an inert solvent to prepare compound 14. This step may be performed in the same manner as Step A5 in Procedure A mentioned above.

In Step B2, compound 14 is reacted with compound 20 in an inert solvent and in the presence of an organometallic catalyst to prepare compound 15. This step may be performed in the same manner as Step A3 in Procedure A mentioned above.

In Step B3, catalytic reduction is performed in an alcohol solvent or an inert solvent to prepare compound 16.

Examples of a solvent available for use include alcohol solvents (e.g., methanol, ethanol, n-propanol, i-propanol, n-butanol, s-butanol, t-butanol, pentanol, hexanol, cyclopropanol, cyclobutanol, cyclopentanol, cyclohexanol, ethylene glycol, 1,3-propanediol, 1,4-butanediol, 1,5-pentanediol), ether solvents (e.g., ether, tetrahydrofuran, dioxane, dimethoxyethane), aromatic solvents (e.g., benzene, toluene, xylene, quinoline, chlorobenzene), halogenated solvents (e.g., dichloromethane, chloroform, carbon tetrachloride), cyclohexane, dimethyl sulfoxide, dimethylacetamide, dimethylimidazolidinone, dimethylformamide, N-methylpyrrolidone, ethyl acetate, acetonitrile and nitromethane. Preferred are ethanol, dioxane, benzene and ethyl acetate.

The catalytic reduction may be performed under homogeneous conditions such as hydrogen-chlorotris(triphenylphosphine)rhodium(I), hydrogen-chlorotris(triparatolylphosphine)rhodium(I), hydrogen-chlorotris(triparamethoxyphenylphosphine)rhodium(I), hydrogen-hydridecarbonyltris(triphenylphosphine)rhodium(I), hydrogen-rhodium(II) acetate, hydrogen-ruthenium(II) acetate, hydrogen-chlorohydridetris(triphenylphosphine)ruthenium(II), hydrogen-carboxylatehydridetris(triphenylphosphine)ruthenium(II), hydrogen-hydridecarbonyltris (triphenylphosphine)iridium(I), hydrogen-platinum(II)-tin chloride complex, hydrogen-pentacyanocobalt(II) complex, hydrogen-tricyanobipyridineocobalt(II) complex, hydrogen-bis(dimethylglyoximate)cobalt(II) complex, hydrogen-methyl benzoate-tricarbonylchromium complex, hydrogen-bis (tricarbonylcyclopentadienylchromium), hydrogen-pentacarbonyliron, hydrogen-bis(cyclopentadienyl) dicarbonyltitanium, hydrogen-hydridecarbonylcobalt complex, hydrogen-octacarbonyldicobalt, hydrogen-hydridecarbonylrhodium, hydrogen-chromium(III)acetylacetonate-triisobutylaluminum, hydrogen-cobalt(II)acetylacetonate-triisobutylaluminum and hydrogen-nickel(II)-2-hexanoate-triethylaluminum, or under heterogeneous conditions such as hydrogen-platinum dioxide, hydrogen-platinum/carbon, hydrogen-palladium/carbon, hydrogen-palladium hydroxide/carbon, hydrogen-palladium/barium sulfate, hydrogen-palladium/calcium carbonate, hydrogen-Raney Nickel, hydrogen-copper chromite, hydrogen-rhodium/carbon, hydrogen-rhodium/alumina, hydrogen-ruthenium dioxide, hydrogen-ruthenium/carbon and hydrogen-iridium black. Preferably, the catalytic reduction is performed under hydrogen-palladium/carbon or hydrogen-palladium hydroxide/carbon.

The reaction temperature is usually 0° C. to 100° C., preferably 0° C. to 60° C. The reaction time will vary depending on the reaction temperature, etc., but is usually 10 minutes to 100 hours, preferably 10 hours to 96 hours.

In Step B4, compound 16 is reacted with an acid in an aqueous solvent to prepare compound 17. This step may be performed in the same manner as Step A6 in Procedure A mentioned above.

In Step B5, compound 17 or a reactive derivative thereof (acid halides, mixed acid anhydrides, or active esters) is reacted with compound 13 or an acid addition salt thereof in an inert solvent to prepare compound 18. This step may be performed in the same manner as Step A7 in Procedure A mentioned above.

Procedure C is provided for preparing the following compounds 23 to 27:

a compound of general formula (I) wherein $X^1$ is a hydrogen atom, $X^2$ is a group of general formula (II) in α-configuration [wherein Ar is a single bond, A is a methylene group, G is —CH=CH—, and E is $E^1$ (wherein $R^1$ and $R^2$ are each an —$OR^e$ substituent at the meta-position to G)], $R^b$ and $R^c$ form —(C=O)— together with the 3-position carbon atom attached to $R^b$ and $R^c$, and the broken line forms a single bond together with the solid line (compound 23);

a compound of general formula (I) wherein $X^1$ is a hydrogen atom, $X^2$ is a group of general formula (II) in α-configuration [wherein Ar is a single bond, A is a methylene group, G is —$CH_2CH_2$—, and E is $E^1$ (wherein $R^1$ and $R^2$ are each an —OH substituent at the meta-position to G)], $R^b$ and $R^c$ form —(C=O)— together with the 3-position carbon atom attached to $R^b$ and $R^c$, and the broken line forms a single bond together with the solid line (compound 24);

a compound of general formula (I) wherein $X^1$ is a hydrogen atom, $X^2$ is a group of general formula (II) in α-configuration [wherein Ar is a single bond, A is a methylene group, G is —$CH_2CH_2$—, and E is $E^1$ (wherein $R^1$ and $R^2$ are each an —O-$G^2$-$COOR^3$ substituent at the meta-position to G)], $R^b$ and $R^c$ form —(C=O)— together with the 3-position carbon atom attached to $R^b$ and $R^c$, and the broken line forms a single bond together with the solid line (compound 25);

a compound of general formula (I) wherein $X^1$ is a hydrogen atom, $X^2$ is a group of general formula (II) in α-configuration [wherein Ar is a single bond, A is a methylene group, G is —$CH_2CH_2$—, and E is $E^1$ (wherein $R^1$ and $R^2$ are each an —O-$G^2$-COOH substituent at the meta-position to G)], $R^a$ is a hydrogen atom, $R^b$ and $R^c$ form —(C=O)— together with the 3-position carbon atom attached to $R^b$ and $R^c$, and the broken line forms a single bond together with the solid line (compound 26); and a compound of general formula (I) wherein $X^1$ is a hydrogen atom, $X^2$ is a group of general formula (II) in α-configuration [wherein Ar is a single bond, A is a methylene group, G is —$CH_2CH_2$—, and E is $E^1$ (wherein $R^1$ and $R^2$ are each an —O-$G^2$-CON($R^3$)-Z substituent at the meta-position to G)], $R^a$ is a hydrogen atom, $R^b$ and $R^c$ form —(C=O)— together with the 3-position carbon atom attached to $R^b$ and $R^c$, and the broken line forms a single bond together with the solid line (compound 27).

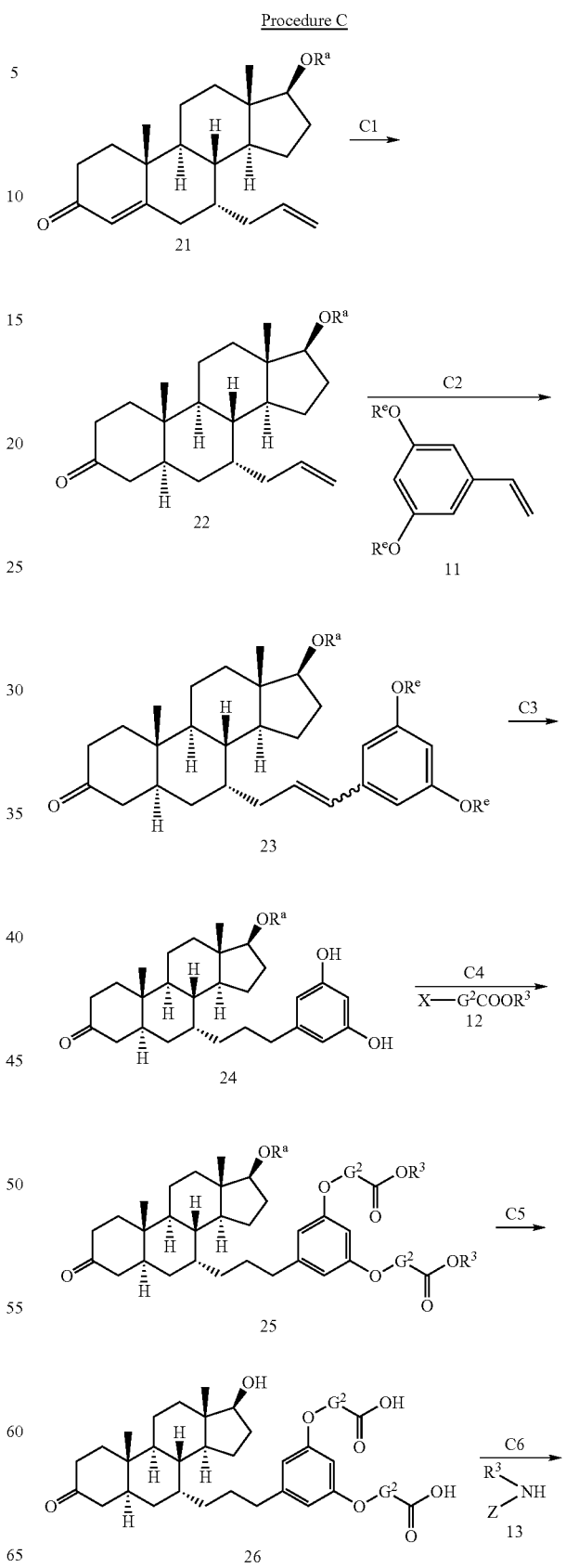

Procedure C

In Step C1, compound 21 is reacted with a reducing agent in an inert solvent to prepare compound 22.

Any inert solvent may be used as long as it does not affect the reaction. Examples include ether solvents such as tetrahydrofuran. Examples of a reducing agent available for use include sodium/liquid ammonia, lithium/liquid ammonia, lithium/methylamine, lithium/ethylamine, lithium/ethylenediamine, sodium/hexamethylphosphoramide-t-butanol, sodium/ethanol, sodium/t-butanol-tetrahydrofuran and sodium/toluene-t-amyl alcohol, with lithium/liquid ammonia being preferred. The reaction temperature will vary depending on the type of solvent, etc., but is usually −100° C. to 20° C., preferably −80° C. to 0° C. The reaction time will vary depending on the reaction temperature, etc., but is usually 10 minutes to 24 hours, preferably 30 minutes to 5 hours.

In Step C2, compound 22 was reacted with compound 11 in an inert solvent and in the presence of an organometallic catalyst to prepare compound 23. This step may be performed in the same manner as Step A3 in Procedure A mentioned above.

In Step C3, catalytic reduction is performed in an alcohol solvent or an inert solvent to prepare compound 24. This step may be performed in the same manner as Step B3 in Procedure B mentioned above.

In Step C4, compound 24 is reacted with a base in an inert solvent, either alone or in combination, to give a salt of compound 24, which in turn is reacted with compound 12 in an inert solvent to prepare compound 25. This step may be performed in the same manner as Step A5 in Procedure A mentioned above.

In Step C5, compound 25 is reacted with an acid in an aqueous solvent to prepare compound 26. This step may be performed in the same manner as Step A6 in Procedure A mentioned above.

In Step C6, compound 26 or a reactive derivative thereof (acid halides, mixed acid anhydrides, or active esters) is reacted with compound 13 or an acid addition salt thereof in an inert solvent to prepare compound 27. This step may be performed in the same manner as Step A7 in Procedure A mentioned above.

Procedure D is provided for preparing the following compounds 28 to 32:

a compound of general formula (I) wherein $X^1$ is a hydrogen atom, $X^2$ is a group of general formula (II) in α-configuration [wherein Ar is a single bond, A is a methylene group, G is —$CH_2CH_2$—, and E is $E^1$ (wherein $R^1$ and $R^2$ are each an —O—$CH_2CH$=$CH_2$ substituent at the meta-position to G)], $R^b$ and $R^c$ form —(C=O)— together with the 3-position carbon atom attached to $R^b$ and $R^c$, and the broken line forms a single bond together with the solid line (compound 28);

a compound of general formula (I) wherein $X^1$ is a hydrogen atom, $X^2$ is a group of general formula (II) in α-configuration [wherein Ar is a single bond, A is a methylene group, G is —$CH_2CH$—, and E is $E^1$ (wherein $R^1$ and $R^2$ are each an —O—$CH_2CH$=$CH$-$G^3$-$COOR^3$ substituent at the meta-position to G)], $R^b$ and $R^c$ form —(C=O)— together with the 3-position carbon atom attached to $R^b$ and $R^c$, and the broken line forms a single bond together with the solid line (compound 29);

a compound of general formula (I) wherein $X^1$ is a hydrogen atom, $X^2$ is a group of general formula (II) in α-configuration [wherein Ar is a single bond, A is a methylene group, G is —$CH_2CH_2$—, and E is $E^1$ (wherein $R^1$ and $R^2$ are each an —O—$CH_2CH_2CH_2$-$G^3$-$COOR^3$ substituent at the meta-position to G)], $R^b$ and $R^c$ form —(C=O)— together with the 3-position carbon atom attached to $R^b$ and $R^c$, and the broken line forms a single bond together with the solid line (compound 30);

a compound of general formula (I) wherein $X^1$ is a hydrogen atom, $X^2$ is a group of general formula (II) in α-configuration [wherein Ar is a single bond, A is a methylene group, G is —$CH_2CH_2$—, and E is $E_1$ (wherein $R^1$ and $R^2$ are each an —O—$CH_2CH_2CH_2$-$G^3$-COOH substituent at the meta-position to G)], $R^a$ is a hydrogen atom, $R^b$ and $R^c$ form —(C=O)— together with the 3-position carbon atom attached to $R^b$ and $R^c$, and the broken line forms a single bond together with the solid line (compound 31); and a compound of general formula (I) wherein $X^1$ is a hydrogen atom, $X^2$ is a group of general formula (II) in α-configuration [wherein Ar is a single bond, A is a methylene group, G is —$CH_2CH_2$—, and E is $E^1$ (wherein $R^1$ and $R^2$ are each an —O—$CH_2CH_2CH_2$-$G^3$-$CON(R^3)$-Z substituent at the meta-position to G)], $R^a$ is a hydrogen atom, $R^b$ and $R^c$ form —(C=O)— together with the 3-position carbon atom attached to $R^b$ and $R^c$, and the broken line forms a single bond together with the solid line (compound 32).

Procedure D

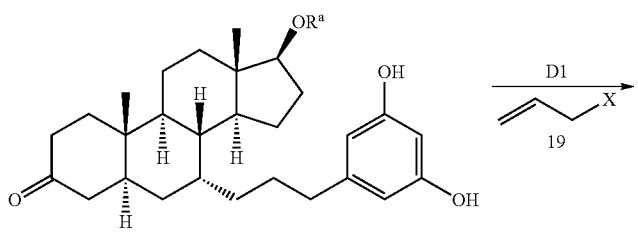

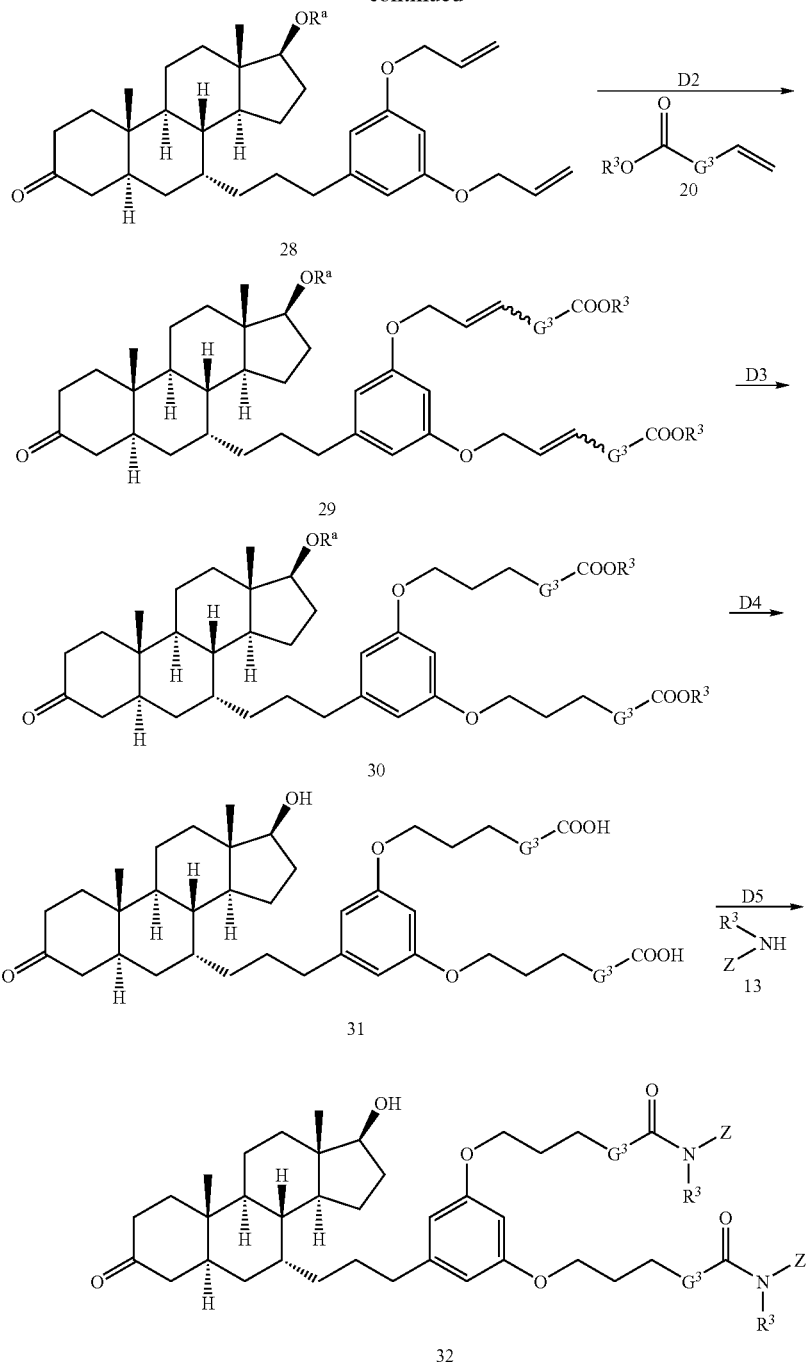

In Step D1, compound 24 is reacted with a base in an inert solvent, either alone or in combination, to give a salt of compound 24, which in turn is reacted with compound 19 in an inert solvent to prepare compound 28. This step may be performed in the same manner as Step A5 in Procedure A mentioned above.

In Step D2, compound 28 is reacted with compound 20 in an inert solvent and in the presence of an organometallic catalyst to prepare compound 29. This step may be performed in the same manner as Step A3 in Procedure A mentioned above.

In Step D3, catalytic reduction is performed in an alcohol solvent or an inert solvent to prepare compound 30. This step may be performed in the same manner as Step B3 in Procedure B mentioned above.

In Step D4, compound 30 is reacted with an acid in an aqueous solvent to prepare compound 31. This step may be performed in the same manner as Step A6 in Procedure A mentioned above.

In Step D5, compound 31 or a reactive derivative thereof (acid halides, mixed acid anhydrides, or active esters) is reacted with compound 13 or an acid addition salt thereof in an inert solvent to prepare compound 32. This step may be performed in the same manner as Step A7 in Procedure A mentioned above.

In the respective steps of the above Procedures A to D, a group in need of protection and deprotection, if any, can be protected and deprotected in a manner well known to those skilled in the art. To effect protection and deprotection, reference may be made to "Protective Groups in Organic Synthesis 2nd edition," Theodora W. Green, John Wiley & Sons, Inc., 1991 or other documents.

Compound 1 used as a starting material is known or may readily be prepared in a known manner with or without modifications [see, for example, J. Med. Chem. 35(11), 2113–2129 (1992); Synth. Commun. 24(16), 2325–2340 (1994); Steroids, 60(5), 414–422 (1995)].

Compound 21 used as a starting material is known or may readily be prepared in a known manner with or without modifications [see, for example, Tetrahedron Letters, 29(13), 1533–1536 (1988)].

The compound of general formula (I) according to the present invention (hereinafter also referred to as a "test substance") can be assayed for its effects including anti-androgenic activity by the use of the androgen receptor reporter gene assay, which is used to define "serving as an antagonist" and/or "free of agonistic effects" in the present invention, in combination with the following Assays A to F, as appropriate.

Assay A: In Vivo Assay in Rats

Assay A-1: Assay for Antagonistic Effects

Castrated rats administered with testosterone or dihydrotestosterone show an increase in their prostate and seminal vesicle weights. A test substance can be assayed for antagonistic effects by determining whether the test substance inhibits the testosterone- or dihydrotestosterone-induced increase in prostate and seminal vesicle weights. To effect the assay, reference may be made to J. Med. Chem., 41, 623–639 (1998) and Clinical Report, 29(4), 877–885 (1995), etc.

Assay A-2: Assay for Agonistic Effects

Castrated rats are continuously administered with a test substance. After administration, the test substance can be assayed for agonistic effects by determining whether the rats show an increase in the weights of androgen-responsive organs, i.e., prostates and seminal vesicles. To effect the assay, reference may be made to Journal of Japan Endocrine Society, 66, 597–606 (1990), etc.

Assay B: Assay Based on Androgen Receptor Dimerization

Assay B-1: Assay Based on the Ability to Inhibit Dimerization

Dihydrotestosterone causes androgen receptor dimerization. A test substance can be assayed for antagonistic effects by determining in a gel-shift assay whether the test substance inhibits androgen receptor dimerization. To effect the assay, reference may be made to J. Biol. Chem., 268, 19004–19012 (1993), J. Biol. Chem., 270, 19998–20003 (1995), etc.

Assay B-2: Assay Based on the Ability to Stimulate Androgen Receptor Dimerization A test substance can be assayed for agonistic effects by determining in a gel-shift assay whether the test substance stimulates androgen receptor dimerization. To effect the assay, reference may be made to J. Biol. Chem., 268, 19004–19012 (1993), J. Biol. Chem., 270, 19998–20003 (1995), etc.

Assay C: Assay Based on Ornithine Decarboxylase (ODC) Activity

A test substance can be assayed for agonistic and antagonistic effects by determining whether the test substance increases or decreases androgen-dependent ODC activity. To effect the assay, reference may be made to Anal. Biochem., 113, 352–355 (198), Journal of Japan Endocrine Society, 66, 597–606 (1990), etc.

Assay D: Assay Based on the Binding Ability to Androgen Receptors

A test substance can be assayed for antagonistic effects by determining in a binding assay whether the test substance inhibits the binding between androgen receptor and androgen. To effect the assay, reference may be made to Urology, 48, 157–163 (1996), J. Biol. Chem., 270, 19998–20003 (1995), Clinical Report, 29(4), 877–885 (1995), etc.

Assay E: Assay Based on an Increase or Decrease in Androgen Receptor Levels

A test substance can be assayed for agonistic and antagonistic effects on androgen receptor by treating androgen receptor-expressing cells with the test substance in the presence or absence of androgen and determining an increase or decrease in the intracellular androgen receptor levels. To effect the assay, reference may be made to Endocrinology, 129, 2000–2010 (1991), etc.

Assay F: Assay Based on Nuclear Transport of Androgen Receptors

A test substance can be assayed for agonistic and/or antagonistic effects by treating androgen receptor-expressing cells with the test substance in the presence or absence of androgen and examining the intracellular localization of androgen receptors by immunohistological staining to determine the presence of androgen receptor nuclear transport and/or the test substance-induced inhibition of androgen receptor nuclear transport. To effect the assay, reference may be made to J. Biol. Chem., 267, 968–974 (1992), etc.

The compound of general formula (I) according to the present invention is expected to provide an anti-androgen agent without the risk of developing androgen resistance due to prolonged administration and/or without the risk of side effects including liver toxicity. The compound of the present invention is therefore expected to be effective in preparing pharmaceutical compositions, e.g., therapeutic agents for diseases such as prostate cancer, benign prostatic hyperplasia, male pattern alopecia, precocious puberty, acne vulgaris, seborrhea and hypertrichosis. Upon pre-administration, the compound of general formula (I) according to the present invention is also expected to prevent or delay the onset of diseases such as prostate cancer, benign prostatic hyperplasia, male pattern alopecia, precocious puberty, acne vulgaris, seborrhea and hypertrichosis; it is therefore expected to provide prophylactic agents for these diseases.

A pharmaceutical composition comprising the compound of general formula (I) according to the present invention as an active ingredient may be administered by oral or parenteral route, desirably by oral route. The composition may be formulated into any dosage form suitable for the intended route of administration.

The pharmaceutical composition comprising the compound of general formula (I) according to the present invention as an active ingredient can be formulated by standard formulation techniques to give solid or liquid formulations such as tablets, capsules, granules, powders, syrups, injections or ointments, depending on the intended use. Examples of carriers and/or excipients used in formulation include solid or liquid materials such as lactose, magnesium stearate, starch, talc, gelatin, agar, pectin, gum arabic, olive oil, sesame oil, ethylene glycol and other materials commonly used.

The pharmaceutical composition comprising the compound of general formula (I) according to the present invention as an active ingredient may be incorporated into the formulation at varying concentrations depending on the type of dosage form, but it is usually desirable to incorporate the pharmaceutical composition at a concentration of 5% to 100% by weight. The pharmaceutical composition comprising the compound of general formula (I) according to the present invention as an active ingredient may be administered in widely varying amounts depending on the type of homeotherm (including human) to be administered, the severity of disease, the doctor's discretion, etc. Based on the active ingredient, the pharmaceutical composition is generally administered in an amount of 1 µg/kg to 500 mg/kg per day, preferably 20 µg/kg to 100 mg/kg per day. Also, it may be given as a single dose or divided doses per day to per month, depending on the severity of disease and/or the doctor's discretion.

EXAMPLES

Example 1

Examination of Flutamide and Bicalutamide for Agonistic Effects

Twenty-four hours before transfection, 1.0×10⁵ HeLa cells are cultured in a 12-well microplate containing phenol red-free DMEM/5% DCC-FBS. The HeLa cells are transfected with 500 ng/well MMTV-Luc vector, 100 ng/well pSG5-hAR and 5 ng/well Renilla Luc vector. Transfection is performed in phenol red-free DMEM medium using 3 µL/well lipofectamine. Nine hours after transfection, the medium is replaced by phenol red-free DMEM/3% DCC-FBS supplemented with 10 µmol/L hydroxyflutamide or bicalutamide. Forty-eight hours after the replacement of the medium, transcriptional activity is determined by a Dual-Luciferase Reporter Assay System according to the following equation: (transcriptional activity)=(firefly luciferase activity)/(Renilla luciferase activity). Both hydroxyflutamide and bicalutamide provided a more than 5-fold increase in transcriptional activity as compared to the value for the absence of these compounds; hydroxyflutamide and bicalutamide were confirmed to have agonistic effects (Table 1).

TABLE 1

|  | Luciferase activity (Fold induction)[1] |
|---|---|
| Absence | 1.00 |
| 10 µmol/L Hydroxyflutamide | 7.84 (>5.0) |
| 10 µmol/L Bicalutamide | 7.62 (>5.0) |

[1]calculated assuming that luciferase activity in the absence of the compounds is set to 1.00

Example 2

Examination of Hydroxyflutamide and Bicalutamide for Antagonistic Effects

Twenty-four hours before transfection, 1.0×10⁵ HeLa cells are cultured in a 12-well microplate containing phenol red-free DMEM/5% DCC-FBS. The HeLa cells are transfected with 500 ng/well MMTV-Luc vector, 100 ng/well pSG5-hAR and 5 ng/well Renilla Luc vector. Transfection is performed in phenol red-free DMEM medium using 3 µL/well lipofectamine. Nine hours after transfection, the medium is replaced by phenol red-free DMEM/3% DCC-FBS supplemented with 0.1 nmol/L DHT and 1.0 µmol/L hydroxyflutamide or bicalutamide. Forty-eight hours after the replacement of the medium, transcriptional activity is determined by a Dual-Luciferase Reporter Assay System according to the following equation: (transcriptional activity)=(firefly luciferase activity)/(Renilla luciferase activity). Both hydroxyflutamide and bicalutamide inhibited DHT-induced transcriptional activity to less than 50%; hydroxyflutamide and bicalutamide were confirmed to have antagonistic effects (Table 2).

TABLE 2

|  | Luciferase activity (Relative activity)[2] |
|---|---|
| 0.1 nmol/L DHT | 100 |
| 1.0 µmol/L Hydroxyflutamide | 29.0 (<50.0) |
| 1.0 µmol/L Bicalutamide | 32.0 (<50.0) |

[2]calculated assuming that luciferase activity given by 0.1 nmol/L DHT is set to 100

Example 3

Synthesis of 17β-hydroxy-7α-(3-(3-hydroxy-5-(3-(N-N-dimethylaminocarbonyl)propoxy phenyl)propyl)-5α-androstan-3-one (Step 1)

17β-(tert-Butyldimethylsilyloxy)-7α-(3-(3,5-dihydroxyphenyl)propyl)-5α-androstan-3-one

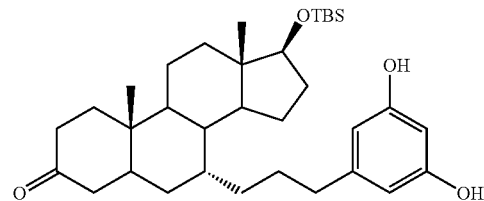

Under argon atmosphere, 7α-allyl-17β-(tert-butyldimethylsilyloxy)-5α-androstan-3-one (200 mg), 3,5-dibenzyloxystyrene (285 mg) and benzylidene-bis(tricyclohexylphosphine)-dichlororuthenium (37 mg) were dissolved in methylene chloride (2.5 ml) and stirred at 30° C. for 14 hours. After evaporation under reduced pressure to remove the solvent, the residue was purified by silica gel column chromatography (eluent: ethyl acetate/n-hexane=1/5) to give 17β-(tert-butyldimethylsilyloxy)-7α-(3-(3,5-dibenzyloxyphenyl)-2-propenyl)-5α-androstan-3-one.

The resulting 17β-(tert-butyldimethylsilyloxy)-7α-(3-(3,5-dibenzyloxyphenyl)-2-propenyl)-5α-androstan-3-one was dissolved in ethyl acetate (3 ml) and stirred in the presence of 10% palladium/carbon (50 mg) at 25° C. for 4 days under hydrogen atmosphere. After the reaction mixture was filtered and evaporated under reduced pressure to remove the solvent, the resulting residue was purified by silica gel column chromatography (eluent: ethyl acetate/n-hexane=1/

1) to give 17β-(tert-butyldimethylsilyloxy)-7α-(3-(3,5-dihydroxyphenyl)propyl)-5α-androstan-3-one (107.5 mg, yield 43%).

¹H-NMR (270 MHz, CDCl₃) δ: 0.02 (6H, s), 0.69 (3H, s), 0.87 (9H, s), 1.00 (3H, s), 0.83–2.61 (27H, m), 3.54 (1H, t, J=8.1 Hz), 5.76 (2H, brs), 6.17–6.29 (3H, m).

(Step 2)

17β-(tert-Butyldimethylsilyloxy)-7α-(3-(3-benzyloxy-5-hydroxyphenyl)propyl)-5α-androstan-3-one

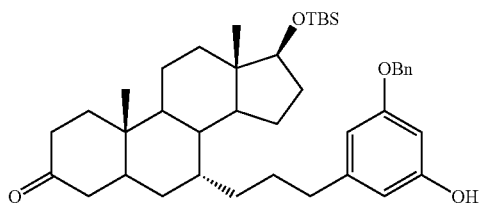

17β-(tert-Butyldimethylsilyloxy)-7α-(3-(3,5-dihydroxyphenyl)propyl)-5α-androstan-3-one (75 mg), benzyl bromide (16.9 µl) and potassium carbonate (56 mg) were suspended in DMF (1 ml) and stirred overnight at 25° C. After addition of saturated aqueous ammonium chloride, the reaction mixture was extracted with ethyl acetate and then washed with water and saturated aqueous sodium chloride. The organic layer was dried over anhydrous magnesium sulfate and then filtered. After evaporation under reduced pressure to remove the solvent, the resulting residue was subjected to silica gel column chromatography (eluent: ethyl acetate/n-hexane=1/4) to give 17β-(tert-butyldimethylsilyloxy)-7α-(3-(3-benzyloxy-5-hydroxyphenyl)propyl)-5α-androstan-3-one (21.0 mg, yield 24%).

¹H-NMR (270 MHz, CDCl₃) δ: 0.02 (6H, s), 0.70 (3H, s), 0.88 (9H, s), 1.02 (3H, s), 0.83–2.60 (27H, m), 3.54 (1H, t, J=8.2 Hz), 5.01 (2H, s), 5.22 (1H, brs), 6.25–6.34 (2H, m), 6.39 (1H, brs), 7.26–7.44 (5H, m).

(Step 3)

17β-(tert-Butyldimethylsilyloxy)-7α-(3-(3-hydroxy-5-(3-(N,N-dimethylaminocarbonyl)propoxy)phenyl)propyl)-5α-androstan-3-one

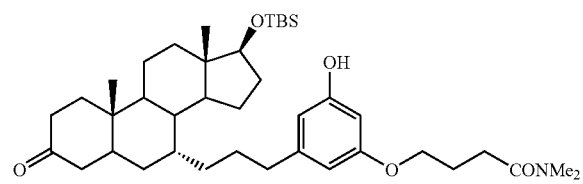

A solution of 17β-(tert-butyldimethylsilyloxy)-7α-(3-(3-benzyloxy-5-hydroxyphenyl)propyl)-5α-androstan-3-one (21.0 mg) in DMF (0.3 ml) was cooled on ice, followed by addition of sodium hydride (1.6 mg) and 15-crown-5-ether (7.8 µl). After the reaction mixture was stirred for 30 minutes, 4-bromo-n-butyric acid benzyl ester (10 mg) was added and stirred on ice for 1 hour. Water was added to the reaction mixture, which was then extracted with ethyl acetate. The organic layer was washed with saturated aqueous sodium chloride, dried over anhydrous magnesium sulfate and then filtered. After evaporation under reduced pressure to remove the solvent, the resulting residue was purified by silica gel column chromatography (eluent: ethyl acetate/n-hexane=1/4) to give 17β-(tert-butyldimethylsilyloxy)-7α-(3-(3-benzyloxy-5-(3-(benzyloxycarbonyl)propoxy)phenyl)propyl)-5α-androstan-3-one.

The resulting 17β-(tert-butyldimethylsilyloxy)-7α-(3-(3-benzyloxy-5-(3-(benzyloxycarbonyl)propoxy)phenyl)propyl)-5α-androstan-3-one was dissolved in ethyl acetate (2 ml) and stirred in the presence of 10% palladium/carbon (5 mg) at room temperature for 11 hours under hydrogen atmosphere. The reaction mixture was filtered and evaporated under reduced pressure to remove the solvent, thereby giving 17β-(tert-butyldimethylsilyloxy)-7α-(3-(3-hydroxy-5-(3-carboxylpropoxy)phenyl)propyl)-5α-androstan-3-one.

The resulting 17β-(tert-butyldimethylsilyloxy)-7α-(3-(3-hydroxy-5-(3-carboxylpropoxy)phenyl)propyl)-5α-androstan-3-one was dissolved in THF (0.5 ml) and cooled on ice, followed by addition of ethyl chlorocarbonate (3.8 µl) and then triethylamine (5.5 µl). After the reaction mixture was stirred for 20 minutes, a 2M THF solution of dimethylamine (26.9 µl) was added and stirred for 1 hour. Saturated aqueous NH₄Cl was added to the reaction mixture, which was then extracted with ethyl acetate. The organic layer was washed with water and saturated aqueous sodium chloride, dried over anhydrous magnesium sulfate and then filtered. After evaporation under reduced pressure to remove the solvent, the resulting residue was purified by silica gel column chromatography (eluent: ethyl acetate/n-hexane=1/3) to give 17β-(tert-butyldimethylsilyloxy)-7α-(3-(3-hydroxy-5-(3-(N,N-dimethylaminocarbonyl)propoxy)phenyl)propyl)-5α-androstan-3-one (14.0 mg, yield 64%).

¹H-NMR (270 MHz, CDCl₃) δ: 0.02 (6H, s), 0.70 (3H, s), 0.87 (9H, s), 1.02 (3H, s), 0.82–2.58 (31H, m), 2.95 (3H, s), 3.01 (3H, s), 3.54 (1H, t, J=8.0 Hz), 3.98 (2H, t, J=5.9 Hz), 6.19 (1H, brs), 6.27 (3H, s).

(Step 4)

17β-Hydroxy-7α-(3-(3-hydroxy-5-(3-(N,N-dimethylaminocarbonyl)propoxy)phenyl)propyl)-5α-androstan-3-one

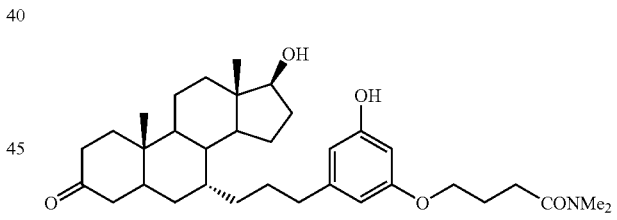

To a solution of 17β-(tert-butyldimethylsilyloxy)-7α-(3-(3-hydroxy-5-(3-(N,N-dimethylaminocarbonyl)propoxy)phenyl)propyl)-5α-androstan-3-one (12.0 mg) in acetone (1 ml), 2N hydrochloric acid (1 ml) was added at 25° C. and stirred for 35 minutes. Water was added to the reaction mixture, which was then extracted with ethyl acetate. The organic layer was washed with saturated aqueous sodium chloride, dried over anhydrous magnesium sulfate and then filtered. After evaporation under reduced pressure to remove the solvent, the resulting residue was purified by silica gel column chromatography (eluent: ethyl acetate) to give 17β-hydroxy-7α-(3-(3-hydroxy-5-(3-(N,N-dimethylaminocarbonyl)propoxy)phenyl)propyl)-5α-androstan-3-one (6.5 mg, yield 65%).

¹H-NMR (270 MHz, CDCl₃) δ: 0.75 (3H, s), 1.03 (3H, s), 0.86–2.58 (32H, m), 2.96 (3H, s), 3.02 (3H, s), 3.63 (1H, t, J=8.3 Hz), 3.98 (2H, t, J=5.9 Hz), 5.97 (1H, brs), 6.24–6.31 (3H, m).

FAB-MS: 554.7 (M+H).

Example 4

Examination of Agonistic and Antagonistic Effects

The compound prepared in Example 3 was examined for agonistic and antagonistic effects on androgen receptor-mediated transcriptional activation.

The compound was assayed for agonistic effects in the same manner as shown in Example 1 in order to calculate agonist activity using the following equation, which in turn was used to calculate a FI5 value (i.e., a concentration at which the compound provides a 5-fold increase in transcriptional activity as compared to the value for the absence of the compound). The compound was added at concentrations of 1, 10, 100, 1000 and 10000 nmol/L.

Agonist activity=(transcriptional activity in the presence of the compound)/(transcriptional activity in the absence of the compound)

The compound was also assayed for antagonistic effects in the same manner as shown in Example 2 in order to calculate antagonist activity using the following equation, which in turn was used to calculate a IC50 value (i.e., a concentration at which the compound causes 50% inhibition of transcriptional activity induced by DHT (0.1 nmol/L) in the absence of the compound). The compound was added at concentrations of 1, 10, 100, 1000 and 10000 nmol/L in combination with DHT (0.1 nmol/L). The results obtained are shown in Table 3.

Antagonist activity=(transcriptional activity in the presence of the compound)/(transcriptional activity in the absence of the compound)×100

TABLE 3

| Compound | IC50 value (nM) | FI5 value (nM) |
|---|---|---|
| Compound from Example 3 | 392 | ND* |

*ND in the table means that a FI5 value cannot be calculated because the compound provides a less than 5-fold increase in transcriptional activity.

In view of the foregoing, the compound of the present invention was confirmed to have antagonistic effects, but be substantially free of agonistic effects on androgen receptor-mediated transcriptional activation.

INDUSTRIAL APPLICABILITY

The compound of general formula (I) according to the present invention is expected to provide an anti-androgen agent without the risk of developing androgen resistance due to prolonged administration and/or without the risk of side effects including liver toxicity. The compound of the present invention is therefore expected to be effective in preparing pharmaceutical compositions, e.g., therapeutic agents for diseases such as prostate cancer, benign prostatic hyperplasia, male pattern alopecia, precocious puberty, acne vulgaris, seborrhea and hypertrichosis. Upon pre-administration, the compound of general formula (I) according to the present invention is also expected to prevent or delay the onset of diseases such as prostate cancer, benign prostatic hyperplasia, male pattern alopecia, precocious puberty, acne vulgaris, seborrhea and hypertrichosis; it is therefore expected to provide prophylactic agents for these diseases.

The invention claimed is:

1. A compound of general formula (I):

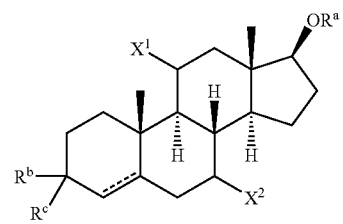

(I)

wherein
X$^1$ is hydrogen, and X$^2$ is a group of general formula (II):

-Ar-A-G-E (II)

having an α-configutation,
R$^a$ represents a hydrogen atom or a protecting group for a hydroxyl group,
R$^b$ and R$^c$ form an optionally protected —(C=O)— together with the 3-position carbon atom attached to R$^b$ and R$^c$, and
the broken line forms a single bond or a double bond together with the solid line,
wherein Ar is a single bond or an aromatic hydrocarbon group, A is a methylene group wherein Ar is a single bond, and A is —O— when Ar is an aromatic hydrocarbon group,
G is an optionally hydroxyl substituted linear C$_2$–C$_{15}$ alkylene group, and
E represents a group selected from the following formulae E$^1$ to E$^{10}$:

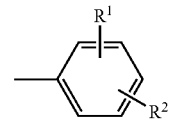

E$^1$

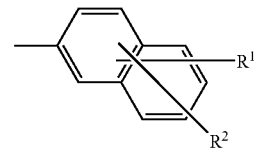

E$^2$

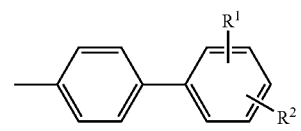

E$^3$

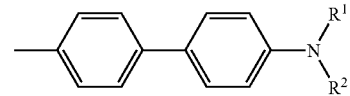

E$^4$

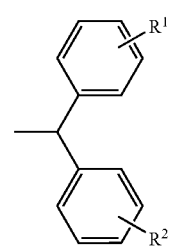

E$^5$

-continued

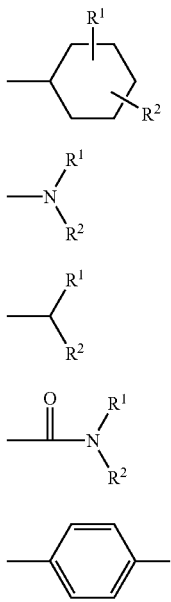

wherein $R^1$ and $R^2$, which are the same or different, each represent a group of general formula (III):

-J-$G^2$-Q-Z  (III)

[wherein J represents a single bond, a methylene group or —O—, $G^2$ represents a single bond, an optionally substituted linear or branched $C_1$–$C_{10}$ alkylene group, an optionally substituted linear or branched $C_2$–$C_{10}$ alkenylene group, or an optionally substituted linear or branched $C_2$–$C_{10}$ alkynylene group, Q represents a single bond or a group selected from the following formulae $Q^1$ to $Q^{10}$:

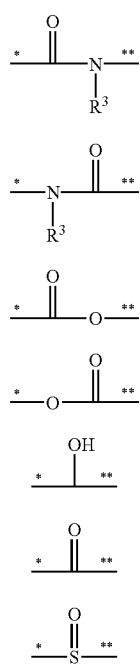

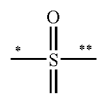

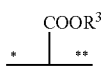

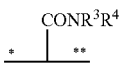

(wherein $R^3$ and $R^4$, which are the same or different, each represent a hydrogen atom or a linear or branched $C_1$–$C_{10}$ lower alkyl group, the bond marked with * is linked to $G^2$, and the bond marked with ** is linked to Z), and Z represents a hydrogen atom, a linear or branched $C_1$–$C_{10}$ alkyl group which may be substituted with a halogen atom, a linear or branched $C_2$–$C_{10}$ alkenyl group which may be substituted with a halogen atom, a linear or branched $C_2$–$C_{10}$ alkynyl group which may be substituted with a halogen atom, or a group of general formula (IV):

—O—$R^d$  (IV)

(wherein $R^d$ represents a hydrogen atom or a protecting group for a hydroxyl group)], provided Z is not a hydrogen atom when J, $G^2$ and Q simultaneously represent a single bond, or a pharmaceutically acceptable salt of the compound or a prodrug thereof.

2. The compound according to claim 1, wherein E is $E^1$, or a pharmaceutically acceptable salt of the compound or a prodrug thereof.

3. The compound according to claim 1, wherein E is $E^1$ having $R^1$ and $R^2$ at the meta-positions, or a pharmaceutically acceptable salt of the compound or a prodrug thereof.

4. The compound according to claim 1, wherein E is $E^2$, $E^3$, $E^4$ or $E^{10}$, or a pharmaceutically acceptable salt of the compound or a prodrug thereof.

5. The compound according to claim 1, wherein Q is $Q^1$, or a pharmaceutically acceptable salt of the compound or a prodrug thereof.

6. The compound according to claim 1, wherein Q is $Q^7$ or $Q^9$, or a pharmaceutically acceptable salt of the compound or a prodrug thereof.

7. The compound according to claim 1, wherein Z is a linear or branched $C_1$–$C_{10}$ alkyl group which may be substituted with a halogen atom, or a pharmaceutically acceptable salt of the compound or a prodrug thereof.

8. The compound according to claim 1, wherein Z is a 4,4,5,5,5-pentafluoropentyl group, or a pharmaceutically acceptable salt of the compound or a prodrug thereof.

9. The compound according to claim 1, wherein Z is an n-pentyl group, or a pharmaceutically acceptable salt of the compound or a prodrug thereof.

10. The compound according to claim 1, wherein $G^2$ is an optionally substituted linear or branched $C_1$–$C_{10}$ alkylene group, or a pharmaceutically acceptable salt of the compound or a prodrug thereof.

11. The compound according to claim 1, wherein $G^2$ is an optionally substituted linear $C_1$–$C_5$ alkylene group, or a pharmaceutically acceptable salt of the compound or a prodrug thereof.

12. The compound according to claim 1, wherein J is —O—, or a pharmaceutically acceptable salt of the compound or a prodrug thereof.

13. The compound according to claim 1, wherein Ar is a single bond, or a pharmaceutically acceptable salt of the compound or a prodrug thereof.

14. The compound according to claim 1, wherein G is a linear $C_2$–$C_5$ alkylene group, or a pharmaceutically acceptable salt of the compound or a prodrug thereof.

15. The compound according to claim 1, wherein the broken line forms a single bond together with the solid line, or a pharmaceutically acceptable salt of the compound or a prodrug thereof.

16. The compound according to claim 1, wherein $X^2$ is selected from the following formulae (1) to (10):

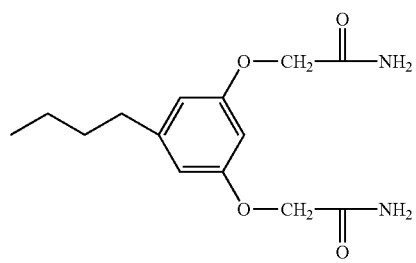
(1)

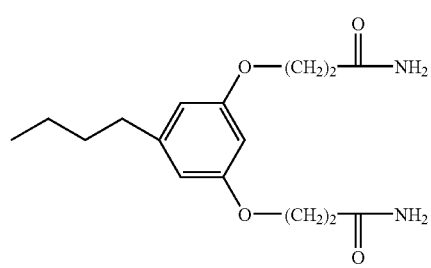
(2)

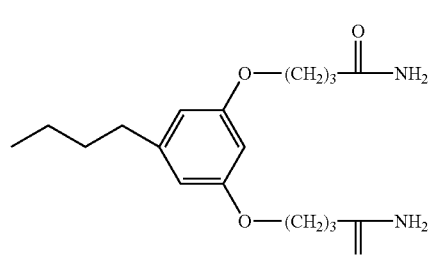
(3)

-continued

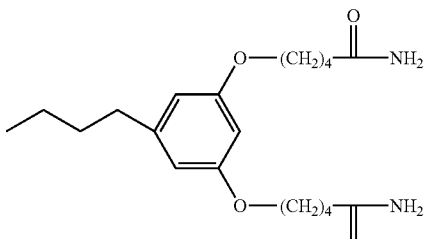
(4)

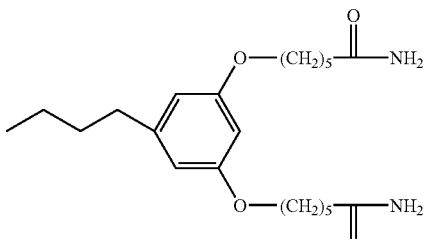
(5)

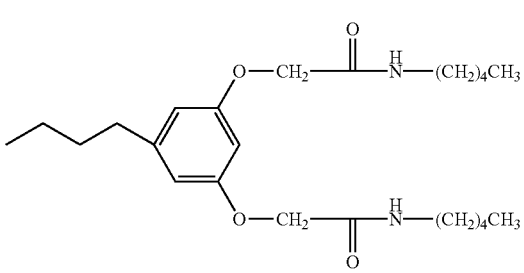
(6)

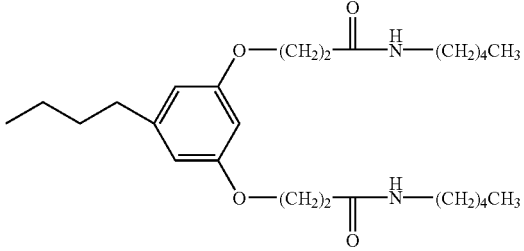
(7)

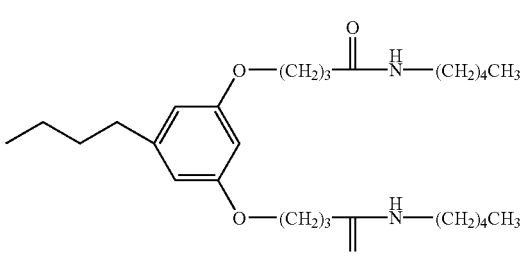
(8)

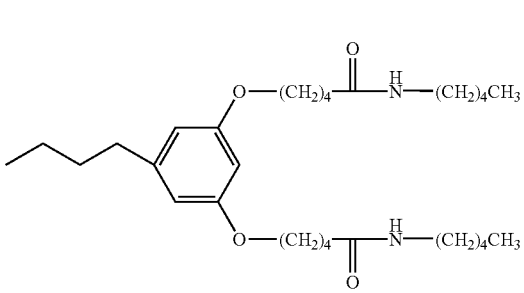
(9)

-continued (10)

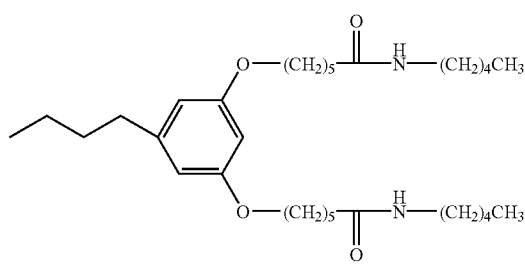

or a pharmaceutically acceptable salt of the compound or a prodrug thereof.

17. A pharmaceutical composition which comprises, as an active ingredient, the compound according to claim 1 or a pharmaceutically acceptable salt of the compound or a prodrug thereof, said compound being selected from:

17β-hydroxy-7α-[3-{3,5-bis(carbamoylmethoxy)phenyl}propyl]androstan-3-one;

17β-hydroxy-7α-[3-{3,5-bis(pentylcarbamoylmethoxy)phenyl}propyl]androstan-3-one;

17β-hydroxy-7α-[3-{3,5-bis(2-carbamoylethoxy)phenyl}propyl]androstan-3-one;

17β-hydroxy-7α-(3-[3,5-bis{2-(pentylcarbamoyl)ethoxy}phenyl]propyl)androstan-3-one;

17β-hydroxy-7α-[3-{3,5-bis(3-carbamoylpropoxy)phenyl}propyl]androstan-3-one;

17β-hydroxy-7α-(3-[3,5-bis{3-(pentylcarbamoyl)propoxy}phenyl]propyl)androstan-3-one;

17β-hydroxy-7α-[3-{3,5-bis(4-carbamoylbutoxy)phenyl}propyl]androstan-3-one;

17β-hydroxy-7α-(3-[3,5-bis{4-(pentylcarbamoyl)butoxy}phenyl]propyl)androstan-3-one;

17β-hydroxy-7α-[3-{3,5-bis(5-carbamoylpentyloxy)phenyl}propyl]androstan-3-one; and 17β-hydroxy-7α-(3-[3,5-bis{5-(pentylcarbamoyl)pentyloxy}phenyl]propyl)androstan-3-one.

18. A pharmaceutical composition which comprises, as an active ingredient, the compound according to claim 1 or a pharmaceutically acceptable salt of the compound or a prodrug thereof.

19. A compound of general formula (I):

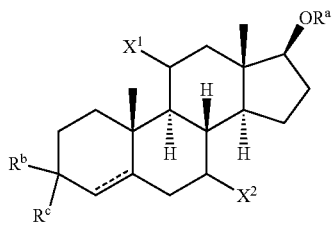

(I)

wherein $X^1$ is a hydrogen atom and $X^2$ is a group of general formula (V):

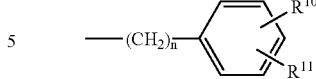

(V)

[wherein n represents an integer of 1 to 10, $R^{10}$ represents a hydroxyl group, an alkoxy group or an alkoxycarbonyl group, and $R^{11}$ represents an alkoxy group, an alkoxycarbonyl group or a group of general formula (VI):

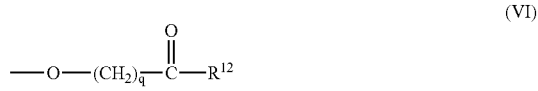

(VI)

(wherein q represents an integer of 1 to 10, and $R^{12}$ represents a hydroxyl group or an alkylamino group)], $R^a$ represents a hydrogen atom or a protecting group for a hydroxyl group, $R^b$ and $R^c$ form an optionally protected —(C=O)— together with the 3-position carbon atom attached to $R^b$ and $R^c$, and the broken line forms a single bond or a double bond together with the solid line, or a pharmaceutically acceptable salt of the compound or a prodrug thereof.

20. A compound of general formula (VII):

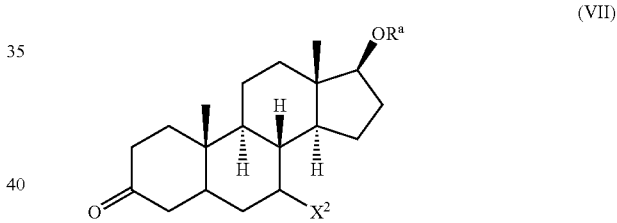

(VII)

wherein $X^2$ represents a group of general formula (V):

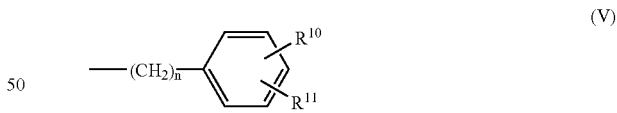

(V)

[wherein n represents an integer of 1 to 10, $R^{10}$ represents a hydroxyl group, an alkoxy group or an alkoxycarbonyl group, and $R^{11}$ represents an alkoxy group, an alkoxycarbonyl group or a group of general formula (VI):

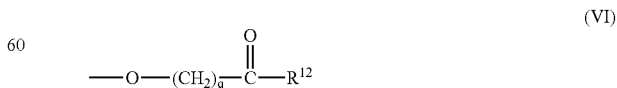

(VI)

(wherein q represents an integer of 1 to 10, and $R^{12}$ represents a hydroxyl group or an alkylamino group)], and $R^a$ represents a hydrogen atom or a protecting group for a hydroxyl group, or a pharmaceutically acceptable salt of the compound or a prodrug thereof.

21. The compound of according to claim 20, wherein the group of general formula (V) is a group represented by general formula (VIII):

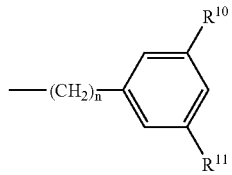

(VIII)

[wherein n represents an integer of 1 to 6, $R^{10}$ represents a hydroxyl group, an alkoxy group or an alkoxycarbonyl group, and $R^{11}$ represents an alkoxy group, an alkoxycarbonyl group or a group of general formula (VI):

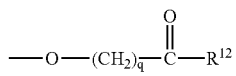

(VI)

(wherein q represents an integer of 1 to 6, and $R^{12}$ represents a hydroxyl group or an alkylamino group)], or a pharmaceutically acceptable salt of the compound or a prodrug thereof.

22. The compound according to claim 19, wherein $R^{10}$ is a hydroxyl, group, a $C_1$–$C_6$ alkoxy group or a $C_1$–$C_6$ alkoxycarbonyl group, and $R^{11}$ is a $C_1$–$C_6$ alkoxy group, a $C_1$–$C_6$ alkoxycarbonyl group or a group of general formula (VI):

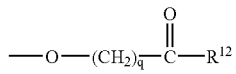

(VI)

(wherein q is an integer of 1 to 6, and $R^{12}$ is a hydroxyl group or a dialkylamino group) , or a pharmaceutically acceptable salt of the compound or a prodrug thereof.

23. The compound according to claim 22, wherein $R^{10}$ is a hydroxyl group and $R^{11}$ is a group of general formula (VI):

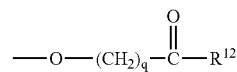

(VI)

(wherein q is an integer of 1 to 6, and $R^{12}$ is a dialkylamino group), or a pharmaceutically acceptable salt of the compound or a prodrug thereof.

24. The compound according to claim 23, wherein q is an integer of 1 to 6 and alkyl groups in the dialkylamino group are each independently a $C_1$–$C_6$ alkyl group, or a pharmaceutically acceptable salt of the compound or a prodrug thereof.

25. The compound according to claim 24, wherein q is 3 and the dialkylamino group is a dimethylamino group, or a pharmaceutically acceptable salt of the compound or a prodrug thereof.

26. The compound according to claim 19, wherein the compound of general formula (I) is selected from the group consisting of:

17β-hydroxy-7α-(3-(3-hydroxy-5-(3-(N,N-dimethylaminocarbonyl)propoxy)phenyl)propyl)-5α-androstan-3-one;

17β-hydroxy-7α-(3-(3,5-dimethoxyphenyl)propyl)-5α-androstan-3-one;

17β-hydroxy-7α-(3-(3-methoxy-4-hydroxyphenyl)propyl)-5α-androstan-3-one;

17β-hydroxy-7α-(3-(3-methoxycarbonyl-4-hydroxyphenyl)propyl)-5α-androstan-3-one;

17β-hydroxy-7α-(3-(3-hydroxy-4-(3-(N,N-dimethylaminocarbonyl)propoxy)phenyl)propyl)-5α-androstan-3-one;

17β-hydroxy-7α-(3-(3-methoxycarbonyl-4-(3-carboxypropoxy)phenyl)propyl)-5α-androstan-3-one; and 17β-hydroxy-7α-(3-(3-methoxycarbonyl-4-(3-(N,N-dimethylaminocarbonyl)propoxy)phenyl)propyl)-5α-androstan-3-one, or a pharmaceutically acceptable salt of the compound or a prodrug thereof.

27. A pharmaceutical composition which comprises, as an active ingredient, the compound according to claim 19 or a pharmaceutically acceptable salt of the compound or a prodrug thereof.

* * * * *

UNITED STATES PATENT AND TRADEMARK OFFICE
CERTIFICATE OF CORRECTION

| | | |
|---|---|---|
| PATENT NO. | : 7,018,993 B2 | Page 1 of 1 |
| APPLICATION NO. | : 10/312730 | |
| DATED | : March 28, 2006 | |
| INVENTOR(S) | : Ohta et al. | |

It is certified that error appears in the above-identified patent and that said Letters Patent is hereby corrected as shown below:

On title page, Item 54, and in Column 1, line 1, the title of the invention should read --NOVEL ANTI-ANDROGEN AGENTS--.

Signed and Sealed this

First Day of August, 2006

JON W. DUDAS
*Director of the United States Patent and Trademark Office*